(12) United States Patent
Nguyen et al.

(10) Patent No.: US 6,534,506 B2
(45) Date of Patent: Mar. 18, 2003

(54) INHIBITORS OF PRENYL-PROTEIN TRANSFERASE

(75) Inventors: Diem N. Nguyen, North Wales, PA (US); Craig A. Stump, Pottstown, PA (US); Theresa M. Williams, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/828,259

(22) Filed: Apr. 6, 2001

(65) Prior Publication Data

US 2002/0123497 A1 Sep. 5, 2002

Related U.S. Application Data

(60) Provisional application No. 60/195,951, filed on Apr. 10, 2000.

(51) Int. Cl.$^7$ .................. C07D 498/22; C07D 487/22; C07D 513/22; A61K 31/529; A61P 35/00
(52) U.S. Cl. .............. 514/250; 540/456; 540/460; 540/469; 540/472; 544/229; 544/231; 544/362; 544/368; 544/370; 548/110; 548/154; 548/218; 548/322.5
(58) Field of Search ...................... 540/456, 460, 540/469, 472, 453, 466; 514/250

(56) References Cited

U.S. PATENT DOCUMENTS

| | | |
|---|---|---|
| 5,736,539 A | 4/1998 | Graham et al. |
| 5,756,528 A | 5/1998 | Anthony et al. |
| 5,856,326 A | 1/1999 | Anthony et al. |
| 5,859,012 A | 1/1999 | Dinsmore et al. |
| 5,859,015 A | 1/1999 | Graham et al. |
| 5,885,995 A | 3/1999 | Dinsmore |
| 5,919,785 A | 7/1999 | Dinsmore et al. |
| 6,329,376 B1 * | 12/2001 | Bergman ............... 540/469 |
| 6,350,755 B1 * | 2/2002 | deSolms et al. ............ 540/456 |

FOREIGN PATENT DOCUMENTS

| | | |
|---|---|---|
| EP | 0 670 314 A1 | 3/1995 |
| WO | WO 99/09985 | 3/1999 |
| WO | WO 99/20609 | 4/1999 |
| WO | WO 00/01382 | 1/2000 |
| WO | WO 00/01701 | 1/2000 |
| WO | WO 00/01702 | 1/2000 |

OTHER PUBLICATIONS

Smith, Clin Cancer Res 2002 Jun.;8(6):2002–9.*
A. A. Adjei et al., A Phase I Trial of the Farnesyl Transferase Inhibitor SCH66336: Evidence for Biological and Clinical Activity, Cancer Research, vol. 60, pp. 1871–1877, Apr. 2000.

J. Zujewski et al., Phase I and Pharmacokinetic Study of Farnesyl Protein Transferase Inhibitor R115777 in Advanced Cancer, J. of Clinical Oncology, vol. 18, No. 4, pp. 927–941, Feb. 2000.

N. E. Kohl et al., Inhibition of farnesyltransferase induces regression of mammary and salivary carcinomas in ras transgenic mice, Nature Medicine, vol. 1, No. 8, pp. 792–797, Aug. 1995.

N. E. Kohl et al., Protein farnesyltransferase inhibitors block the growth of ras–dependent tumors in nude mice, Proc. Natl. Acad. Sci. USA, vol. 91, pp. 9141–9145, Sep. 1994.

L. Sepp–Lorenzino et al., A Peptidomimetic Inhibitor of farnesyl:Protein Transferase Blocks the anchorage–dependent and –independent Growth of Human Tumor Cell Lines, Cancer Research, vol. 55, pp. 5302–5309, Nov. 1995.

S. L. Graham et al., Oncologic, Endocrine & Metabolic Inhibitors of Protein Farnesylation, Exp. Opin. Ther. Patent, vol. 6(12), pp. 1295–1304, 1996.

S. L. Graham, Oncologic, Endocrine & Metabolic Inhibitors of Protein Farnesylation: A New Approach to Cancer Chemotherapy, Exp. Opin. Ther. Patents, vol. 5(12), pp. 1269–1285, 1995.

G. L. Bolton et al., Ras Oncogene Directed Approaches in Cancer Chemotherapy, Annual Reports in Medicinal Chemistry, vol. 29, pp. 165–174, 1994.

B. N. Balasubramanian et al., Recent Developments in Cancer Cytotoxics, Annual Reports in Medicinal Chemistry, vol. 33, pp. 151–162, 1998.

T. M. Williams et al., N–Arylpiperazinone Inhibitors of Farnesyltransferase: Discovery and Biological Activity, J. Med. Chem., vol. 42, pp. 3779–3784, 1999.

T. M. Williams, Inhibitors of Protein Farnesylation 1998, Exp. Opin. Ther. Patents, vol. 8(5), pp. 553–569.

I. M. Bell, Inhibitors of Protein Prenylation 2000, Exp. Opin. Ther. Patents, vol. 10(12), pp. 1813–1831.

T. M. Williams, Inhibitors of Protein Prenylation 1999, Exp. Opin. Ther. Patents, vol. 9(9), pp. 1263–1280.

* cited by examiner

*Primary Examiner*—Mark L. Berch
(74) *Attorney, Agent, or Firm*—Dianne Brown; Mark R. Daniel

(57) ABSTRACT

The present invention is directed to peptidomimetic macrocyclic compounds which inhibit prenyl-protein transferase and the prenylation of the oncogene protein Ras. The invention is further directed to chemotherapeutic compositions containing the compounds of this invention and methods for inhibiting prenyl-protein transferase and the prenylation of the oncogene protein Ras.

17 Claims, No Drawings

SEQUENCE LISTING

<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: N-terminus of Ras protein

<400> SEQUENCE: 1

Cys Val Leu Leu
1

<210> SEQ ID NO 2
<211> LENGTH: 4
<212> TYPE: PRT
<213> ORGANISM: Artificial Sequence
<220> FEATURE:
<223> OTHER INFORMATION: N-terminus of Ras protein

<400> SEQUENCE: 2

Cys Val Leu Ser
1

<210> SEQ ID NO 3
<211> LENGTH: 15
<212> TYPE: PRT
<213> ORGANISM: Artificial Sequence
<220> FEATURE:
<223> OTHER INFORMATION: Completely Synthetic Amino Acid

<400> SEQUENCE: 3

Gly Lys Lys Lys Lys Lys Lys Ser Lys Thr Lys Cys Val Ile Met
1               5                   10                  15

<210> SEQ ID NO 4
<211> LENGTH: 52
<212> TYPE: DNA
<213> ORGANISM: Artificial Sequence
<220> FEATURE:
<223> OTHER INFORMATION: Artificial Nucleotide Sequence

<400> SEQUENCE: 4
gagagggaat tcgggccctt cctgcatgct gctgctgctg ctgctgctgg gc    52

<210> SEQ ID NO 5
<211> LENGTH: 41
<212> TYPE: DNA
<213> ORGANISM: Artificial Sequence
<220> FEATURE:
<223> OTHER INFORMATION: Artificial Antisense Nucleotide Sequence

<400> SEQUENCE: 5
gagagagctc gaggttaacc cgggtgcgcg gcgtcggtgg t    41

<210> SEQ ID NO 6
<211> LENGTH: 42
<212> TYPE: DNA
<213> ORGANISM: Artificial Sequence
<220> FEATURE:
<223> OTHER INFORMATION: Artificial Nucleotide Sequence

<400> SEQUENCE: 6
gagagagtct agagttaacc cgtggtcccc gcgttgcttc ct    42

<210> SEQ ID NO 7
<211> LENGTH: 43
<212> TYPE: DNA
<213> ORGANISM: Artificial Sequence
<220> FEATURE:
<223> OTHER INFORMATION: Artificial Antisense Nucleotide Sequence

<400> SEQUENCE: 7
gaagaggaag cttggtaccg ccactgggct gtaggtggtg gct    43

<210> SEQ ID NO 8
<211> LENGTH: 27
<212> TYPE: DNA
<213> ORGANISM: Artificial Sequence
<220> FEATURE:
<223> OTHER INFORMATION: Artificial Nucleotide Sequence

<400> SEQUENCE: 8
ggcagagctc gtttagtgaa ccgtcag    27

<210> SEQ ID NO 9
<211> LENGTH: 27
<212> TYPE: DNA
<213> ORGANISM: Artificial Sequence
<220> FEATURE:
<223> OTHER INFORMATION: Artificial Antisense Nucleotide Sequence

<400> SEQUENCE: 9
gagagatctc aaggacggtg actgcag    27

<210> SEQ ID NO 10
<211> LENGTH: 86
<212> TYPE: DNA
<213> ORGANISM: Artificial Sequence
<220> FEATURE:
<223> OTHER INFORMATION: Artificial Nucleotide Sequence

```
<400> SEQUENCE: 10
tctcctcgag gccaccatgg ggagtagcaa gagcaagcct aaggacccca gccagcgccg      60
gatgacagaa tacaagcttg tggtgg                                           86

<210> SEQ ID NO 11
<211> LENGTH: 33
<212> TYPE: DNA
<213> ORGANISM: Artificial Sequence
<220> FEATURE:
<223> OTHER INFORMATION: Artificial Antisense Nucleotide Sequence

<400> SEQUENCE: 11
cacatctaga tcaggacagc acagacttgc agc                                   33

<210> SEQ ID NO 12
<211> LENGTH: 41
<212> TYPE: DNA
<213> ORGANISM: Artificial Sequence
<220> FEATURE:
<223> OTHER INFORMATION: Artificial Nucleotide Sequence

<400> SEQUENCE: 12
tctcctcgag gccaccatga cagaatacaa gcttgtggtg g                          41

<210> SEQ ID NO 13
<211> LENGTH: 38
<212> TYPE: DNA
<213> ORGANISM: Artificial Sequence
<220> FEATURE:
<223> OTHER INFORMATION: Artificial Antisense Nucleotide Sequence

<400> SEQUENCE: 13
cactctagac tggtgtcaga gcagcacaca cttgcagc                              38

<210> SEQ ID NO 14
<211> LENGTH: 38
<212> TYPE: DNA
<213> ORGANISM: Artificial Sequence
<220> FEATURE:
<223> OTHER INFORMATION: Artificial Nucleotide Sequence

<400> SEQUENCE: 14
gagagaattc gccaccatga cggaatataa gctggtgg                              38

<210> SEQ ID NO 15
<211> LENGTH: 33
<212> TYPE: DNA
<213> ORGANISM: Artificial Sequence
<220> FEATURE:
<223> OTHER INFORMATION: ArtificialAntisense Nucleotide Sequence

<400> SEQUENCE: 15
gagagtcgac gcgtcaggag agcacacact tgc                                   33

<210> SEQ ID NO 16
<211> LENGTH: 22
<212> TYPE: DNA
<213> ORGANISM: Artificial Sequence
<220> FEATURE:
<223> OTHER INFORMATION: Artificial Nucleotide Sequence

<400> SEQUENCE: 16
ccgccggcct ggaggagtac ag                                               22
```

<210> SEQ ID NO 17
<211> LENGTH: 38
<212> TYPE: DNA
<213> ORGANISM: Artificial Sequence
<220> FEATURE:
<223> OTHER INFORMATION: Artificial Nucleotide Sequence

<400> SEQUENCE: 17
gagagaattc gccaccatga ctgagtacaa actggtgg         38

<210> SEQ ID NO 18
<211> LENGTH: 32
<212> TYPE: DNA
<213> ORGANISM: Artificial Sequence
<220> FEATURE:
<223> OTHER INFORMATION: Artificial Antisense Nucleotide Sequence

<400> SEQUENCE: 18
gagagtcgac ttgttacatc accacacatg gc         32

<210> SEQ ID NO 19
<211> LENGTH: 21
<212> TYPE: DNA
<213> ORGANISM: Artificial Sequence
<220> FEATURE:
<223> OTHER INFORMATION: Artificial Nucleotide Sequence

<400> SEQUENCE: 19
gttggagcag ttggtgttgg g         21

<210> SEQ ID NO 20
<211> LENGTH: 38
<212> TYPE: DNA
<213> ORGANISM: Artificial Sequence
<220> FEATURE:
<223> OTHER INFORMATION: Artificial Antisense Nucleotide Sequence

<400> SEQUENCE: 20
gagaggtacc gccaccatga ctgaatataa acttgtgg         38

<210> SEQ ID NO 21
<211> LENGTH: 36
<212> TYPE: DNA
<213> ORGANISM: Artificial Sequence
<220> FEATURE:
<223> OTHER INFORMATION: Artificial Nucleotide Sequence

<400> SEQUENCE: 21
ctctgtcgac gtatttacat aattacacac tttgtc         36

<210> SEQ ID NO 22
<211> LENGTH: 24
<212> TYPE: DNA
<213> ORGANISM: Artificial Sequence
<220> FEATURE:
<223> OTHER INFORMATION: Artificial Nucleotide Sequence

<400> SEQUENCE: 22
gtagttggag ctgttggcgt aggc         24

<210> SEQ ID NO 23
<211> LENGTH: 38
<212> TYPE: DNA
<213> ORGANISM: Artificial Sequence
<220> FEATURE:
<223> OTHER INFORMATION: Artificial Nucleotide Sequence

```
-continued

<400> SEQUENCE: 23
gagaggtacc gccaccatga ctgaatataa acttgtgg                              38

<210> SEQ ID NO 24
<211> LENGTH: 45
<212> TYPE: DNA
<213> ORGANISM: Artificial Sequence
<220> FEATURE:
<223> OTHER INFORMATION: Artificial Antisense Nucleotide Sequence

<400> SEQUENCE: 24
ctctgtcgac agattacatt ataatgcatt ttttaatttt cacac                      45

<210> SEQ ID NO 25
<211> LENGTH: 24
<212> TYPE: DNA
<213> ORGANISM: Artificial Sequence
<220> FEATURE:
<223> OTHER INFORMATION: Artificial Nucleotide Sequence

<400> SEQUENCE: 25
gtagttggag ctgttggcgt aggc                                             24
```

US 6,534,506 B2

INHIBITORS OF PRENYL-PROTEIN TRANSFERASE

RELATED APPLICATION

The present patent application claims the benefit of co-pending provisional application Ser. No. 60/195,951, filed Apr. 10, 2000.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase type I, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W.R. Schafer and J. Rine, *Ann. Rev. Genetics* 30:209–237 (1992)). The term prenyl-protein transferase may be used to refer generally to farnesyl-protein transferase and geranylgeranyl-protein transferase type I. The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are famesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of famesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the famesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that famesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit prenyl-protein transferase and thus, the post-translational prenylation of proteins. It is a further object of this invention to develop chemotherapeutic compositions containing the compounds of this invention and methods for producing the compounds of this invention.

SUMMARY OF THE INVENTION

The present invention comprises peptidomimetic piperazine-containing macrocyclic compounds that further comprise a bicyclic imidazolyl moiety and that inhibit prenyl-protein transferase. Further contained in this invention are chemotherapeutic compositions containing these prenyl-protein transferase inhibitors and methods for their production.

The compounds of this invention are illustrated by the formula A:

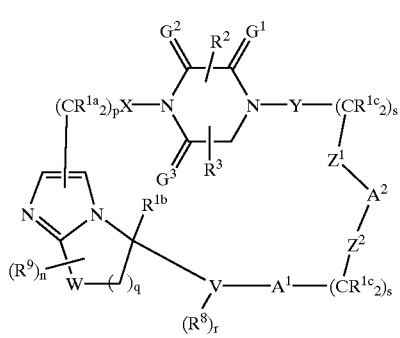

A

DETAILED DESCRIPTION OF THE INVENTION

The compounds of this invention are useful in the inhibition of prenyl-protein transferase and the prenylation of the oncogene protein Ras. In a first embodiment of this invention, the inhibitors of prenyl-protein transferase are illustrated by the formula A:

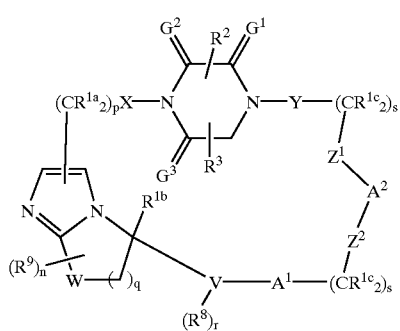

A wherein:
$R^{1a}$ and $R^{1c}$ are independently selected from:
  a) hydrogen,
  b) aryl, heterocycle, $C_3-C_{10}$ cycloalkyl, $R^{10}O-$, $R^{11}S(O)_m-$, $R^{10}C(O)NR^{10}-$, $(R^{10})_2N-C(O)-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$,
  c) unsubstituted or substituted $C_{1-C6}$ alkyl, unsubstituted or substituted $C_2-C_6$ alkenyl or unsubstituted or substituted $C_2-C_6$ alkynyl, wherein the substituent on the substituted $C_1-C_6$ alkyl, substituted $C_2-C_6$ alkenyl or substituted $C_2-C_6$ alkynyl is selected from unsubstituted or substituted aryl, heterocyclic, $C_3-C_{10}$ cycloalkyl, $C_2-C_6$ alkenyl, $C_2-C_6$ alkynyl, $R^{10}O-$, $R^{11}S(O)_m-$, $R^{10}C(O)NR^{10}-$, $(R^{10})_2N-C(O)-$, CN, $(R^{10})_2N-C(NR^{10})-$, $R^{10}C(O)-$, $R^{10}C(O)-$, $-N(R^{10})_2$, and $R^{11}OC(O)-NR^{10}-$,
or two $R^{1a}$s or two $R^{1c}$s on the same carbon atom may be combined to form $-(CH_2)_t-$;
$R^{1b}$ is selected from:
  a) hydrogen,
  b) aryl, heterocycle, $C_3-C_{10}$ cycloalkyl, $(R^{10})_2N-C(O)-$, $(R^{10})_2N-C(NR^{10})-$, $R^{10}C(O)-$ or $R^{10}OC(O)-$, and c) unsubstituted or substituted $C_1-C_6$ alkyl, unsubstituted or substituted $C_2-C_6$ alkenyl or unsubstituted or substituted $C_2-C_6$ alkynyl, wherein the substituent on the substituted $C_1-C_6$ alkyl, substituted $C_2-C_6$ alkenyl or substituted $C_2-C_6$ alkynyl is selected from unsubstituted or substituted aryl, heterocyclic, $C_3-C_{10}$ cycloalkyl, $C_2-C_6$ alkenyl, $C_2-C_6$ alkynyl, one or more fluorines, $R^{10}O-$, $R^{11}S(O)_m-$, $R^{10}C(O)NR^{10}-$, $(R^{10})_2N-C(O)-$, CN, $(R^{10})_2N-C(NR^{10})-$, $R^{10}C(O)-$, $R^{10}OC(O)-$, $-N(R^{10})_2$, and $R^{11}OC(O)-NR^{10}-$;

$R^2$ and $R^3$ are independently selected from H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

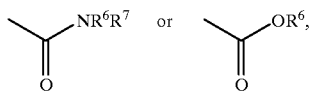

wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) CN,
2) $C_{3-6}$ cycloalkyl,
3) $OR^6$,
4) $SR^4$, $S(O)R^4$, $SO_2R^4$,
5) 
   $-NR^6R^7$,
6) 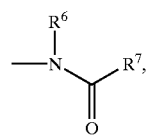
7) 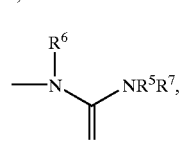
8) 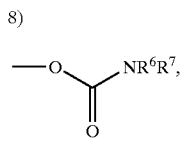
9) 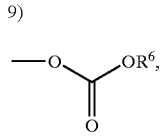

-continued

10)

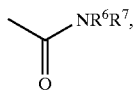

11)

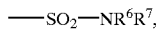

12)

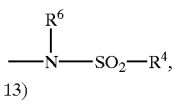

13)

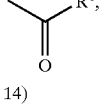

14)

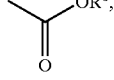

15) N₃, or

16) F; or $R^2$ and $R^3$ are attached to the same carbon atom and are combined to form —(CH$_2$)$_u$— wherein one of the carbon atoms is optionally replaced by a moiety selected from O, S(O)$_m$, —NC(O)—, and —N(COR$^{10}$)—; and $R^4$ is selected from C$_{1-4}$ alkyl, C$_{3-6}$ cycloalkyl, heterocycle, aryl, unsubstituted or substituted with:
  a) C$_{1-4}$ alkoxy,
  b) aryl or heterocycle,
  c) halogen,
  d) HO, e)

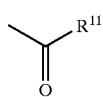

f)

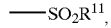

g) N(R$^{10}$)$_2$, or
  h) one or more fluorines;

$R^5$, $R^6$ and $R^7$ are independently selected from:
  1) hydrogen,
  2) R$^{10}$C(O)—, or R$^{10}$OC(O)—, and
  3) C$_1$–C$_6$ alkyl, C$_2$–C$_6$ alkenyl, C$_2$–C$_6$ alkynyl, C$_{3-6}$ cycloalkyl, heterocycle, aryl, aroyl, heteroaroyl, arylsulfonyl, heteroarylsulfonyl, unsubstituted or substituted with one or more substituents selected from:
    a) R$^{10}$O—,
    b) aryl or heterocycle,
    c) halogen,
    d) R$^{10}$C(O)NR$^{10}$—, e)

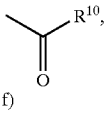

f)

g) N(R$^{10}$)$_2$,
  h) C$_{3-6}$ cycloalkyl,
  i) C$_1$–C$_6$ perfluoroalkyl,
  j) (R$^{10}$)$_2$N—C(NR$^{10}$)—,
  k) R$^{10}$OC(O)—,
  l) R$^{11}$OC(O)NR$^{10}$—,
  m) CN, and
  n) NO$_2$; or $R^6$ and $R^7$ may be joined in a ring; and independently, $R^5$ and $R^7$ may be joined in a ring;

$R^8$ is independently selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, C$_1$–C$_6$ perfluoroalkyl, F, Cl, Br, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, —N(R$^{10}$)$_2$, or R$^{11}$OC(O)NR$^{10}$—, and
  c) C$_1$–C$_6$ alkyl unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, C$_1$–C$_6$ perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, —N(R$^{10}$)$_2$, or R$^{10}$OC(O)NH—;

$R^9$ is selected from:
  a) hydrogen,
  b) C$_2$–C$_6$ alkenyl, C$_2$–C$_6$ alkynyl, C$_1$–C$_6$ perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, —N(R$^{10}$)$_2$, or R$^{11}$OC(O)NR$^{10}$—, and
  c) C$_1$–C$_6$ alkyl unsubstituted or substituted by C$_1$–C$_6$ perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, R$^{10}$OC(O)—, —N(R$^{10}$)$_2$, or R$^{11}$OC(O)NR$^{10}$—;

$R^{10}$ is independently selected from hydrogen, C$_1$–C$_6$ alkyl, Cl-C$_6$ alkyl substituted with one or more fluorines, benzyl, unsubstituted or substituted aryl and unsubstituted or substituted heterocycle;

$R^{11}$ is independently selected from C$_1$–C$_6$ alkyl, C$_1$–C$_6$ alkyl substituted with one or more fluorines, unsubstituted or substituted aryl and unsubstituted or substituted heterocycle;

$R^{12}$ is independently selected from hydrogen, C$_1$–C$_6$ alkyl, C$_1$–C$_6$ alkyl substituted with one or more fluorines, unsubstituted or substituted benzyl, unsubstituted or substituted aryl, unsubstituted or substituted heterocycle, and C$_1$–C$_6$ alkyl substituted with unsubstituted or substituted aryl or unsubstituted or substituted heterocycle;

$A^1$ is selected from a bond, —C(O)—, —C(O)NR$^{10}$—, —NR$^{10}$C(O)—, O, —N(R$^{10}$)—, —S(O)$_2$N(R$^{10}$), —N(R$^{10}$)S(O)$_2$—, —NR$^{10}$C(O)NR$^{10}$— and S(O)$_m$;

$A^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, —NR$^{10}$C(O)NR$^{10}$—, S(O)$_m$ and —C(R$^{1c}$)$_2$—;

$G^1$, $G^2$ and $G^3$ are independently selected from (R$^2$,R$^3$) and O;

V is selected from:
a) heterocycle, and
b) aryl;

W is S(O)$_m$, O or CH$_2$;

X is selected from: a bond, —C(O)—, —NR$^{10}$C(O)—, —N(R$^{10}$)S(O)$_2$— and S(O)$_2$;

Y is selected from a bond, —C(O)—, —C(O)NR$^{10}$—, —C(O)O— and —S(O)$_m$;

$Z^1$ is selected from unsubstituted or substituted aryl and unsubstituted or substituted heterocycle, wherein the substituted aryl or substituted heterocycle is substituted with one or more of:
1) C$_{1-8}$ alkyl, C$_{2-8}$ alkenyl or C$_{2-8}$ alkynyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$,
   g) —C(O)NR$^6$R$^7$, or
   h) one or more fluorines;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$;
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;

$Z^2$ is selected from a bond, unsubstituted or substituted aryl and unsubstituted or substituted heterocycle, wherein the substituted aryl or substituted heterocycle is substituted with one or more of:
1) C$_{1-8}$ alkyl, C$_{2-8}$ alkenyl or C$_{2-8}$ alkynyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$,
   g) —C(O)NR$^6$R$^7$, or
   h) one or more fluorines;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$;
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;

m is independently 0, 1 or 2;

n is 1 or 2;

p is independently 0, 1, 2, 3 or 4;

q is 1 or 2;

r is 0 to 5;

s is independently 0, 1, 2, 3 or 4;

t is 2, 3, 4, 5 or 6; and u is 2, 3, 4 or 5;

or a pharmaceutically acceptable salt or stereoisomer thereof.

In a second embodiment of this invention, the inhibitors of prenyl-protein transferase are illustrated by the formula B:

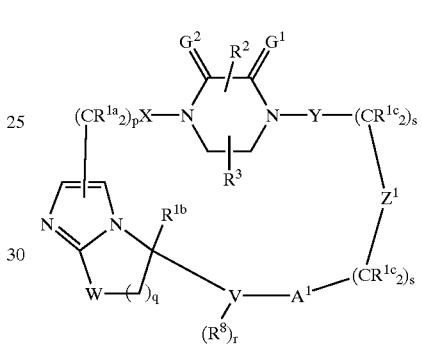

B wherein:

R$^{1a}$ and R$^{1c}$ are independently selected from:
a) hydrogen,
b) R$^{10}$O—, —N(R$^{10}$)$_2$, R$^{10}$C(O)NR$^{10}$—, R$^{11}$OC(O)O— or R$^{11}$OC(O)NR$^{10}$—, and
c) C$_1$–C$_6$ alkyl, unsubstituted or substituted by R$^{10}$O—, —N(R$^{10}$)$_2$, R$^{10}$C(O)NR$^{10}$—, R$^{11}$OC(O)O—, R$^{11}$OC(O)NR$^{10}$— or R$^{11}$S(O)$_m$—;

R$^{1b}$ is selected from:
a) hydrogen, and
b) unsubstituted or substituted C$_1$–C$_6$ alkyl, wherein the substituent on the substituted C$_1$–C$_6$ alkyl is selected from one or more fluorines, R$^{10}$O—, R$^{11}$S(O)$_m$—, R$^{10}$C(O)NR$^{10}$—, R$^{10}$OC(O)O— and R$^{11}$OC(O)—NR$^{10}$—;

R$^3$ is selected from H and CH$_3$;

R$^2$ is selected from H;

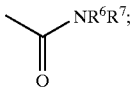

and C$_{1-5}$ alkyl, unbranched or branched, unsubstituted or substituted with one or more of:
1) aryl,
2) heterocycle,
3) OR$^6$,
4) SR$^4$, SO$_2$R$^4$, or

5)

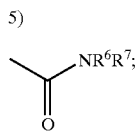

and any two of $R^2$ and $R^3$ are optionally attached to the same carbon atom;

$R^4$ is selected from:
- $C_{1-4}$ alkyl and $C_{3-6}$ cycloalkyl, unsubstituted or substituted with:
  - a) $C_{1-4}$ alkoxy,
  - b) one or more fluorines, or
  - c) aryl or heterocycle;

$R^6$ and $R^7$ are independently selected from H; $C_{1-6}$ alkyl, $C_{3-6}$ cycloalkyl, heterocycle, aryl, aroyl, heteroaroyl, arylsulfonyl, heteroarylsulfonyl, unsubstituted or substituted with one or two:
- a) $C_{1-4}$ alkoxy,
- b) aryl or heterocycle,
- c) halogen,
- d) HO, e)

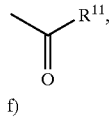

f)

—SO$_2$R$^{11}$,

- g) $N(R^{10})_2$, or
- h) $C_{3-6}$ cycloalkyl;

$R^8$ is independently selected from:
- a) hydrogen,
- b) unsubstituted or substituted aryl, $C_1$-$C_6$ alkyl, $C_2$-$C_6$ alkenyl, $C_2$-$C_6$ alkynyl, $C_1$-$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{10}C(O)NR^{10}$—, and
- c) $C_1$-$C_6$ alkyl substituted by: unsubstituted or substituted aryl, $C_1$-$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$-$C_6$ alkyl, $C_1$-$C_6$ alkyl substituted with one or more fluorines, benzyl and unsubstituted or substituted aryl;

$R^{11}$ is independently selected from $C_1$-$C_6$ alkyl, $C_1$-$C_6$ alkyl substituted with one or more fluorines, and unsubstituted or substituted aryl;

$R^{12}$ is independently selected from hydrogen, $C_1$-$C_6$ alkyl, unsubstituted or substituted benzyl, unsubstituted or substituted aryl, unsubstituted or substituted heterocycle, and $C_1$-$C_6$ alkyl substituted with one or more fluorines, unsubstituted or substituted aryl or unsubstituted or substituted heterocycle;

$A^1$ is selected from a bond, O, —$N(R^{10})$— and $S(O)_m$;
$G^1$ and $G^2$ are independently selected from $(R^2, R^3)$ and O;

V is selected from:
- a) heterocycle selected from pyridinyl, pyridonyl, 2-oxopiperidinyl, indolyl, quinolinyl and isoquinolinyl, and
- b) aryl;

W is S or $CH_2$;
X is selected from a bond, —C(O)— or —$S(O)_m$;
Y is selected from a bond, —C(O)—, —$C(O)NR^{10}$—, —C(O)O— and —$S(O)_m$;
$Z^1$ is selected from unsubstituted or substituted aryl or unsubstituted or substituted heterocycle, wherein the substituted aryl or substituted heterocycle is independently substituted with one or two of:
1) $C_{1-8}$ alkyl, $C_{2-8}$ alkenyl or $C_{2-8}$ alkynyl, unsubstituted or substituted with:
   - a) $C_{1-4}$alkoxy,
   - b) $NR^6R^7$,
   - c) $C_{3-6}$ cycloalkyl,
   - d) aryl or heterocycle,
   - e) HO,
   - f) —$S(O)_mR^4$,
   - g) —$C(O)NR^6R^7$, or
   - h) one or more fluorines;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) —$S(O)_mR^4$,
10) —$OS(O)_2R^4$,
11) —$C(O)NR^6R^7$,
12) —$C(O)OR^6$, or
13) $C_3$-$C_6$ cycloalkyl;

m is 0, 1 or 2;
n is 0, 1 or 2;
p is 0, 1, 2, 3 or 4;
q is 1 or 2;
r is 0 to 5; and
s is independently 0, 1, 2 or 3;

or a pharmaceutically acceptable salt or stereoisomer thereof.

Another preferred embodiment of the compounds of this invention is illustrated by the formula C:

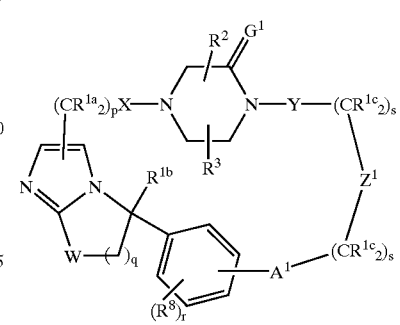

C wherein:
$R^{1a}$ and $R^{1c}$ are independently selected from:
- a) hydrogen,
- b) $R^{10}O$—, —$N(R^{10})_2$, $R^{10}C(O)NR^{10}$—, $R^{11}OC(O)O$— or $R^{11}OC(O)NR^{10}$—, and
- c) $C_1$-$C_6$ alkyl, unsubstituted or substituted by $R^{10}O$—, —$N(R^{10})_2$, $R^{10}C(O)NR^{10}$—, $R^{11}OC(O)O$—, $R^{10}OC(O)NR^{10}$— or $R^{11}S(O)_m$—;

$R^{1b}$ is selected from:
a) hydrogen, and
b) unsubstituted or substituted $C_1-C_6$ alkyl, wherein the substituent on the substituted $C_1-C_6$ alkyl is selected from one or more fluorines, $R^{10}O-$, $R^{11}S(O)_m-$, $R^{10}C(O)NR^{10}-$, $R^{10}OC(O)O-$ and $R^{11}OC(O)-$ $R^3$ is selected from H and $CH_3$;

$R^2$ is selected from H;

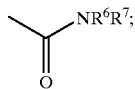

and $C_{1-5}$ alkyl, unbranched or branched, unsubstituted or substituted with one or more of:
1) aryl,
2) heterocycle,
3) $OR^6$,
4) $SR^4$, $SO_2R^4$, or

5)

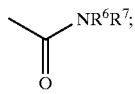

and any two of $R^2$ and $R^3$ are optionally attached to the same carbon atom;

$R^4$ is selected from:
$C_{1-4}$ alkyl and $C_{3-6}$ cycloalkyl, unsubstituted or substituted with:
a) $C_{1-4}$ alkoxy,
b) one or more fluorines, or
c) aryl or heterocycle;

$R^6$ and $R^7$ are independently selected from H; $C_{1-6}$ alkyl, $C_{3-6}$ cycloalkyl, heterocycle, aryl, aroyl, heteroaroyl, arylsulfonyl, heteroarylsulfonyl, unsubstituted or substituted with one or two:
a) $C_{1-4}$ alkoxy,
b) aryl or heterocycle,
c) halogen,
d) HO, e)

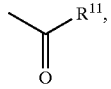

f)

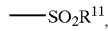

g) $N(R^{10})_2$, or
h) $C_{3-6}$ cycloalkyl;

$R^8$ is independently selected from:
a) hydrogen,
b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{12}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by: unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1-C_6$ alkyl, $C_1-C_6$ alkyl substituted with one or more fluorines, benzyl and unsubstituted or substituted aryl;

$R^{11}$ is independently selected from $C_1-C_6$ alkyl, $C_1-C_6$ alkyl substituted with one or more fluorines and unsubstituted or substituted aryl;

$R^{12}$ is independently selected from hydrogen, $C_1-C_6$ alkyl, unsubstituted or substituted benzyl, unsubstituted or substituted aryl, unsubstituted or substituted heterocycle, and $C_1-C_6$ alkyl substituted with one or more fluorines, unsubstituted or substituted aryl or unsubstituted or substituted heterocycle;

$A^1$ is selected from a bond, O, $-N(R^{10})-$ and $S(O)_m$;

$G^1$ is selected from $(R^2,R^3)$ and O;

W is S or $CH_2$;

X is selected from a bond, $-C(O)-$ or $-S(O)_m$;

Y is selected from a bond, $-C(O)-$, $-C(O)NR^{10}-$, $-C(O)O-$, or $-S(O)_m$;

$Z^1$ is selected from unsubstituted or substituted aryl or unsubstituted or substituted heterocycle, wherein the substituted aryl or substituted heterocycle is independently substituted with one or two of:
1) $C_{1-8}$ alkyl, $C_{2-8}$ alkenyl or $C_{2-8}$ alkynyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) $-S(O)_mR^4$,
g) $-C(O)NR^6R^7$, or
h) one or more fluorines;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) $-S(O)_mR^4$,
10) $-OS(O)_2R^4$,
11) $-C(O)NR^6R^7$,
12) $-C(O)OR^6$, or
13) $C_3-C_6$ cycloalkyl;

m is 0, 1 or 2;
n is 0, 1 or 2;
p is 0, 1, 2, 3 or 4;
q is 1 or 2;
r is 0 to 5; and
s is independently 0, 1, 2 or 3;
or a pharmaceutically acceptable salt or stereoisomer thereof.

Specific examples of the compounds of the instant invention include the following:

(R)-15-Bromo-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile (S)-15-Bromo-19,20-dihydro-19,22-dioxo-28-thia-5H,17H-3,5:18,21 -diethano-6,10:12,16-dimetheno-22H-imidazo[3,4-h][1,8,11,14]oxatriazacycloeicosine-9-carbonitrile (R)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile (S)-15-Chloro-19,20-dihydro-19,22-dioxo-5H,17H-3,5:18,
21-diethano-6,10:12,16-dimetheno-22H-imidazo[3,4-h]
[1,8,11,14]oxatriazacycloeicosine-9-carbonitrile 15-Chloro-19,20-dihydro-19-oxo-5H,17H-3,5:18,21-
diethano-6,10:12,16-dimetheno-22H-imidazo[3,4-h][1,8,
11,14]oxatriazacycloeicosine-9-carbonitrile 19,20-Dihydro-19,22-dioxo-5H-3,5:18,21-diethano-12,14-
etheno-6,10-metheno-benzo[d]imidazo[4,3-k][1,6,9,12]
oxatriazacyclooctadecine-9-carbonitrile 22,23-Dihydro-22-oxo-31-thia-5H-3,5:21,24-diethano-6,
10:12,16-dimetheno-12H, 25H-benzo[g]imidazo[4,3-n]
[1,8,11,14]oxatriazacycloheneicosine-9-carbonitrile.

15-Fluoro-19,20-dihydro-19,22-dioxo-28-5H,17H-3,5:18,
21-diethano-6,10:12,16-dimetheno-22H-imidazo[3,4-h]
[1,8,11,14]oxatriazacycloeicosine-9-carbonitrile (R)-15-Chloro-19,20-dihydro-19,22-dioxo-28-thia-5H,
17H-3,5:18,21-diethano-6,10:12,16-dimetheno-22H-
imidazo[3,4-h][1,8,11,14]oxatriazacycloeicosine-9-
carbonitrile (S)-15-Chloro-19,20-dihydro-19,22-dioxo-28-thia-5H,17H-
3,5:18,21-diethano-6,10:12,16-dimetheno-22H-imidazo
[3,4-h][1,8,11,14]oxatriazacycloeicosine-9-carbonitrile 19,20-Dihydro-19-oxo-30-thia-5H-3,5:18,21-diethano-12,
14-etheno-6,10-metheno-benzo[d]imidazo[4,3–1][1,6,9,
13]oxatriazacyclononadecine-9-carbonitrile (R)-19,20-Dihydro-19-oxo-30-thia-5H-3,5:18,21-diethano-
12,14-etheno-6,10-metheno-benzo[d]imidazo[4,3-1][1,6,
9,13]oxatriazacyclononadecine-9-carbonitrile (S)-19,20-Dihydro-19-oxo-30-thia-5H-3,5:18,21-diethano-
12,14-etheno-6,10-metheno-benzo[d]imidazo[4,3-1][1,6,
9,13]oxatriazacyclononadecine-9-carbonitrile or a pharmaceutically acceptable salt or stereoisomer
thereof.

Preferred examples of compounds of the instant invention
include:

(R)-15-Bromo-19,20-dihydro-19,22-dioxo-28-thia-5H,
17H-3,5:18,21-diethano-6,10:12,16-dimetheno-22H-
imidazo[3,4-h][1,8,11,14]oxatriazacycloeicosine-9-
carbonitrile hydrochloride (S)-15-Bromo-19,20-dihydro-19,22-dioxo-28-thia-5H,17H-
3,5:18,21-diethano-6,10:12,16-dimetheno-22H-imidazo
[3,4-h][1,8,11,14]oxatriazacycloeicosine-9-carbonitrile
hydrochloride

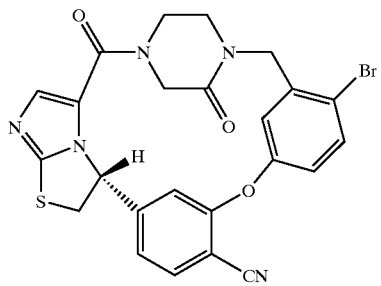

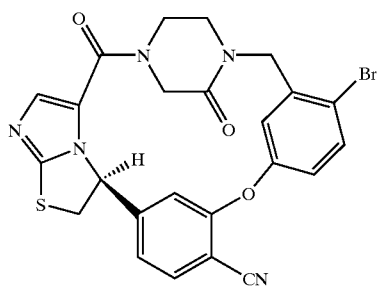

(R)-15-Chloro-19,20-dihydro-19,22-dioxo-5H,17H-3,5:18,
21-diethano-6,10:12,16-dimetheno-22H-imidazo[3,4-h]
[1,8,11,14]oxatriazacycloeicosine-9-carbonitrile hydro-
chloride

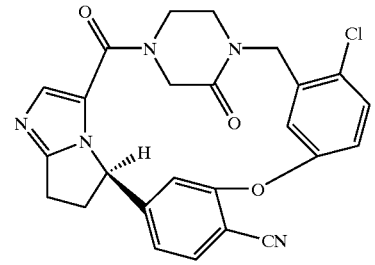

(S)-15-Chloro-19,20-dihydro-19,22-dioxo-5H,17H-3,5:18,
21-diethano-6,10:12,16-dimetheno-22H-imidazo[3,4-h]
[1,8,11,14]oxatriazacycloeicosine-9-carbonitrile hydro-
chloride

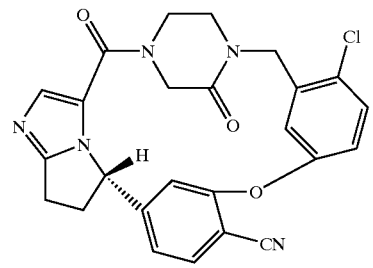

(R)-15-Chloro-19,20-dihydro-19,22-dioxo-28-thia-5H,
17H-3,5:18,21-diethano-6,10:12,16-dimetheno-22H-
imidazo[3,4-h][1,8,11,14]oxatriazacycloeicosine-9-
carbonitrite

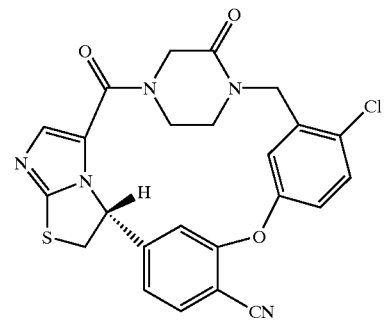

(S)-15-Chloro-19,20-dihydro-19,22-dioxo-28-thia-5H,17H-
3,5:18,21-diethano-6,10:12,16-dimetheno-22H-imidazo
[3,4-h][1,8,11,14]oxatriazacycloeicosine-9-carbonitrile

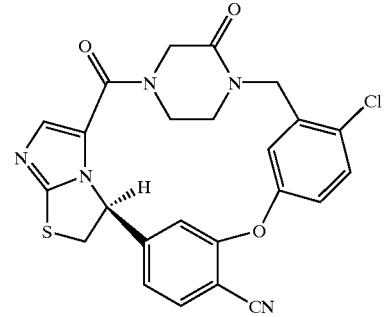

(R)-19,20-Dihydro-19-oxo-30-thia-5H-3,5:18,21-diethano-12,14-etheno-6,10-metheno-benzo[d]imidazo[4,3-1][1,6,9,13]oxatriazacyclononadecine-9-carbonitrile

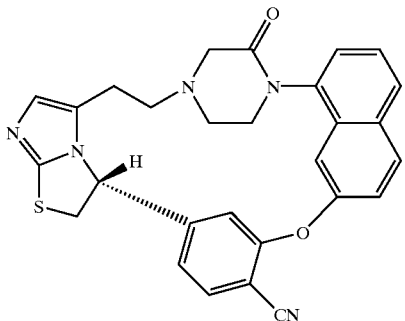

(S)-19,20-Dihydro-19-oxo-30-thia-5H-3,5:18,21-diethano-12,14-etheno-6,10-metheno-benzo[d]imidazo[4,3-1][1,6,9,13]oxatriazacyclononadecine-9-carbonitrile

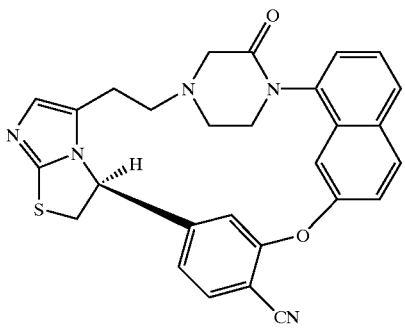

or a pharmaceutically acceptable salt or optical isomer thereof.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119–1190) When any variable (e.g. aryl, heterocycle, $R^{1a}$, $R^6$ etc.) occurs more than one time in any constituent, its definition on each occurrence is independent at every other occurrence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

Preferably, alkenyl is $C_2$–$C_6$ alkenyl.

Preferably, alkynyl is $C_2$–$C_6$ alkynyl.

As used herein, "cycloalkyl" is intended to include cyclic saturated aliphatic hydrocarbon groups having the specified number of carbon atoms. Preferably, cycloalkyl is $C_3$–$C_{10}$ cycloalkyl. Examples of such cycloalkyl elements include, but are not limited to, cyclopropyl, cyclobutyl, cyclopentyl, cyclohexyl and cycloheptyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothi opyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroarylsulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1$–$C_6$ alkyl$)_2$, $NO_2$, CN, $(C_1$–$C_6$ alkyl)O—, (aryl)O—, —OH, $(C_1$–$C_6$ alkyl)S$(O)_m$—, $(C_1$–$C_6$ alkyl)C(O)NH—, $H_2N$—C(NH)—, $(C_1$–$C_6$ alkyl)C(O)—, $(C_1$–$C_6$ alkyl)OC(O)—, $(C_1$–$C_6$ alkyl)OC(O)NH—, phenyl, pyridyl, imidazolyl, oxazolyl, isoxazolyl, thiazolyl, thienyl, furyl, isothiazolyl and $C_1$–$C_{20}$ alkyl.

As used herein in the definition of $R^2$ and $R^3$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substituent(s) $R^2$ and $R^3$ are selected.

As used herein, the term "one or more fluorines" describes substitution on one or more carbon atoms of a substituted group with one or more fluroine atoms. Preferably the substituted group which is substituted with one or more fluorines is substitued with one to five fluorines. Preferably a $C_1$–$C_6$ alkyl substituted with one or more fluorines is a $C_{1-6}$ alkyl substituted with one to five fluorines.

Preferably, as used herein in the definition of $R^6$ and $R^7$, the substituted $C_{1-6}$ alkyl, substituted $C_{2-6}$ alkenyl, substituted $C_{2-6}$ alkynyl, substituted $C_{3-6}$ cycloalkyl, substituted aroyl, substituted aryl, substituted heteroaroyl, substituted arylsulfonyl, substituted heteroarylsulfonyl and substituted heterocycle, include moieties containing from 1 to 3 substituents in addition to the point of attachment to the rest of the compound.

The moiety formed when, in the definition of $R^{1a}$ and $R^{1c}$, two $R^{1a}$s or two $R^{1c}$s, on the same carbon atom are combined to form —$(CH_2)_t$— is illustrated by the following:

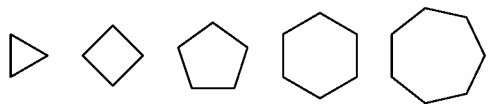

When $R^2$ and $R^3$ are combined to form —$(CH_2)_u$—, cyclic moieties are formed. Examples of such cyclic moieties include, but are not limited to:

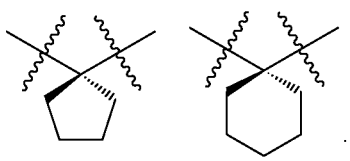

In addition, such cyclic moieties may optionally include a heteroatom(s). Examples of such heteroatom-containing cyclic moieties include, but are not limited to:

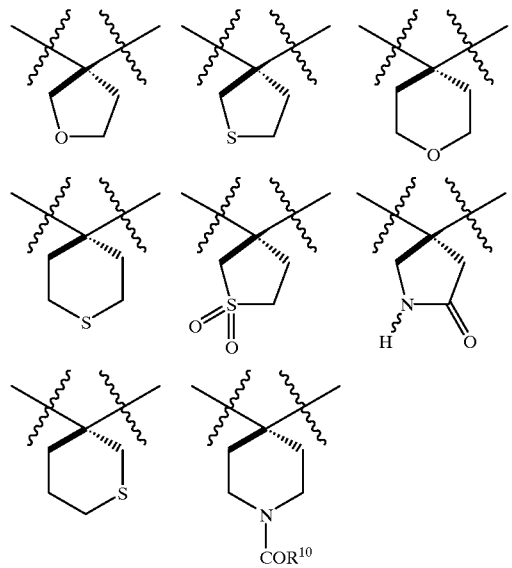

The moiety formed when, in the definition of $R^5$, $R^6$ and $R^7$, $R^6$ and $R^7$ or $R^5$ and $R^7$ are joined to form a ring, is illustrated by, but not limited to, the following:

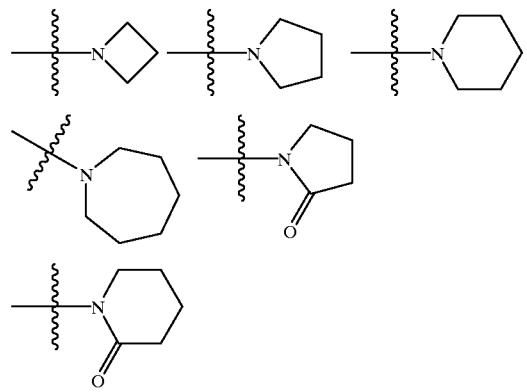

Lines drawn into the ring systems from substituents (such as from $R^2$, $R^3$, etc.) indicate that the indicated bond may be attached to any of the substitutable ring carbon or nitrogen atoms.

Preferably, $R^{1a}$ and $R^{1c}$ are independently selected from: hydrogen, —$N(R^{10})_2$, $R^{10}C(O)NR^{10}$— or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^{1b}$ is selected from:

a) hydrogen, and b) unsubstituted or substituted $C_1$–$C_6$ alkyl, wherein the substituent on the substituted $C_1$–$C_6$ alkyl is selected from one or more fluorines, $R^{10}O$—, $R^{11}S(O)_m$—, $R^{10}C(O)NR^{10}$—, $R^{10}OC(O)O$— and $R^{11}OC(O)$—$NR^{10}$—.

Preferably, R² is selected from H,

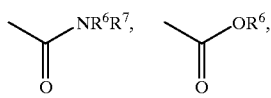

and an unsubstituted or substituted group, the group selected from $C_{1-8}$ alkyl, $C_{2-8}$ alkenyl and $C_{2-8}$ alkynyl;
  wherein the substituted group is substituted with one or more of:
  1) aryl or heterocycle, unsubstituted or substituted with:
    a) $C_{1-4}$ alkyl,
    b) $(CH_2)_p OR^6$,
    c) $(CH_2)_p NR^6 R^7$,
    d) halogen,
  2) $C_{3-6}$ cycloalkyl,
  3) $OR^6$,
  4) $SR^4$, $S(O)R^4$, $SO_2 R^4$, 5)
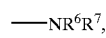

6)
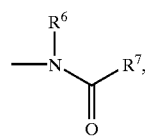

7)
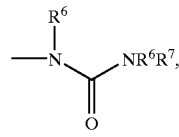

8)
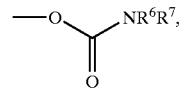

9)
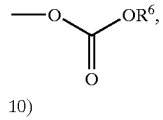

10)
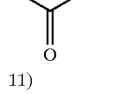

11)
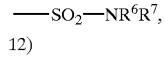

12)
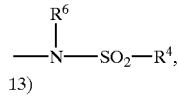

13)
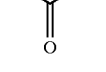

14)
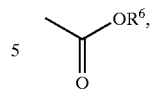

15) $N_3$, or

16) F.

Preferably, R³ is independently selected from: hydrogen and $C_1-C_6$ alkyl.

Preferably, R⁴ is unsubstituted or substituted $C_1-C_6$ alkyl, unsubstituted or substituted aryl and unsubstituted or substituted cycloalkyl.

Preferably, R⁵, R⁶ and R⁷ is selected from: hydrogen, unsubstituted or substituted $C_1-C_6$ alkyl, unsubstituted or substituted aryl and unsubstituted or substituted cycloalkyl.

Preferably, R¹⁰ is selected from H, $C_1-C_6$ alkyl and benzyl.

Preferably, A¹ is selected from a bond, O, —N(R¹⁰)— and $S(O)_m$.

Preferably, A² is selected from: a bond, —C(O)NR¹⁰—, —NR¹⁰C(O)—, O, —N(R¹⁰)—, —S(O)₂N(R¹⁰)—, S(=O)m and —N(R¹⁰)S(O)₂—.

Preferably, G¹ is O. Preferably, G² and G³ are (H₂).

Preferably, V is selected from heteroaryl and aryl. More preferably, V is phenyl or pyridyl.

Preferably, W is S or CH₂.

Preferably, X is selected from: a bond, —S(=O)$_m$·and —C(=O)—.

Preferably, Y is selected from: a bond, —S(=O)$_m$·and —C(=O)—.

Preferably, Z¹ and Z² are independently selected from unsubstituted or substituted phenyl, unsubstituted or substituted naphthyl, unsubstituted or substituted pyridyl, unsubstituted or substituted furanyl and unsubstituted or substituted thienyl. More preferably, Z¹ is selected from unsubstituted or substituted phenyl and unsubstituted or substituted naphthyl. More preferably, Z² is selected from a bond and unsubstituted or substituted phenyl.

Preferably, n is 0, 1, or 2.
Preferably, r is 1 or 2.
Preferably p is 1, 2 or 3.
Preferably q is 1.
Preferably s is 0 or 1.
Preferably, the moiety

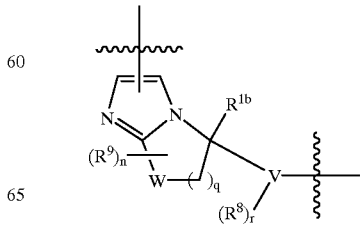

is selected from:

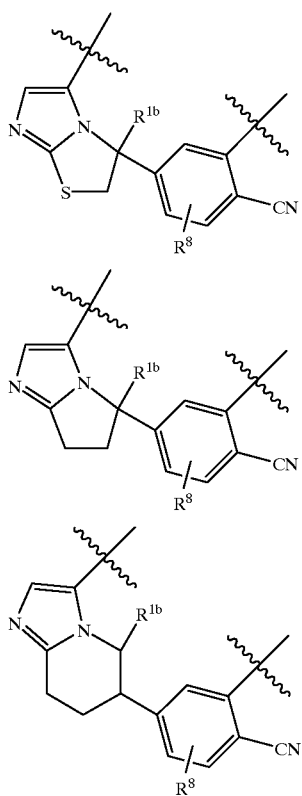

It is intended that the definition of any substituent or variable (e.g., $R^{1a}$, $R^9$, n, etc.) at a particular location in a molecule be independent of its definitions elsewhere in that molecule. Thus, —N($R^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–15, in addition to other standard manipulations such as ester hydrolysis, cleavage of protecting groups, etc., as may be known in the literature or exemplified in the experimental procedures. Substituents R, $R^a$, $R^b$, $R^{9'}$, $R^{9''}$, Z and $R^{sub}$, as shown in the Schemes, represent the substituents $R^2$, $R^3$, $R^9$ and Z, and substituents on Z, or their synthetic precursors; however their point of attachment to the ring is illustrative only and is not meant to be limiting. It is understood that one of ordinary skill in the art would be readily able to substitute commercially available or readily prepared suitably substituted aromatic moieties for those unsubstituted moieties illustrated in the schemes.

These reactions may be employed in a linear sequence to provide the compounds of the invention or they may be used to synthesize fragments that are subsequently joined by the alkylation reactions described in the Schemes.

Synopsis of Schemes 1–15

The requisite intermediates are in some cases commercially available, or can be prepared according to literature procedures or by synthetic methods known in the art. For instance, Scheme 1 illustrates the preparation of a suitably substituted phenyl-2,3-dihydro-imidazo[2,1-b]thiazole intermediate I. Thus, an aryl halide II is converted to the enol ether III via Stille reaction with an alkoxy vinyl stannane. The resulting vinyl ether III is hydrolyzed under acidic conditions to acetophenone IV, which is treated with bromine to provide the α-brominated product V. This bromoketone V is reacted with 2-thio imidazole VI under basic conditions, to give thio ether VII. Reduction of the ketone provides intermediate hydroxy imidazole VIII, where subsequent protection of the imidazole proceeds with di-tert-butyl dicarbonate to give IX. Conversion of the hydroxyl group of IX to the mesylate followed by heating gives cyclized product I, the product of intramolecular alkylation and subsequent deprotection during a standard aqueous workup. Ester group saponification gives carboxylic acid X. Alternatively, borohydride reduction followed by oxidation of the alcohol provides intermediate XI.

Scheme 2 describes the synthesis of a piperazinone intermediate. Halogenation of benzyloxybenzaldehyde XII with bromine, for example, gives benzaldehyde XIII where X=Br and the benzyl group has been cleaved. Reprotection of the phenol as silyl ether XIV and reduction of the aldehyde to the primary alcohol with sodium borohydride gives XV, which is converted to mesylate XVI. This mesylate is reacted with 4-t-butoxycarbonyl-2-piperazinone (prepared from commercially available starting materials by standard methods) under strongly basic conditions to afford the N-alkylated product XVII. Removal of the t-butoxycarbonyl protecting group gives piperazinone XVIII. Acid X is coupled to piperazinone XVIII under standard conditions, and a macrocyclization of the resulting intermediate XIX proceeds in the presence of fluoride ion to give the instant compound XX.

Scheme 3 illustrates incorporation of a suitably substituted piperazine in the compounds of the instant invention. Thus, the Boc-protected amino acids XXI, available commercially or by procedures known to those skilled in the art, can be coupled to N-benzyl amino acid esters using a variety of dehydrating agents such as DCC (dicyclohexycarbodiimide) or EDC.HCl (1-ethyl-3-(3-dimethylamino-propyl)carbodiimide hydrochloride) in a solvent such as methylene chloride, chloroform, dichloroethane, or in dimethylformamide. The product XXII is then deprotected with acid, for example hydrogen chloride in chloroform or ethyl acetate, or trifluoroacetic acid in methylene chloride, and cyclized under weakly basic conditions to give the diketopiperazine XXIII. Reduction of XXIII with lithium aluminum hydride in refluxing ether gives the piperazine XXIV, which may then be deprotected by catalytic reduction followed by silyl reprotection to provide intermediate XXV. Intermediate XXV may then be coupled to intermediate aldehyde XI, described above. Potassium fluoride mediated intramolecular cyclization of intermediate XXVI provides compound XXVII of the instant invention. This cyclization reaction depends on the presence of an electronic withdrawing moiety (such as nitro, cyano, and the like) either ortho or para to the fluorine atom. The cyclization product can then be deprotected to provide the compound of the instant invention.

Scheme 4 illustrates incorporation of a naphthyl moiety into the macrocyclic ring. Scheme 5 illustrates incorporation of a biphenyl ether into the macrocyclic ring.

Scheme 6 describes the synthesis of a compound of the invention which comprises a fused imidazolylcarbocycle moiety. Thus, a 1-benzyl-5-hydroxyethylimidazole XXVIII, prepared according to the general procedure outlined in Anthony et al., J. Med. Chem. 1999, 42, 3356–3368, is protected as the t-butyldimethylsilyl ether XXIX. Generation of the benzylic carbanion with a strong base such as lithium bis(trimethylsilyl)amide, and subsequent reaction with a suitable alkylating agent gives XXX. Deprotection of the t-butyldimethylsilyl ether gives primary alcohol XXXI, which is converted to aldehyde XXXII by a Swern oxidation. Aldehyde XXXII is subjected to reductive amination with piperazinone XXXIII, prepared as described in in Williams et al., J. Med. Chem. 1999, 42, 3779–3784. The remaining silyl ether of the reductive alkylation product XXXIV is removed, and the resulting primary alcohol oxidized to the aldehyde XXXV. A modified intramolecular Prins reaction yields the tetrahydroimidazo[1,2-a]pyridine or homolog XXXVI. Deoxygenation of thiocarbonate XXXVII with tri-n-butyltin hydride and 2,2'-azobisisobutyronitrile gives intermediate XXXVIII. Removal of the benzyl moiety by catalytic reduction, followed by cesium carbonate mediated cyclization provides the compound of the instant invention IXL.

Scheme 7 illustrates the preparation of a suitably substituted N-benzylpiperazine-2,5-dione and the incorporation of that group into the compounds of the instant invention. Scheme 8 illustrates preparation of the analogous compound of the instant invention which comprises a N-benzylpiperazine-2,3-dione.

Preparation of a piperazinone intermediate having specific substitution at the 3-position of the piperazinone group is illustrated in Scheme 9. Scheme 10 illustrates synthesis of a piperazine intermediate that comprises a spirocyclic carbocyclic moiety in the 2 position of the piperazine.

Scheme 11 illustrates the use of an optionally substituted homoserine lactone XL to prepare a Boc-protected piperazinone XLI. Intermediate XLI may be deprotected and reductively alkylated or acylated as illustrated in the previous Schemes. Alternatively, the hydroxyl moiety of intermediate XLI may be mesylated and displaced by a suitable nucleophile, such as the sodium salt of ethane thiol, to provide an intermediate XLII. Intermediate XLI may also be oxidized to provide the carboxylic acid on intermediate XLIII, which can be utilized form an ester or amide moiety.

Amino acids of the general formula XLIV which have a sidechain not found in natural amino acids may be prepared by the reactions illustrated in Scheme 12 starting with the readily prepared imine XLV.

Incorporation of a sulfur containing moiety for $A^1$ in the instant compounds is illustrated in Scheme 13. Thus chloroacetyl chloride is reacted with the tritylsulfide aniline XLVI to provide, after the previously described formation of the piperazinone ring, the intermediate XLVII. Intermediate XLVII may be reacted with the previously described aldehyde to provide intermediate XLVIII. Subsequent cyclization to form the fused ring, followed by removal of the hydroxy group as described above gives intermediate IL. Removal of the trityl protecting group liberates the mercaptan moiety, which undergoes cyclization under cesium carbonate conditions to provide the instant compound L. The sulfur may be oxidized to either the sulfone or sulfoxide LI.

Scheme 14 illustrates the synthetic strategy that is employed when the $R^8$ substituent is not an electronic withdrawing moiety either ortho or para to the fluorine atom. In the absence of the electronic withdrawing moiety, the intramolecular cyclization can be accomplished via an Ullmann reaction. Thus, a suitably substituted iodoacetophenone LII may be employed in place of intermediate IV to provide the intermediate LIII. The previously described elaboration of the intermediate LIII provides the aldehyde LIV. Aldehyde LIV is then used to reductively alkylate piperazinone LV to provide intermediate LVI. Desilylation followed by intramolecular cyclization under Ullmann conditions, provides the instant compound LVII.

Scheme 15 illustrate the preparation of intermediates LVIII and LIX which may be incorporated into synthetic reactions described above to provide compounds of the instant invention wherein W is oxygen (O).

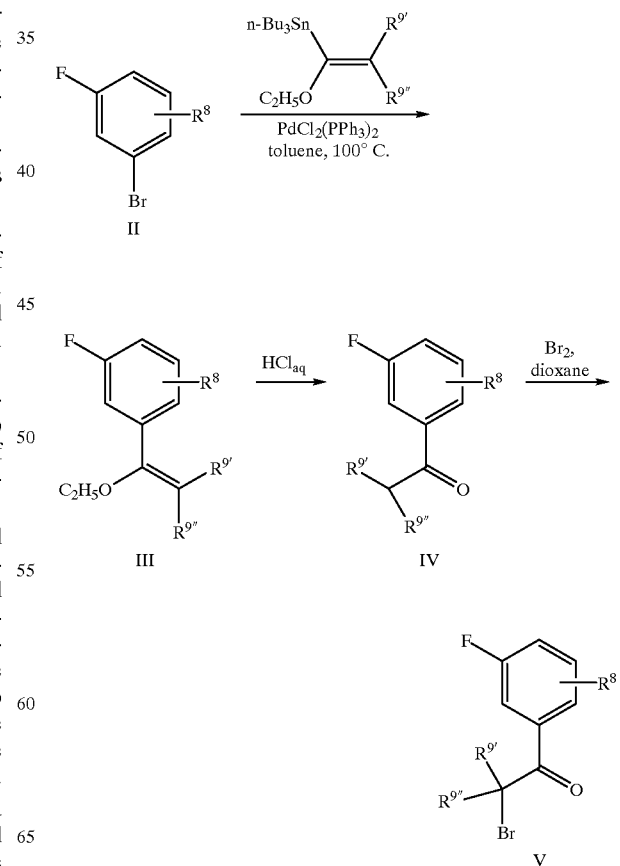

SCHEME 1

-continued
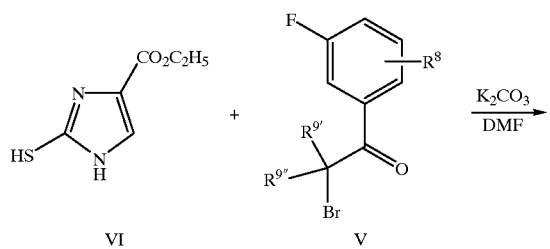
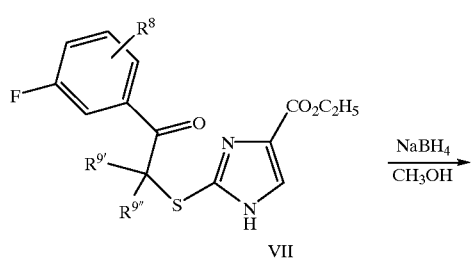
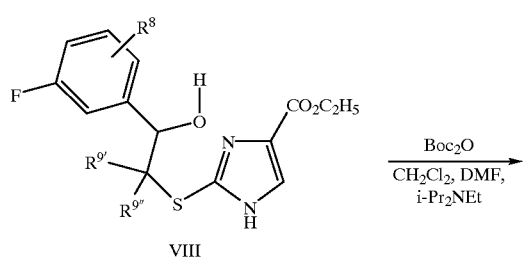
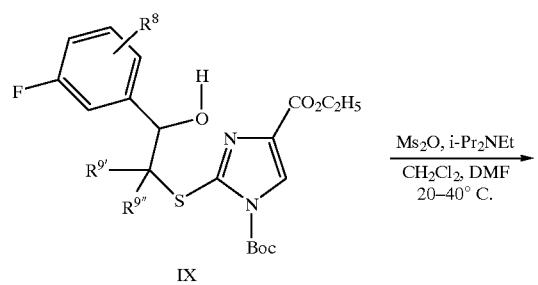
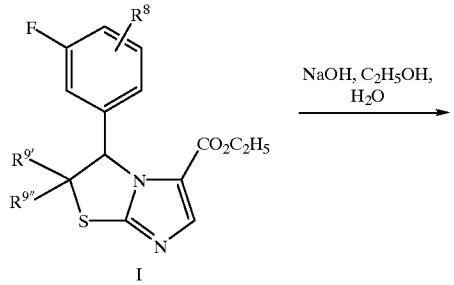
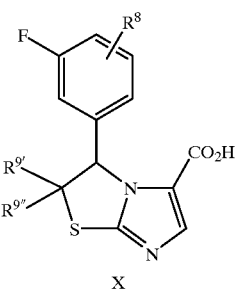
-continued
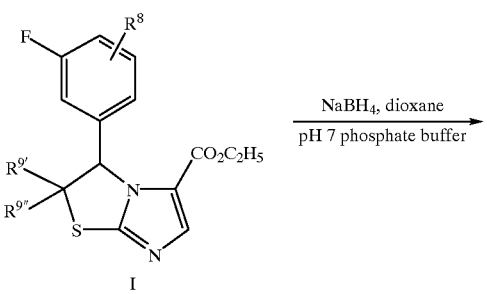
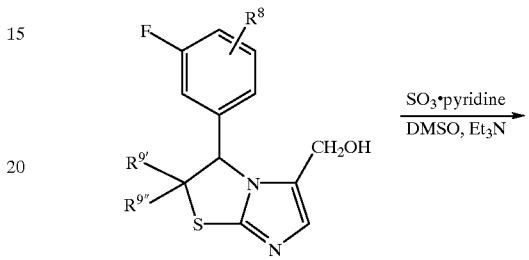
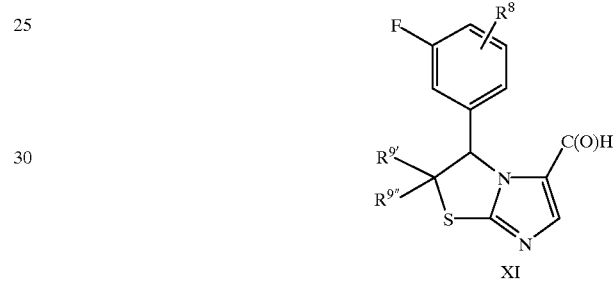
SCHEME 2
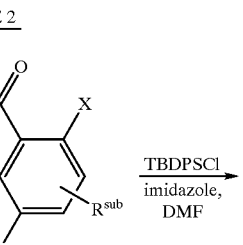
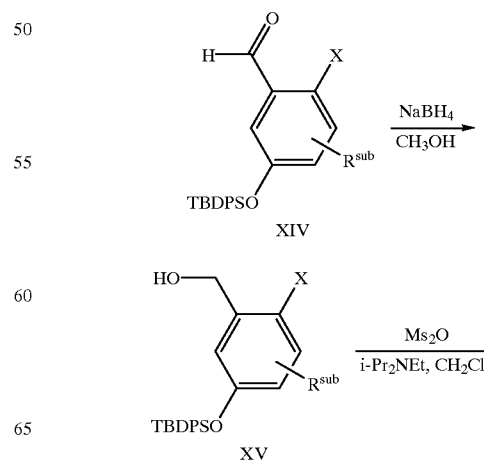

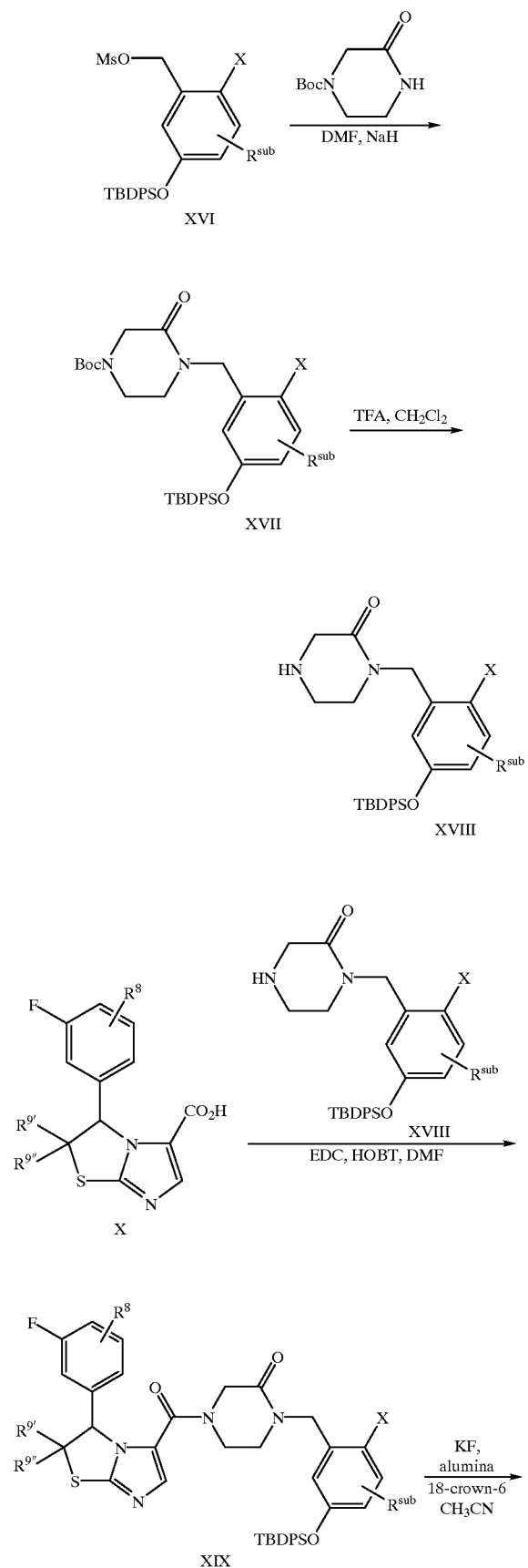
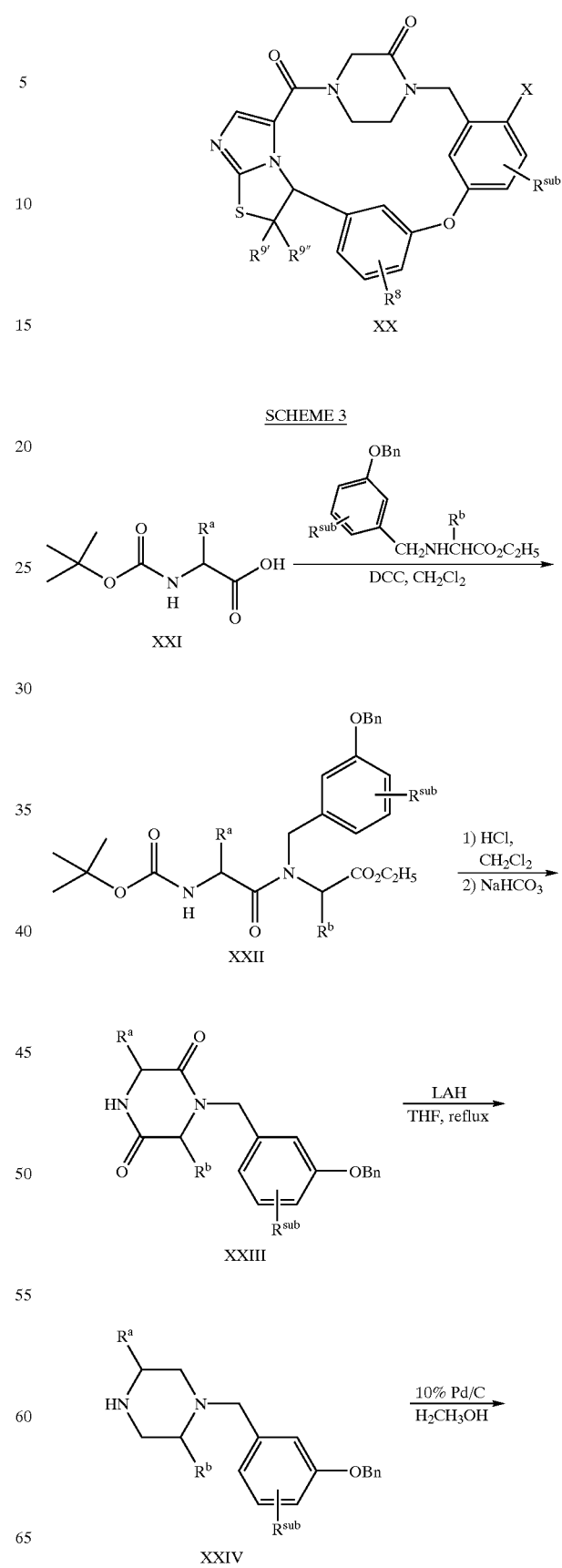
SCHEME 3

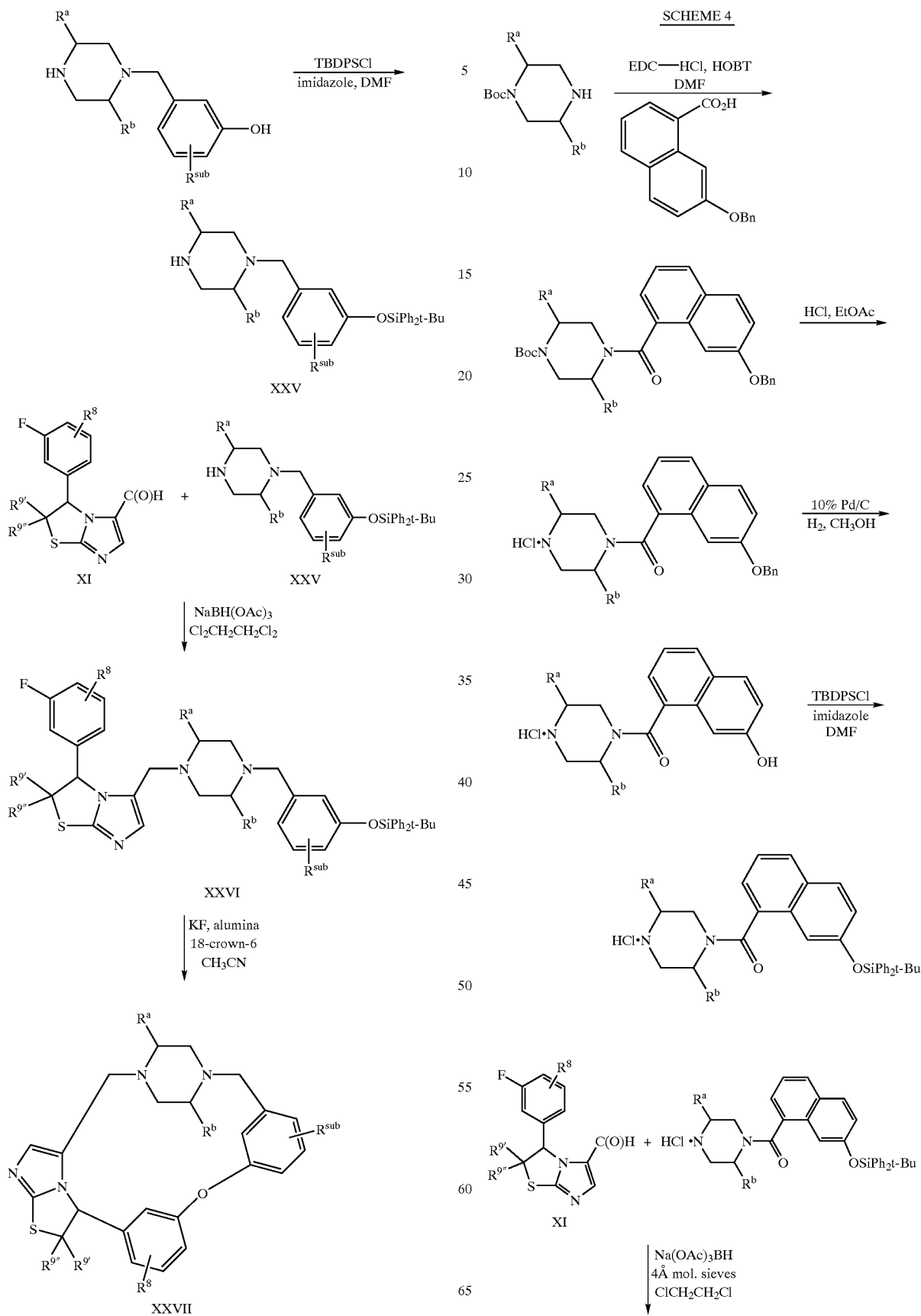

31
-continued
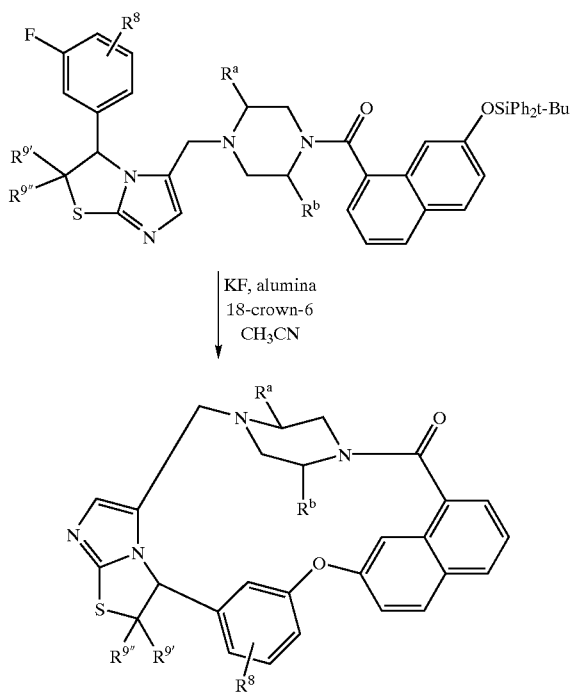
32
-continued
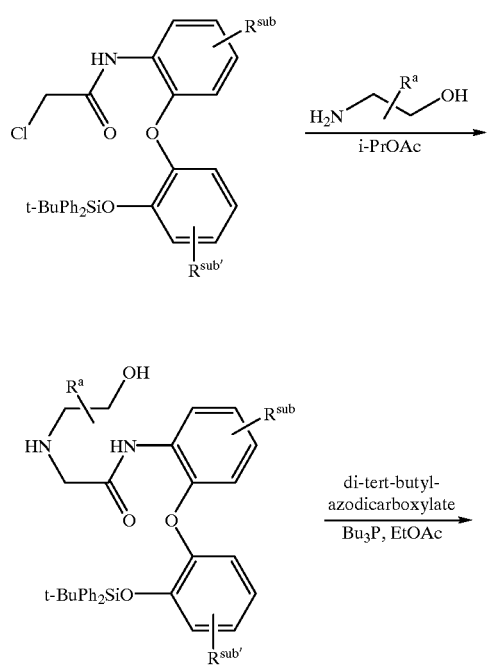
SCHEME 5
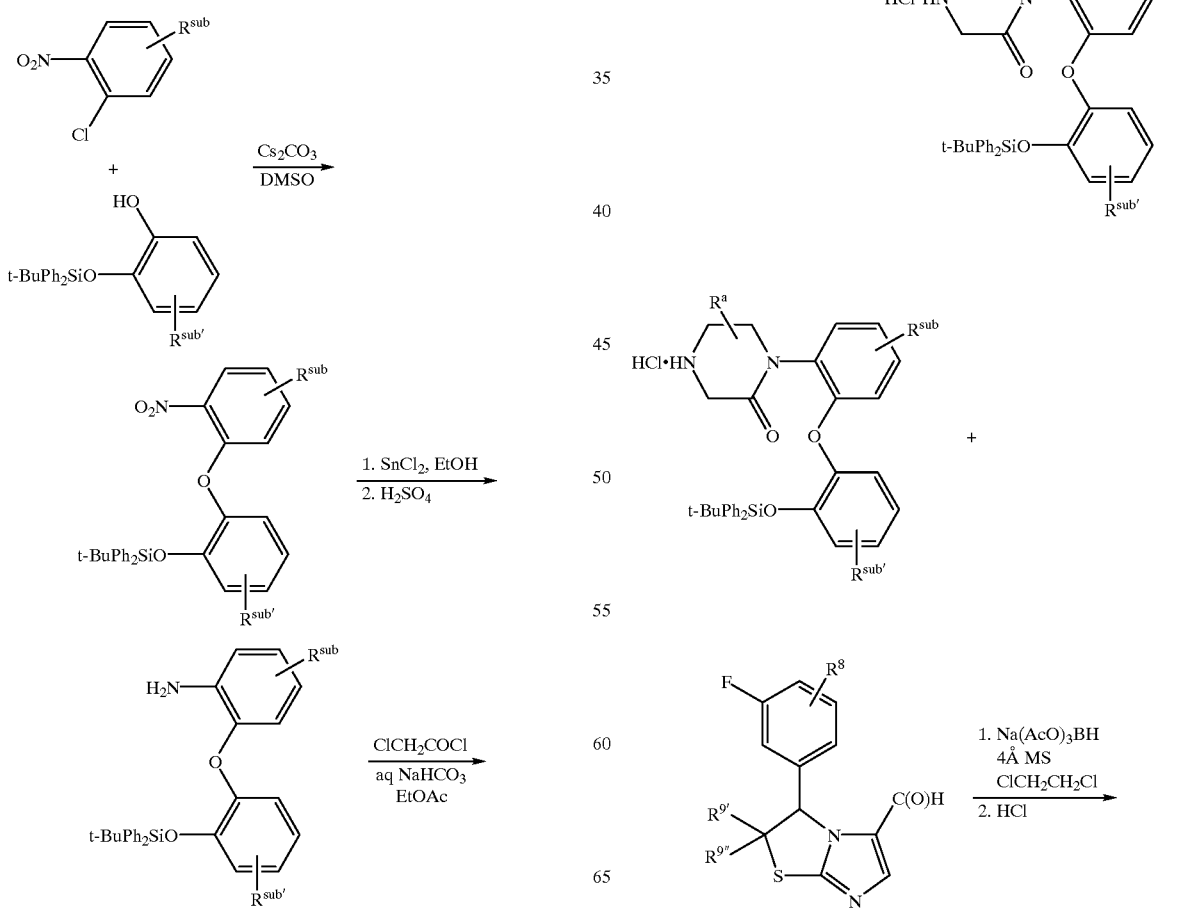

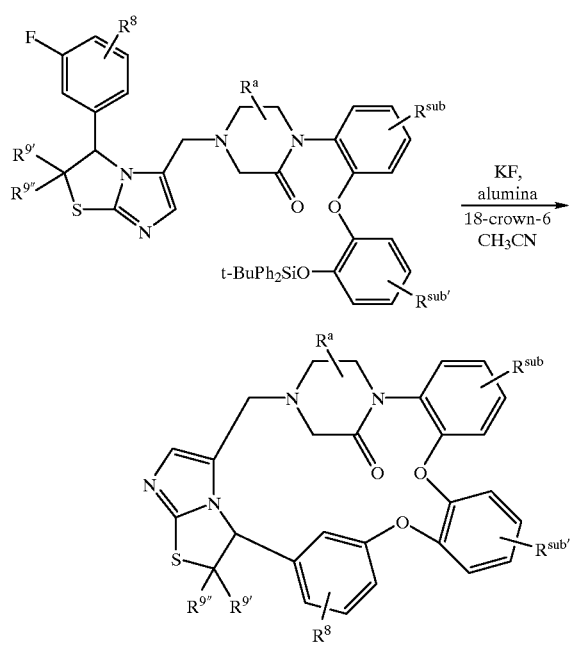
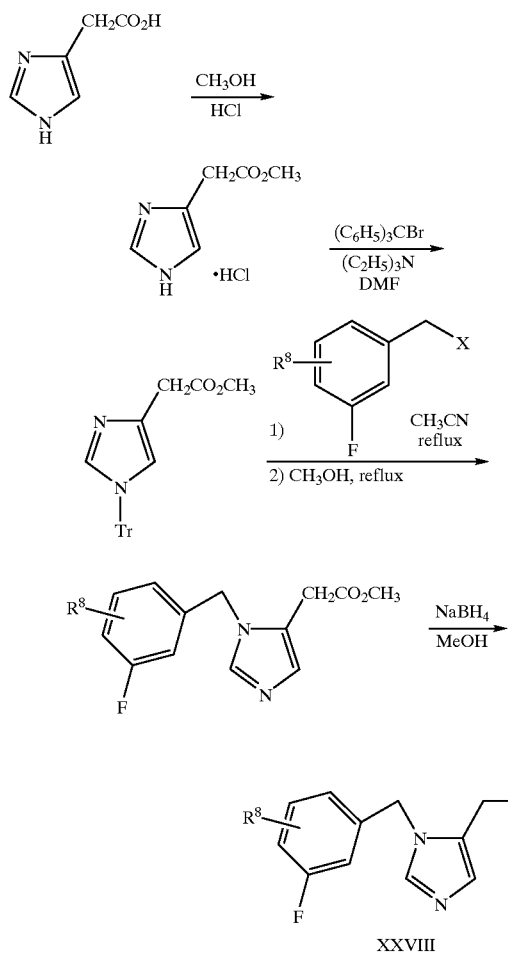
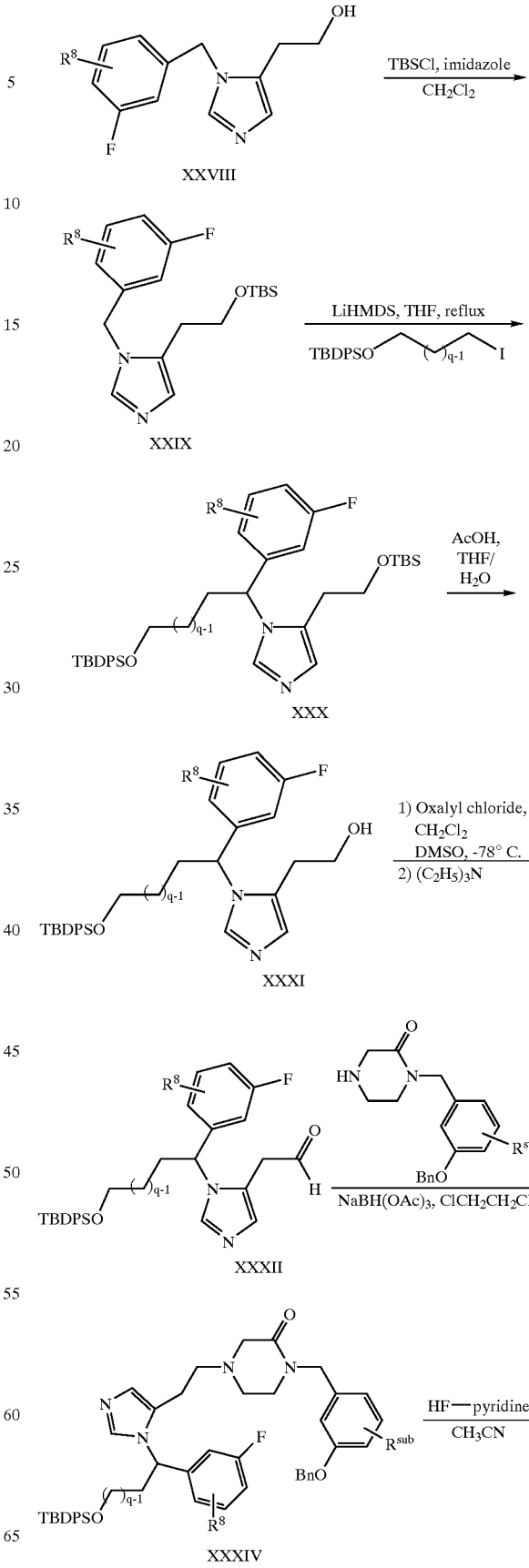
SCHEME 6

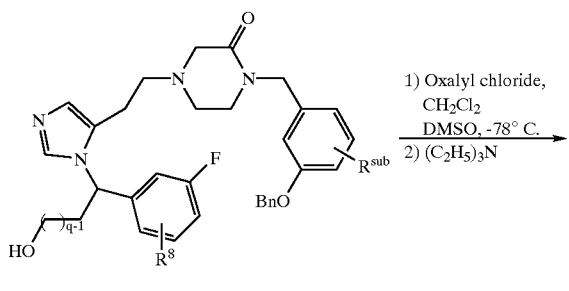
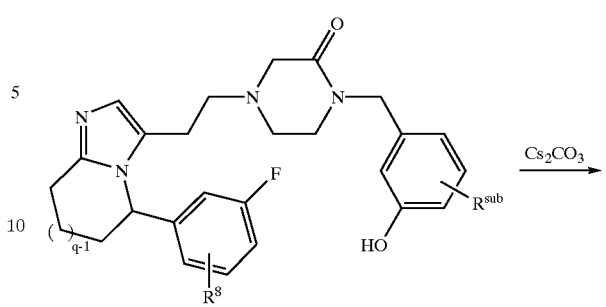
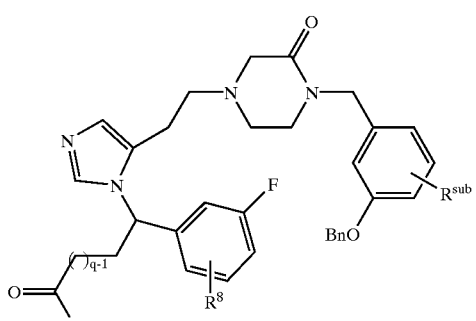
XXXV
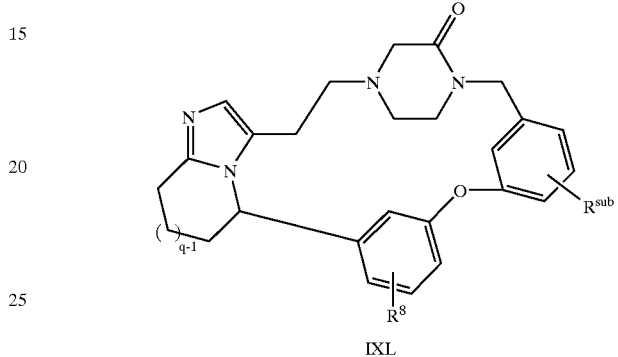
IXL
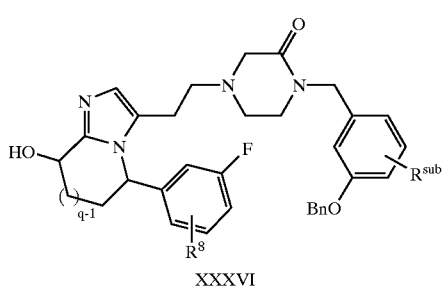
XXXVI
SCHEME 7
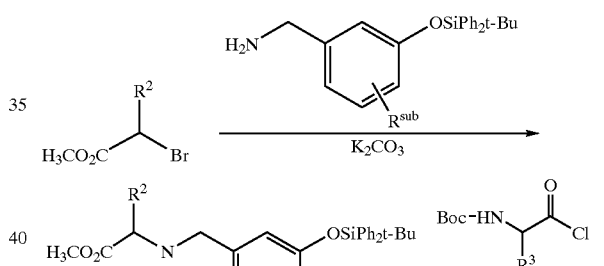
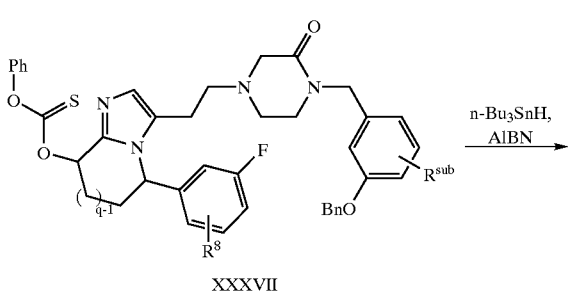
XXXVII
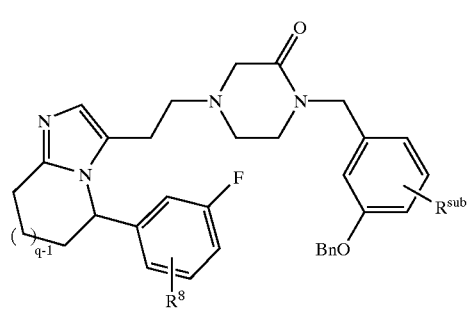
XXXVIII
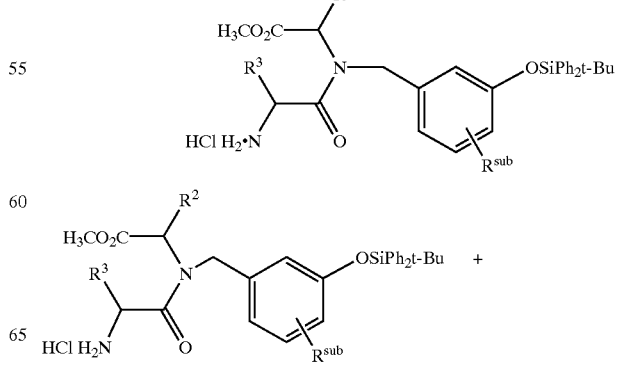

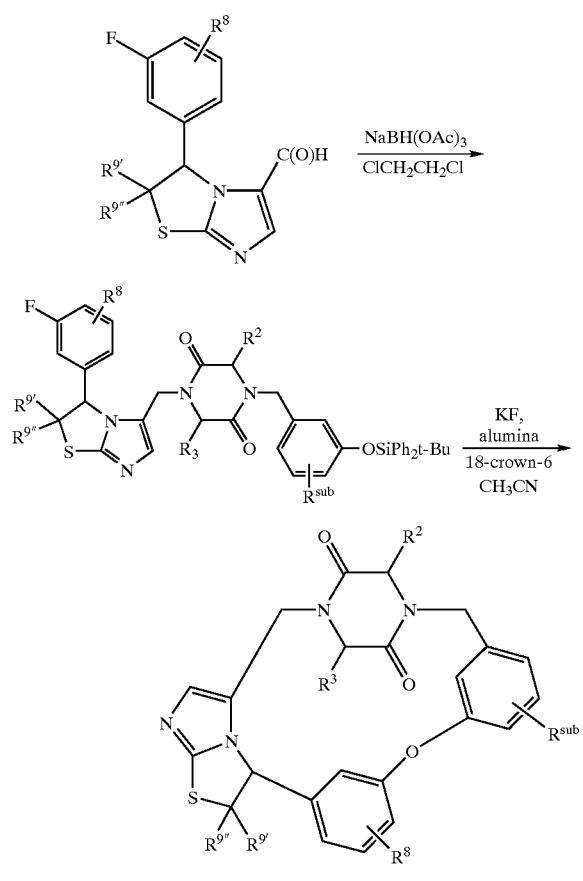
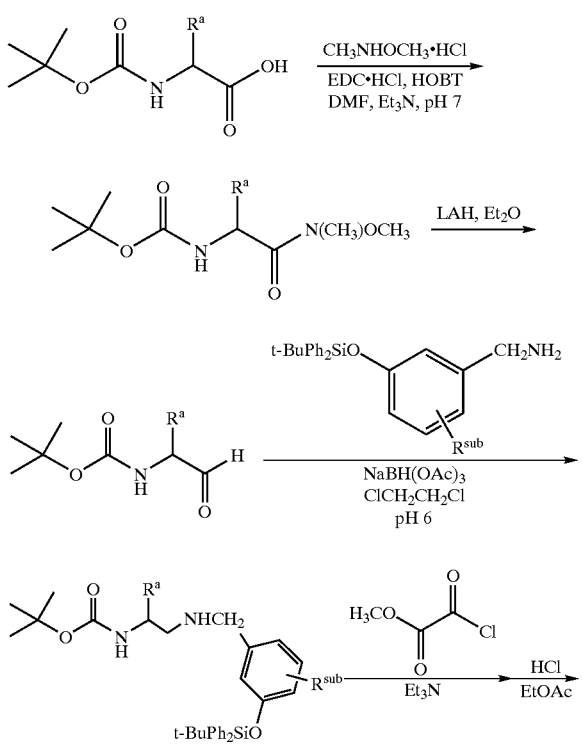
SCHEME 8
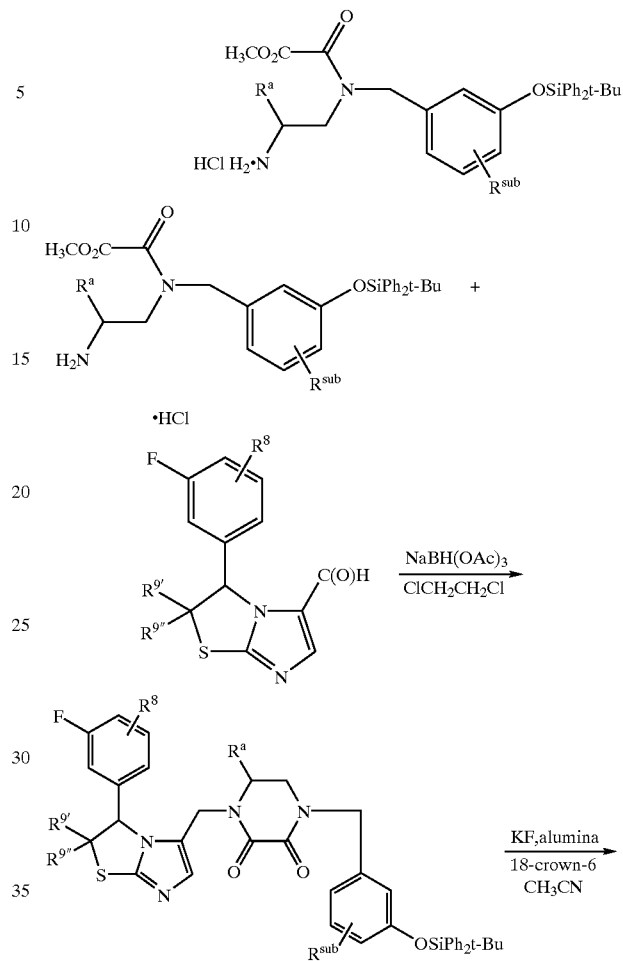
SCHEME 9

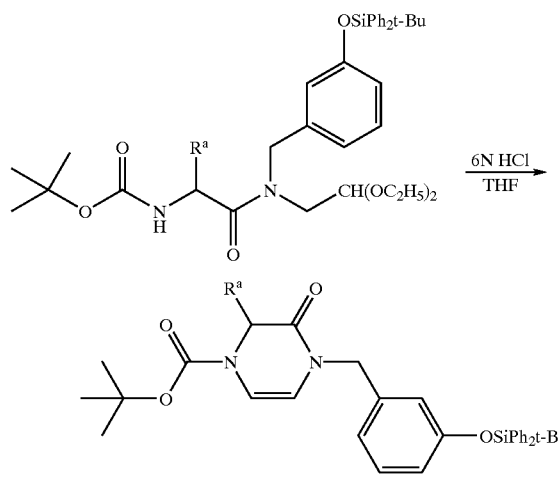
SCHEME 10
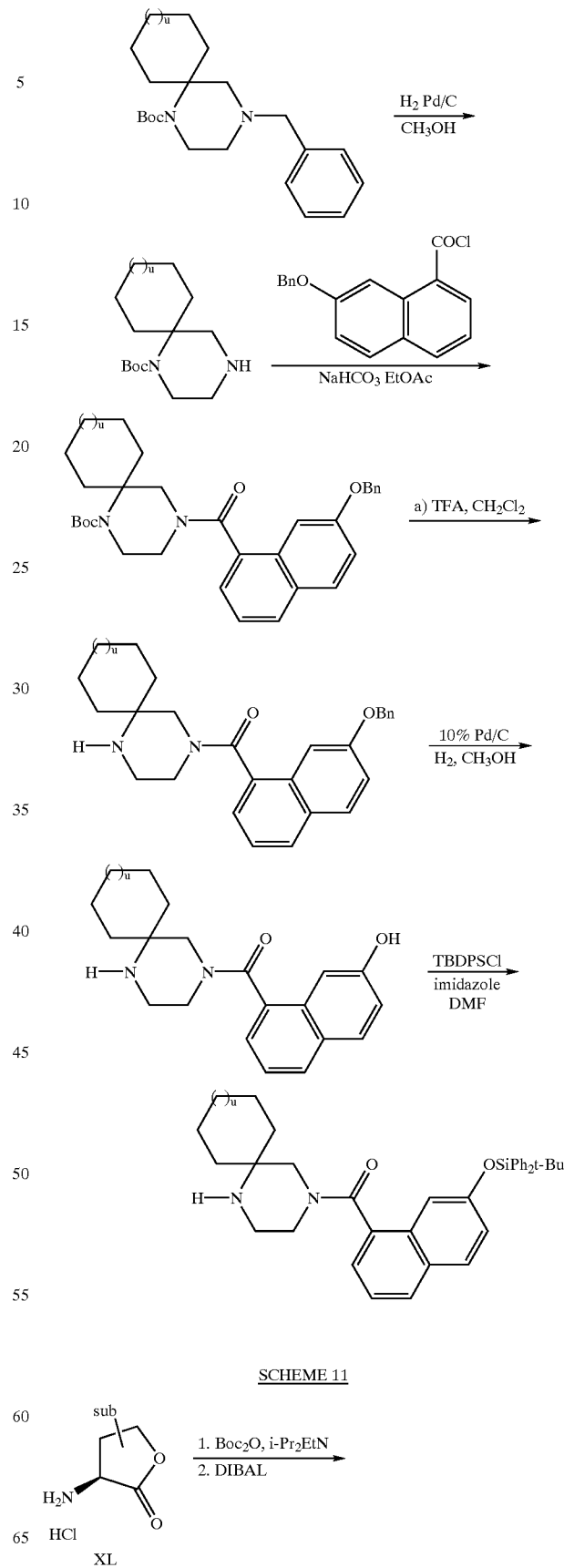
SCHEME 11

-continued
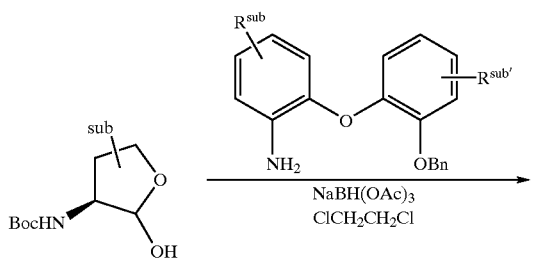
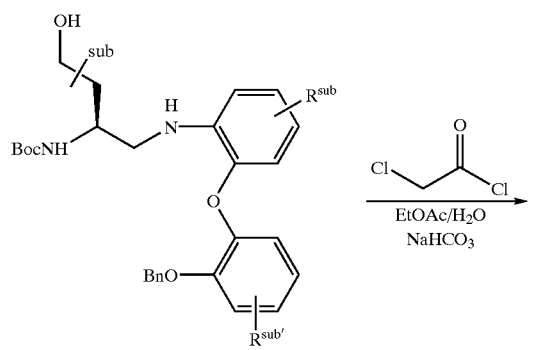
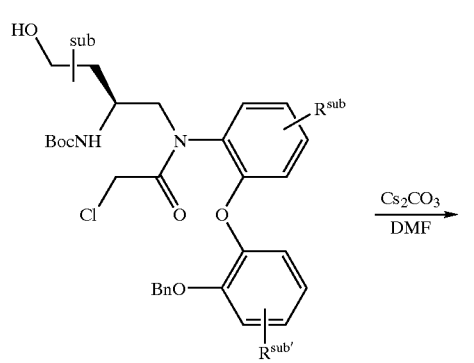
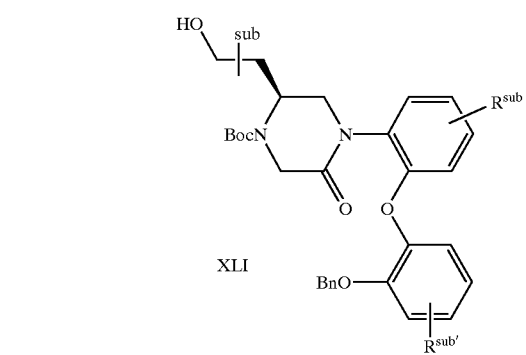
-continued
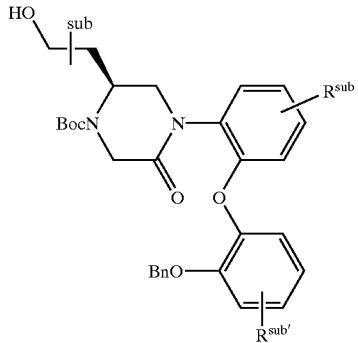
XLI
1. MsCl, iPr$_2$NEt
2. NaSEt, DMF
1. (COCl)$_2$, Et$_3$N
   DMSO
2. NaClO$_2$, t-BuOH
   2-Me-2-butene
   NaH$_2$PO$_4$
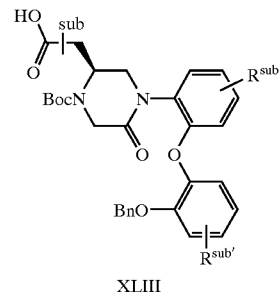
XLII        XLIII
SCHEME 12
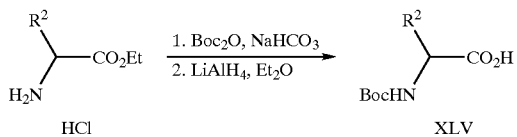
SCHEME 13
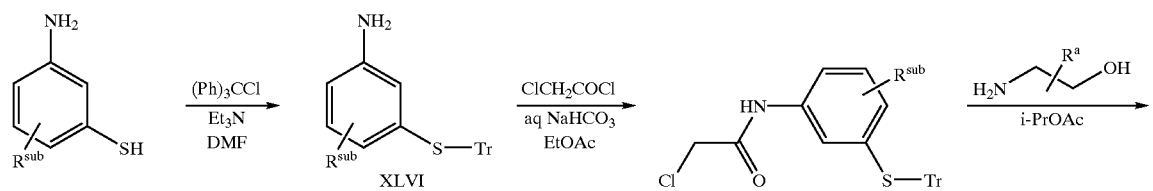

-continued
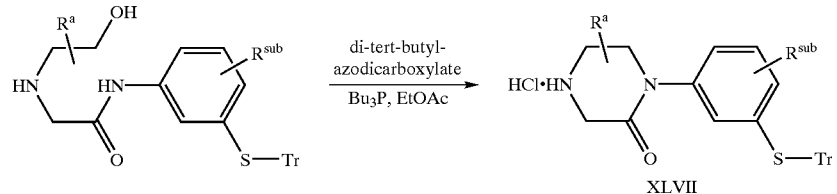
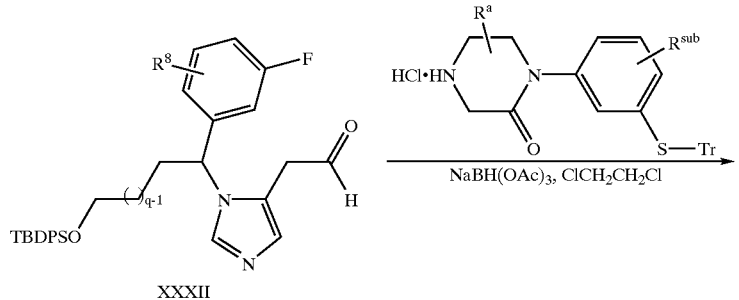
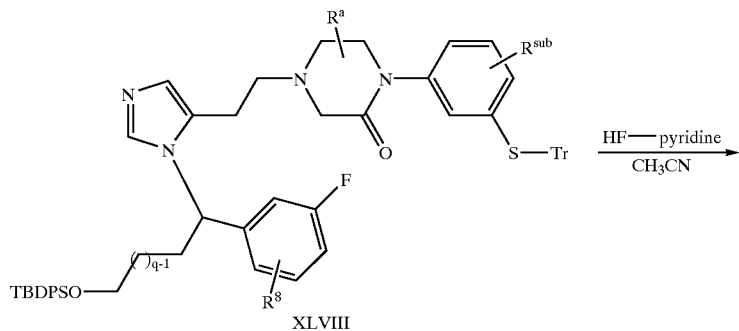
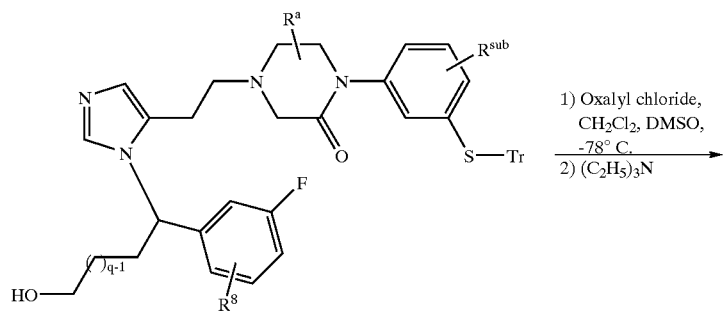
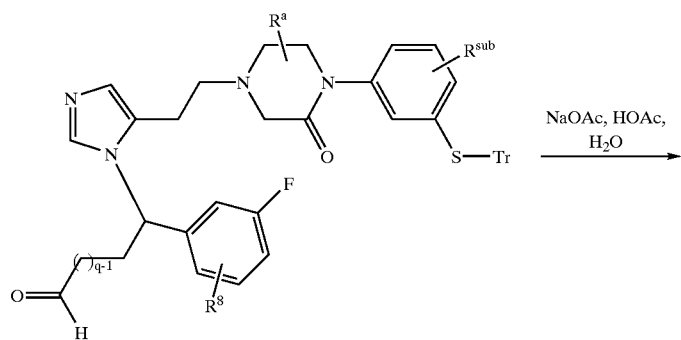

-continued
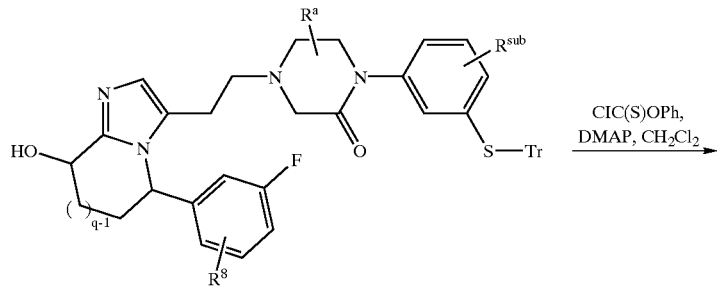
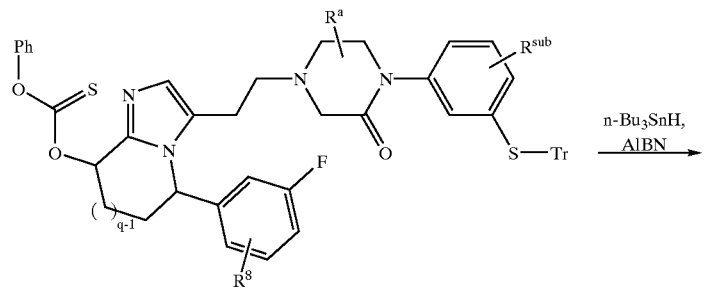
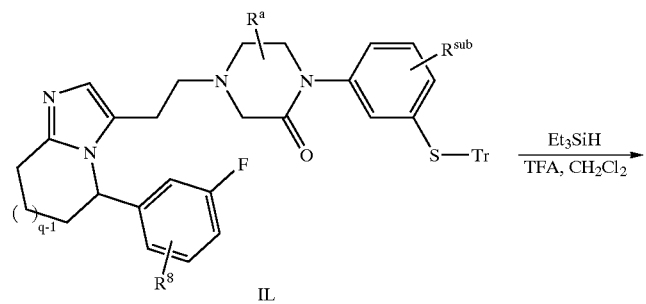
IL
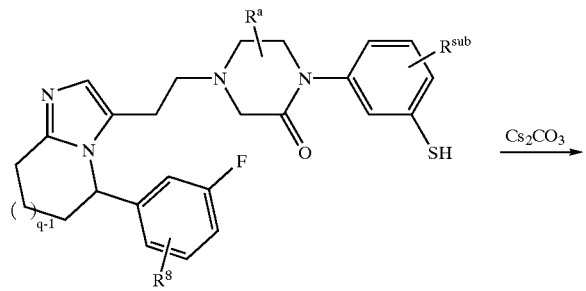
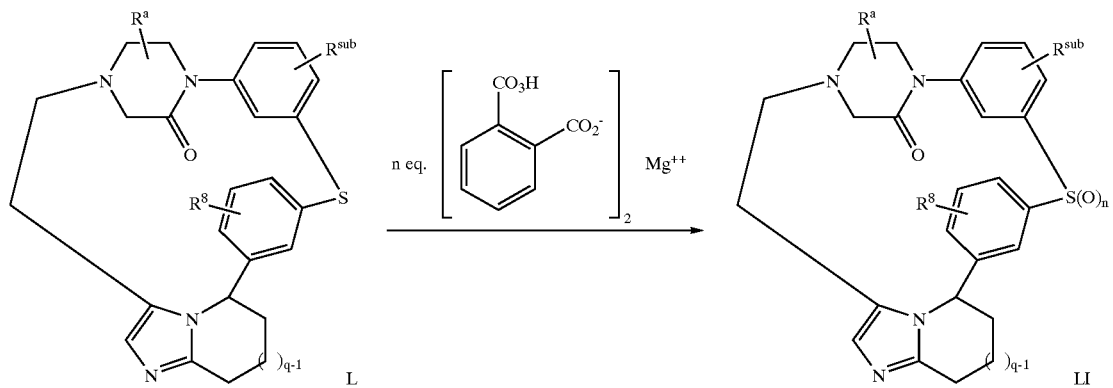
L
LI

SCHEME 14
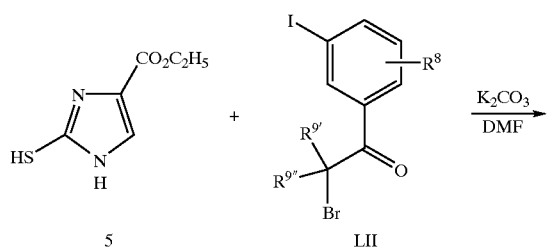
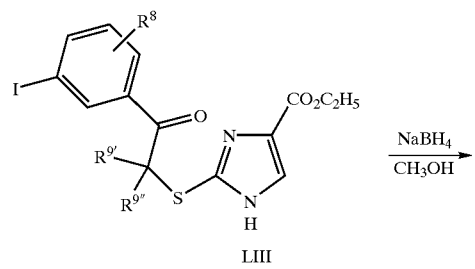
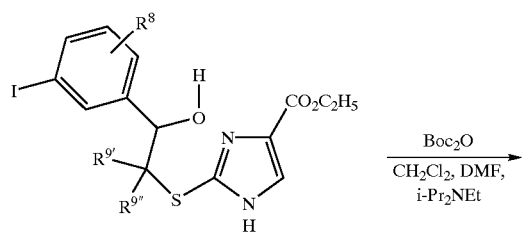
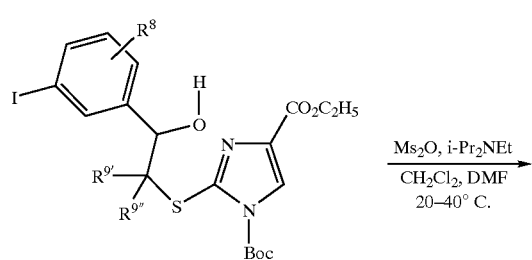
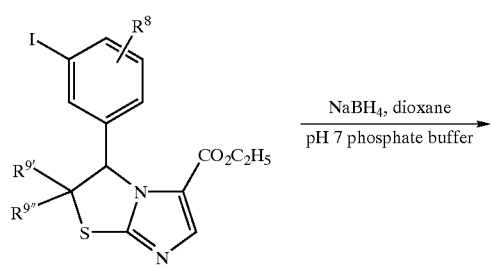
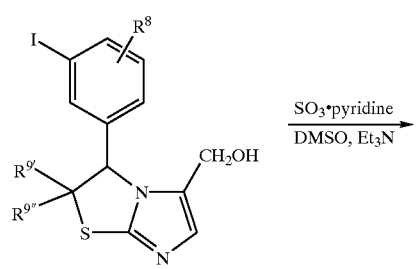
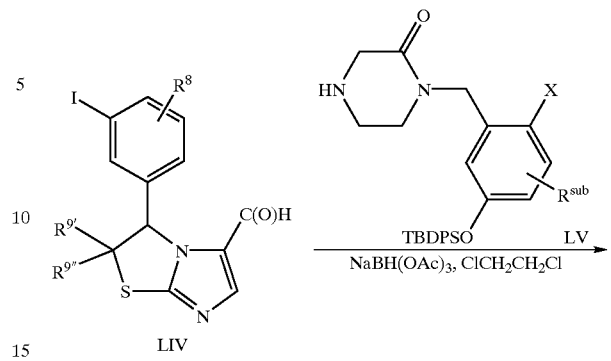
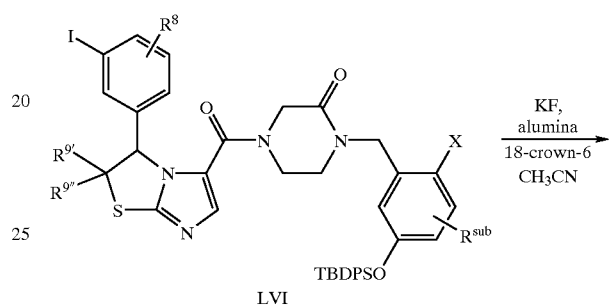
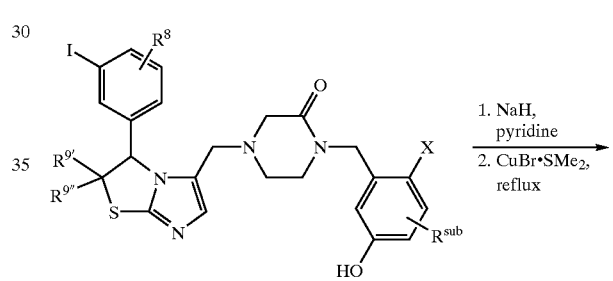
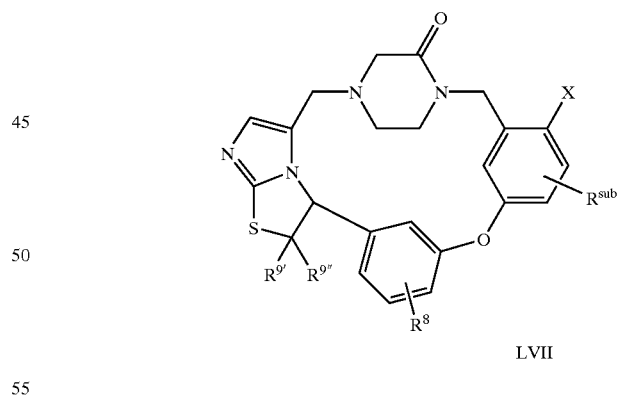
SCHEME 15
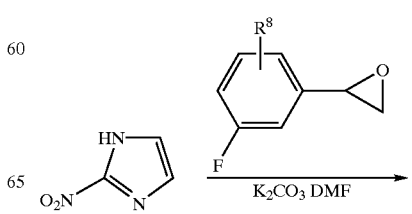

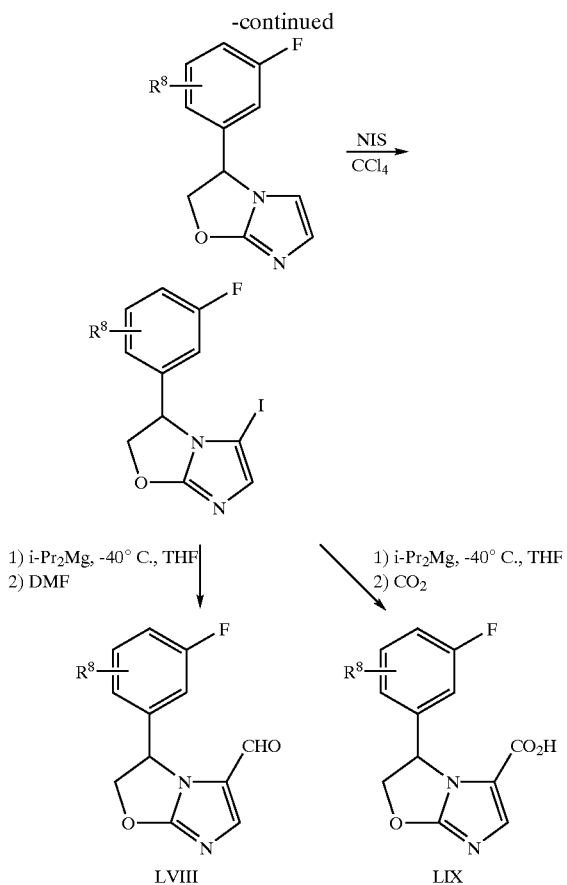

LVIII  LIX

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 9, is at least 100 times greater than the in vitro activity of the same compound against geranylgeranyl-protein transferase-type I in the assay described in Example 10. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:

a) an $IC_{50}$ (a measure of in vitro inhibitory activity) for inhibition of the prenylation of newly synthesized K-Ras protein more than about 100-fold higher than the $EC_{50}$ for the inhibition of the farnesylation of hDJ protein.

When measuring such $IC_{50}$s and $EC_{50}$s the assays described in Example 14 may be utilized.

It is also preferred that the selective inhibitor of farnesyl-protein transferase is further characterized by:

b) an $IC_{50}$ (a measurement of in vitro inhibitory activity) for inhibition of K4B-Ras dependent activation of MAP kinases in cells at least 100-fold greater than the $EC_{50}$ for inhibition of the farnesylation of the protein hDJ in cells.

It is also preferred that the selective inhibitor of farnesyl-protein transferase is further characterized by:

c) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 13 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Examples 13, it is preferred that the dual inhibitor compound has an in vitro inhibitory activity ($IC_{50}$) that is less than about 12 μM against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 13.

In yet another embodiment, a compound of the instant invention may be a more potent inhibitor of geranylgeranyl-protein transferase-type I than it is an inhibitor of farnesyl-protein transferase.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research,* 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the composition is useful in the treatment of neurofibromatosis, which is a benign proliferative disorder.

The instant compounds may also be useful in the treatment of certain viral infections, in particular in the treatment of hepatitis delta and related viruses (J. S. Glenn et al. *Science,* 256:1331–1333 (1992).

The compounds of the instant invention are also useful in the prevention of restenosis after percutaneous transluminal coronary angioplasty by inhibiting neointimal formation (C. Indolfi et al. *Nature medicine,* 1:541–545(1995).

The instant compounds may also be useful in the treatment and prevention of polycystic kidney disease (D. L. Schaffner et al. *American Journal of Pathology,* 142:1051–1060 (1993) and B. Cowley, Jr. et al. *FASEB Journal,* 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of the instant invention may also be useful in the prevention and treatment of endometriosis, uterine fibroids, dysfunctional uterine bleeding and endometrial hyperplasia.

In such methods of prevention and treatment as described herein, the prenyl-protein transferase inhibitors of the instant invention may also be co-administered with other well known therapeutic agents that are selected for their particular usefulness against the condition that is being treated. For example, the prenyl-protein transferase inhibitor may be useful in further combination with drugs known to supress the activity of the ovaries and slow the growth of the endometrial tissue. Such drugs include but are not limited to oral contraceptives, progestins, danazol and GnRH (gonadotropin-releasing hormone) agonists.

Administration of the prenyl-protein transferase inhibitor may also be combined with surgical treatment of endometriosis (such as surgical removal of misplaced endometrial tissue) where appropriate.

The instant compounds may also be useful as inhibitors of corneal inflammation. These compounds may improve the treatment of corneal opacity which results from cauterization-induced corneal inflammation. The instant compounds may also be useful in reducing corneal edema and neovascularization. (K. Sonoda et al., *Invest. Ophthalmol. Vis. Sci.,* 1998, vol. 39, p 2245–2251).

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

Additionally, the compounds of the instant invention may be administered to a mammal in need thereof using a gel extrusion mechanism (GEM) device, such as that described in U.S. Ser. No. 60/144,643, filed on Jul. 20, 1999, which is hereby incorporated by reference.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intra-nasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds f the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that such a combination of antineoplastic agent and inhibitor of prenyl-protein transferase may be used in conjunction with other methods of treating cancer and/or tumors, including radiation therapy and surgery. It is further understood that any of the therapeutic agents described herein may also be used in combination with a compound of the instant invention and an antineoplastic agent.

Examples of an antineoplastic agent include, in general, microtubule-stabilizing agents such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, for example, nitrogen mustards, ethyleneimine compounds, alkyl sulfonates and other compounds with an alkylating action such as nitrosoureas, cisplatin, and dacarbazine; anti-metabolites, for example, folic acid, purine or pyrimidine antagonists; epidophyllotoxin; an antineoplastic enzyme; a topoisomerase inhibitor; procarbazine; mitoxantrone; platinum coordination complexes; biological response modifiers and growth inhibitors; mitotic inhibitors, for example, vinca alkaloids and derivatives of podophyllotoxin; cytotoxic antibiotics; hormonal/anti-hormonal therapeutic agents, haematopoietic growth factors and antibodies (such as trastuzumab, also known as Herceptin™).

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, dactinomycin, mechlorethamine (nitrogen mustard), streptozocin, cyclophosphamide, carmustine (BCNU), lomustine (CCNU), procarbazine, mitomycin, cytarabine, etoposide, methotrexate, bleomycin, chlorambucil, camptothecin, CPT-11, topotecan, ara-C, bicalutamide, flutamide, leuprolide, pyridobenzoindole derivatives, interferons and interleukins. Particular examples of antineoplastic, or chemotherapeutic, agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. See also, R. J. Gralla, et al., Cancer Treatment Reports, 68(1), 163–172 (1984).

The preferred class of antineoplastic agents is the taxanes and the preferred antineoplastic agent is paclitaxel.

The compounds of the instant invention may also be co-administered with antisense oligonucleotides which are specifically hybridizable with RNA or DNA deriving from human ras gene. Such antisense oligonucleotides are described in U.S. Pat. No. 5,576,208 and PCT Publ. No. WO 99/22772. The instant compounds are particularly useful when co-administered with the antisense oligonucleotide comprising the amino acid sequence of SEQ.ID.NO: 2 of U.S. Pat. No. 5,576,208.

Certain compounds of the instant invention may exhibit very low plasma concentrations and significant inter-individual variation in the plasma levels of the compound. It is believed that very low plasma concentrations and high intersubject variability achieved following administration of certain prenyl-protein transferase inhibitors to mammals may be due to extensive metabolism by cytochrome P450 enzymes prior to entry of drug into the systemic circulation. Prenyl-protein transferase inhibitors may be metabolized by cytochrome P450 enzyme systems, such as CYP3A4, CYP2D6, CYP2C9, CYP2C19 or other cytochrome P450 isoform. If a compound of the instant invention demonstrates an affinity for one or more of the cytochrome P450 enzyme systems, another compound with a higher affinity for the P450 enzyme(s) involved in metabolism should be administered concomitantly. Examples of compounds that have a comparatively very high affinity for CYP3A4, CYP2D6, CYP2C9, CYP2C19 or other P450 isoform include, but are not limited to, piperonyl butoxide, troleandomycin, erythromycin, proadifen, isoniazid, allylisopropylacetamide, ethinylestradiol, chloramphenicol, 2-ethynylnaphthalene and the like. Such a high affinity compound, when employed in combination with a compound of formula A, may reduce the inter-individual variation and increase the plasma concentration of a compound of formula A to a level having substantial therapeutic activity by inhibiting the metabolism of the compound of formula A. Additionally, inhibiting the metabolism of a compound of the instant invention prolongs the pharmacokinetic half-life, and thus the pharmacodynamic effect, of the compound.

A compound of the present invention may be employed in conjunction with antiemetic agents to treat nausea or emesis, including acute, delayed, late-phase, and anticipatory emesis, which may result from the use of a compound of the present invention, alone or with radiation therapy. For the prevention or treatment of emesis a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, or a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712. For the treatment or prevention of emesis, conjunctive therapy with a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0

714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

A particularly preferred neurokinin-1 receptor antagonist for use in conjunction with the compounds of the present invention is 2-(R)-(1-(R)-(3,5-bis(trifluoromethyl)phenyl) ethoxy)-3-(S)-(4-fluorophenyl)-4-(3-(5-oxo-1 H,4H-1,2,4-triazolo)methyl)morpholine, or a pharmaceutically acceptable salt thereof, which is described in U.S. Pat. No. 5,719,147.

For the treatment of cancer, it may be desirable to employ a compound of the present invention in conjunction with another pharmacologically active agent(s). A compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). In general, the currently available dosage forms of the known therapeutic agents for use in such combinations will be suitable.

For example, a compound of the present invention may be presented together with another therapeutic agent in a combined preparation, such as with an antiemetic agent for simultaneous, separate, or sequential use in the relief of emesis associated with employing a compound of the present invention and radiation therapy. Such combined preparations may be, for example, in the form of a twin pack. A preferred combination comprises a compound of the present invention with antiemetic agents, as described above.

Radiation therapy, including x-rays or gamma rays which are delivered from either an externally applied beam or by implantation of tiny radioactive sources, may also be used in combination with the instant inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase.

In particular, if the compound of the instant invention is a selective inhibitor of farnesyl-protein transferase, co-administration with a compound(s) that is a selective inhibitor of geranylgeranyl protein transferase may provide an improved therapeutic effect.

In particular, the compounds disclosed in the following patents and publications may be useful as farnesyl pyrophosphate-competitive inhibitor component of the instant composition: U.S. Ser. Nos. 08/254,228 and 08/435, 047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, and WO 98/44797, published on Oct. 15, 1998, which are incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the $\alpha v\beta 3$ integrin, which selectively antagonize, inhibit or counteract binding of a physiological ligand to the $\alpha v\beta 5$ integrin, which antagonize, inhibit or counteract binding of a physiological ligand to both the $\alpha v\beta 3$ integrin and the $\alpha v\beta 5$ integrin, or which antagonize, inhibit or counteract the activity of the particular integrin(s) expressed on capillary endothelial cells. The term also refers to antagonists of the $\alpha 1\beta 1$, $\alpha 2\beta 1$, $\alpha 5\beta 1$, $\alpha 6\beta 1$ and $\alpha 6\beta 4$ integrins. The term also refers to antagonists of any combination of $\alpha v\beta 3$ integrin, $\alpha v\beta 5$ integrin, $\alpha 1\beta 1$, $\alpha 2\beta 1$, $\alpha 5\beta 1$, $\alpha 6\beta 1$ and $\alpha 6\beta 4$ integrins. The instant compounds may also be useful with other agents that inhibit angiogenisis and thereby inhibit the growth and invasiveness of tumor cells, including, but not limited to angiostatin and endostatin.

The instant compounds may also be useful in combination with an inhibitor of 3-hydroxy-3-methylglutaryl-CoA reductase (HMG-CoA reductase) for the treatment of cancer. Compounds which have inhibitory activity for HMG-CoA reductase can be readily identified by using assays well-known in the art. For example, see the assays described or cited in U.S. Pat. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85–89 (Feb. 5, 1996) and U.S Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

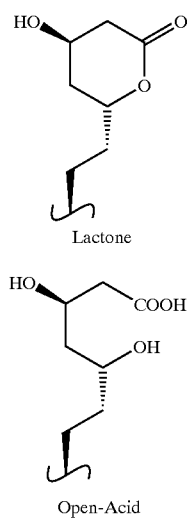

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described above and the other pharmaceutically active agent(s) within its approved dosage range. Combinations of the instant invention may alternatively be used sequentially with known pharmaceutically acceptable agent(s) when a multiple combination formulation is inappropriate.

The instant compounds may also be useful in combination with prodrugs of antineoplastic agents. In particular, the instant compounds may be co-administered either concurrently or sequentially with a conjugate (termed a "PSA conjugate") which comprises an oligopeptide, that is selectively cleaved by enzymatically active prostate specific antigen (PSA), and an antineoplastic agent. Such co-administration will be particularly useful in the treatment of prostate cancer or other cancers which are characterized by the presence of enzymatically active PSA in the immediate surrounding cancer cells, which is secreted by the cancer cells.

Compounds which are PSA conjugates and are therefore useful in such a co-administration, and methods of synthesis thereof, can be found in the following patents, pending patent applications and publications which are herein incorporated by reference:

U.S. Pat. No. 5,599,686, granted on Feb. 4, 1997;
WO 96/00503 (Jan. 11, 1996); U.S. Ser. No. 08/404,833, filed on Mar. 15, 1995; U.S. Ser. No. 08/468,161, filed on Jun. 6, 1995;
U.S. Pat. No. 5,866,679, granted on Feb. 2, 1999;
WO 98/10651 (Mar. 19, 1998); U.S. Ser. No. 08/926,412, filed on Sep. 9, 1997;
WO 98/18493 (May 7, 1998); U.S. Ser. No. 08/950,805, filed on Oct. 14, 1997;
WO 99/02175 (Jan. 21, 1999); U.S. Ser. No. 09/112,656, filed on Jul. 9, 1998; and
WO 99/28345 (Jun. 10, 1999); U.S. Ser. No. 09/193,365, filed on Nov. 17, 1998.

Compounds which are described as prodrugs wherein the active therapeutic agent is released by the action of enzymatically active PSA and therefore may be useful in such a co-administration, and methods of synthesis thereof, can be found in the following patents, pending patent applications and publications, which are herein incorporated by reference: WO 98/52966 (Nov. 26, 1998).

All patents, publications and pending patent applications identified are herein incorporated by reference.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immuno-logical, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof. Hydrocloride and bishydrochloride salts of the compounds described were generally prepared by the following method: The purified free base was dissolved in methanol, $CH_2Cl_2$ or a combination of the solvents. A molar excess of a solution of hydrochloric acid in ether (Aldrich) was added and the solvent then removed under vacuum to provide the acid salt.

Example 1

(R)-15-Bromo-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile hydrochloride and (S)-15-Bromo-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile hydrochloride

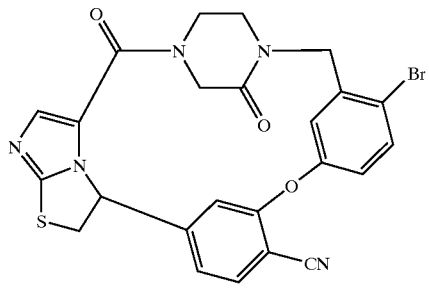

Step A: Preparation of 2-bromo-5-(tert-butyldiphenylsilyloxy)-benzaldehyde

A solution of 2-bromo-5-hydroxybenzaldehyde (4.66 g, 23.2 mmol), tert-butyldiphenylchlorosilane (7.73 mL, 30.6 mmol), and imidazole (2.37 g, 34.8 mmol) in DMF (50 mL) was stirred at 25° C. for 12 hours and 60° C. for 12 hours. The solvent was removed in vacuo and the residue partitioned between methylene chloride (100 mL) and saturated aqueous sodium bicarbonate (100 mL). The layers were separated and the aqueous layer was extracted with methylene chloride (3×100 mL). The combined organic layers were dried over sodium sulfate, filtered, and concentrated in vacuo. The crude product was purified by column chromatography (10% ethyl acetate/hexane) to provide the title compound as a yellow oil.

Step B: Preparation of [2-bromo-5-(tert-butyldiphenylsilyloxy)-phenyl]-methanol

The product from Step A (8.87 g, 20.2 mmol) was dissolved in methanol (50 mL) and methylene chloride (20 mL). Sodium borohydride (764 mg, 20.2 mmol) was added in portions at 0° C., and the solution was stirred for 2 hours. The reaction was quenched by the addition of saturated aqueous ammonium chloride until hydrogen evolution ceased. The resulting suspension was concentrated in vacuo and then partitioned between methylene chloride (50 mL) and saturated aqueous sodium bicarbonate (50 mL). The layers were separated and the aqueous layer was extracted with methylene chloride (3×100 mL). The combined organic layers were dried over sodium sulfate, filtered, and concentrated in vacuo to provide the title product as a yellow oil which was sufficiently pure for use in the next step.

Step C: Preparation of 4-bromo-1-(tert-butyldiphenylsilyloxy)-3-(methanesulfonyloxymethyl)benzene To a solution of alcohol from Step B (8.91 g, 20.2 mmol) and N,N-diisopropylethylamine (5.27 mL, 30.3 mmol) in methylene chloride (50 mL) was added methanesulfonic anhydride (4.22 g, 24.2 mmol) in one portion. The reaction was stirred for 16 hours at 25° C. The reaction was poured onto saturated aqueous sodium bicarbonate and extracted with methylene chloride (3×100 mL). The combined organic layers were dried over sodium sulfate, filtered, and concentrated in vacuo to provide the title product as a dark yellow oil which was sufficiently pure for use in the next step.

Step D: Preparation of 4-[2-bromo-5-(tert-butyldiphenylsilyloxy)-benzyl]-3-oxo-piperazine-1-carboxylic acid tert-butyl ester To a solution piperazin-3-one-1-carboxylic acid tert-butyl ester (2.11 g, 10.5 mmol) in dry DMEF (20 mL) at 0° C. was added sodium hydride (60% dispersion in mineral oil, 632 mg, 15.8 mmol). The reaction mixture was stirred for 1 hour, and then a solution of the mesylate from Step C (5.47 g, 10.5 mmol) in DMF (10 mL) was added. The reaction mixture was stirred for 16 hours. The solvent was removed in vacuo and the residue partitioned between methylene chloride (100 mL) and saturated aqueous sodium bicarbonate (100 mL). The layers were separated and the aqueous layer was extracted with methylene chloride (3×100 mL). The combined organic layers were dried over sodium sulfate, filtered, and concentrated in vacuo. The crude product was purified by column chromatography (20→50% ethyl acetate/hexane) to provide the title compound as a yellow oil.

Step E: Preparation of 1-[2-bromo-5-(tert-butyldiphenylsilyloxy)-benzyl]-piperazin-2-one To a solution of product from Step D (2.30 g, 3.69 mmol) in methylene chloride (16 mL) was added trifluoroacetic acid (4 mL). The resulting solution was stirred for 3 hours, then poured onto saturated aqueous sodium bicarbonate, and extracted with methylene chloride (3×50 mL). The combined organic layers were dried over sodium sulfate, filtered, and concentrated in vacuo to provide the title product as a yellow oil which was sufficiently pure for use in the next step.

Step F: Preparation of 4-cyano-3-fluoroacetophenone

A solution of 4-bromo-3-fluorobenzonitrile (10.1 g, 50.4 mmol), tributyl(1-ethoxyvinyl)tin (20.0 g, 54.4 mmol), and dichloro-bis(triphenylphosphine)palladium (II) (353 mg, 0.504 mmol) in toluene (200 mL) was heated at reflux for 12 hours. The reaction mixture was cooled to room temperature and treated with 5% HCl (50 mL) for 24 hours. The reaction was poured onto water and extracted with ethyl acetate (3×100 mL). The combined organic layers were dried over sodium sulfate, filtered, and concentrated in vacuo to provide a yellow oil. The crude product was purified by column chromatography (20→35% ethyl acetate/hexane) to provide the title compound as a white solid which was sufficiently pure for use in the next step.

Step G: Preparation of 4-cyano-3-fluorophenacyl bromide

To a solution of product from Step F (7.77 g, 47.6 mmol) in dioxane (100 mL) open to the atmosphere was added bromine (2.45 mL, 47.6 mmol) dropwise. The resulting orange solution was stirred until it turned yellow (1 hour). The reaction mixture was then concentrated to provide a mixture of the title compound, (α,α-dibrominated by-product, and starting material in a 82:13:05 ratio. This mixture was used in the next step without further purification.

Step H: Preparation of ethyl 2-[2-(4-cyano-3-fluorophenyl)-2-oxo-ethylthio]-3H-imidazole-4-carboxylate To a solution 4-ethoxycarbonylimidazole-2-thiol (8.47 g, 49.2 mmol) and potassium carbonate (20.4 g, 148 mmol) in dry acetonitrile (200 mL) at room temperature was added bromide from Step G (11.9 g, 49.2 mmol). The reaction mixture was stirred for 20 hours, during which time a white precipitate formed. To the solution was added 100 mL ice water. The resulting solid was filtered and washed with water (2×25 mL) to provide the title product as an off-white solid which was sufficiently pure for use in the next step.

Step I: Preparation of ethyl 2-[2-(4-cyano-3-fluorophenyl)-2-hydroxy-1-ethylthio]-3H-imidazole-4-carboxylate The product from Step H (3.00 g, 9.00 mmol) was suspended in methanol (20 mL). Sodium borohydride (340 mg, 9.00 mmol) was added in portions at 0° C., and the suspension was stirred until it became homogeneous (1 hour). The reaction was quenched by the addition of saturated aqueous ammonium chloride until hydrogen evolution ceased. The resulting suspension was concentrated in vacuo and then partitioned between ethyl acetate (50 mL) and saturated aqueous sodium bicarbonate (50 mL). The layers were separated and the aqueous layer was extracted with ethyl acetate (3×100 mL). The combined organic layers were dried over sodium sulfate, filtered, and concentrated in vacuo to provide the title product as an off-white solid which was sufficiently pure for use in the next step.

Step J: Preparation of ethyl 3-(4-cyano-3-fluorophenyl)-2,3-dihydro-imidazo[2,1-b]thiazole-5-carboxylate To a solution of alcohol from Step 1 (2.99 g, 8.92 mmol) and N,N-diisopropylethylamine (4.66 mL, 26.8 mmol) in methylene chloride (100 mL)/ DMF (10 mL) was added di-tert-butyl dicarbonate (2.34 g, 10.7 mmol) at 0° C. The reaction was stirred for 24 hours, then methanesulfonic anhydride (3.11 g, 17.8 mmol) was added in one portion. The reaction was stirred for 3 hours at 25° C. and 16 hours at reflux. The reaction was poured onto saturated aqueous sodium bicarbonate and extracted with methylene chloride (3×100 mL). The combined organic layers were dried over sodium sulfate, filtered, and concentrated in vacuo to provide a yellow oil. The crude product was purified by column chromatography (30→80% ethyl acetate/hexane) to provide the title compound as a white solid.

Step K: Preparation of 3-(4-cyano-3-fluorophenyl)-2,3-dihydro-imidazo[2,1-b]thiazole-5-carboxylic acid hydrochloride To a solution of the ester from Step J (2.33 g, 7.34 mmol) in ethanol (20 mL) at 0° C. was added sodium hydroxide (1 M in water, 7.34 mL, 7.34 mmol). After 40 hours, the ethanol was evaporated in vacuo at 25° C., and the water removed by a stream of nitrogen. The crude product was acidified by the addition of hydrogen chloride (1 M in diethylether, 40 mL) and reconcentrated to provide the crude product as a white solid. The crude product was purified by column chromatography (5% methanol/chloroform containing 1% acetic acid) to provide the title compound as a white solid.

Step L: Preparation of 5-(1-{4-[2-bromo-5-(tert-butyldiphenyl-silyloxy)-benzyl]-3-oxo-piperazin-1-yl}-methanoyl)-3-(4-cyanophenyl)-2,3-dihydro-imidazo[2,1-b]thiazole The carboxylic acid from Step K (221 mg, 0.679 mmol), the piperazinone from Step E (390 mg, 0.679 mmol), EDC hydrochloride (156 mg, 0.814 mmol), HOBT (110 mg, 0.814 mmol), and N,N-diisopropylethylamine (0.591 mL, 3.39 mmol) were stirred together in dry, degassed DMF (5 mL) at 25° C. for 16 hours. The reaction was poured onto saturated aqueous sodium bicarbonate and extracted with methylene chloride (3×25 mL). The combined organic layers were washed with brine, dried over sodium sulfate, filtered, and concentrated in vacuo to provide a yellow oil. The crude product was purified by column chromatography (3% methanol/methylene chloride) to provide the title compound as a yellow solid.

Step M: Preparation of (±)-15-Bromo-19,20-dihydro-19,22-dioxo-28--5H,17H-3,5:18,21-diethano-6,10:12,16-dimetheno-22H-imidazo[3,4-h][8,11,14] oxatriazacycloeicosine-9-carbonitrile hydrochloride A suspension of product from Step L (37.0 mg, 0.0466 mmol), potassium fluoride (40 wt % on alumina, 21.0 mg, 0.146 mmol), and 18-crown-6 (1.20 mg, 0.00466 mmol) in acetonitrile (5 mL) was heated at 65° C. for 16 hours. The reaction was poured onto saturated aqueous sodium bicarbonate and extracted with methylene chloride (3×25 mL). The combined organic layers were washed with brine, dried over sodium sulfate, filtered, and concentrated in vacuo to provide a yellow oil. The crude product was purified by column chromatography (0→3% methanol/chloroform) and converted to the HCl salt to provide the title compound as a white solid. $^1$H NMR (DMSO) δ 8.01 (d, 1H, J=8.1 Hz); 7.97 (d, 1H, J=8.1 Hz); 7.69 (d, 1H, J=8.8 Hz); 7.68 (d, 1H, J=8.8 Hz); 7.66 (d, 1H, J=8.3 Hz); 7.61 (d, 2H, J=8.1 Hz); 7.57 (s, 1H); 7.44 (s, 1H); 7.19–7.22 (m, 2H); 6.73 (s, 1H); 6.23 (dd, 1H, J=8.2, 4.7 Hz); 6.06 (t, 1H, J=7.2 Hz); 5.85 (d, 1H, J=2.7 Hz); 5.79 (s, 1H); 5.10 (d, 1H, J=16.1 Hz); 5.06 (d, 1H, J=16.9 Hz); 4.60 (d, 1H, J=16.1 Hz); 4.46–4.56 (m, 3H); 4.30 (d, 1H, J=17.8 Hz); 4.21 (d, 1H, J=12.9 Hz); 3.62–3.92 (m, 5H); 3.43–3.49 (m, 1H); 3.26–3.32 (m, 3H); 3.01–3.12 (m, 3H). MS (es) m+1=537.

Step N: Separation of (R)-15-Bromo-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile hydrochloride and (S)-15-Bromo-19,20-dihydro-19,22-dioxo-28-thia-5H,17H-3,5: 18,21-diethano-6,10:12,16-dimetheno-22H-imidazo[3,4-h][1,8,11,14]oxatriazacycloeicosine-9-carbonitrile hydrochloride The racemate from Step M was resolved on a Chirose 1 (250×20 mm) column using a 10→100% isopropanol/n-butyl chloride gradient to elute the first enantiomer, followed by a 70% acetonitrile/isopropanol mobile phase to elute the second enantiomer. Each enantiomer eluted as two distinct and interconvertible peaks, which were combined.

Example 2

(R)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile hydrochloride and (S)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile hydrochloride

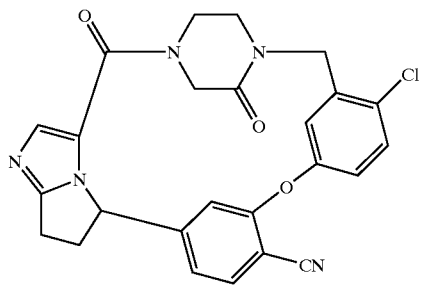

Step A: Preparation of 2-chloro-5-[(methanesulfonyl)-oxy]toluene

To a solution of 4-chloro-3-methylphenol (35.0 g, 277 mmol) in 100 mL of methylene chloride at 0° C. was added triethylamine (77.0 mL, 554 mmol), followed by methanesulfonyl chloride (32.2 mL, 416 mmol). The reaction was allowed to warm to room temperature for 1 hr. The solution was poured into EtOAc, washed with H$_2$O and brine, dried (Na$_2$SO$_4$), filtered, and concentrated in vacuo. The resulting yellow solid product was used without further purification.

Step B: Preparation of 3-(bromomethyl)-4-chlorophenyl methanesulfonate

To a solution of the product from step A (61.3 g, 301 mmol) in 500 ml of carbon tetrachloride was added N-bromosuccinimide (80.3 g, 451 mmol) and 2,2-azobisisobutyronitrile (7.40 g, 45.0 mmol). The reaction was stirred at 80° C. for 2.5 hr, concentrated in vacuo, and then suspended in 30% EtOAc/Hexane (300 mL). The solution was filtered and concentrated to give crude product. The crude product was purified by silica gel chromatography (20% EtOAc/Hexane) to provide the title product as a yellow oil Step C: Preparation of 4-[2-chloro-5-(methanesulfonyloxy)-benzyl]-3-oxo-piperazine-1-carboxylic acid tert-butyl ester To a solution of piperazin-3-one-1-carboxylic acid tert-butyl ester (7.10 g, 35.3 mmol) in dry DMF (200 mL) at 0° C. was added sodium hydride (60% dispersion in mineral oil, 2.10 g, 53.0 mmol). The reaction mixture was stirred for 15 min, and then a solution of the benzylbromide from Step B (10.0 g, 35.3 mmol) in DMF (50 mL) was added dropwise. The reaction mixture was allowed to warm to room temperature overnight. The reaction was poured into EtOAc (300 ml), and washed with H$_2$O (3×50 ml). The organic layer was dried with magnesium sulfate, filtered, and concentrated in vacuo. The crude product was purified by column chromatography (60% ethyl acetate/hexane) to provide the title compound as a yellow oil.

Step D: Preparation of 4-[2-chloro-5-(hydroxy)-benzyl]-3-oxo-piperazine-1-carboxylic acid tert-butyl ester A solution of product from step C (3.88 g, 9.65 mmol) and potassium t-butoxide (2.16 g, 19.3 mmol) in ethanol (100 mL) and H$_2$O (5 ml) was heated at reflux for 3 hours. The reaction was concentrated in vacuo and the residue was partitioned between EtOAc and sat. NH$_4$Cl. The organic layer was washed with H$_2$O and brine, dried over magnesium sulfate, and concentrated in vacuo to give title product which was sufficiently pure for use in the next step.

Step E: Preparation of 4-[2-chloro-5-(tert-butyldiphenylsilyloxy)-benzyl]-3-oxo-piperazine-1-carboxylic acid tert-butyl ester A solution of product from step D (2.75 g, 8.48 mmol), tert-butyldiphenylchlorosilane (2.20 mL, 8.48 mmol), and imidazole (860 mg, 12.7 mmol) in DMF (50 mL) was stirred at 60° C. for 15 hours. The reaction was poured into EtOAc (200 ml) and washed with H$_2$O (3×100 ml). The organic layer was dried with magnesium sulfate, filtered, and concentrated in vacuo. The crude product was purified by column chromatography (25–30% ethyl acetate/hexane) to provide the title compound.

Step F: Preparation of 1-[2-chloro-5-(tert-butyldiphenylsilyloxy)-benzyl]-piperazin-2-one To a solution of product from Step E (2.10 g, 3.74 mmol) in methylene chloride (20 mL) was added trifluoroacetic acid (4 mL). The resulting solution was stirred for 2 hours, then poured onto saturated aqueous sodium bicarbonate, and extracted with methylene chloride (3×50 mL). The combined organic layers were dried over magnesium sulfate, filtered, and concentrated in vacuo to provide the title product without further purification.

Step G: Preparation of 2-fluoro-4-[(2E)-3-(1-trityl-1H-imidazol-5-yl)prop-2-enoyl]benzonitrile To a solution of 4-cyano-3-fluoroacetophenone (Step F, Example 1, 4.02 g, 24.6 mmol) in dry THF (200 mL) at −78° C. was added lithium bis(trimethysilyl)amide (1.0 M in THF, 25.9 mL, 25.9 mmol) over 20 minutes. After the yellow reaction mixture was stirred for 1 hour at −78° C., a solution of 1-trityl-2-imidazolecarboxaldehyde (9.17 g, 27.1 mmol) in THF (300 mL) was added via cannula. After stirring for 12 hours at −78° C. and 4 hrs at 25° C., the reaction was pored onto brine (500 mL). The layers were separated and the aqueous layer was extracted with ethyl acetate (3×200 mL). The combined organic layers were dried ($Na_2SO_4$), filtered, and concentrated in vacuo. The crude product was purified by column chromatography (10→75% EtOAc/Hex) to provide the title compound as an orange solid.

Step H: Preparation of 2-fluoro-4-[(2E)-1-hydroxy-3-(1-trityl-1H-imidazol-5-yl)prop-2-enyl]benzonitrile To a solution of the product from Step G (8.89 g, 18.4 mmol) in methanol (200 mL)/methylene chloride (50 mL) at 0° C. was added sodium borohydride (695 mg, 18.4 mmol). After stirring for 1 hour, the reaction was quenched by the addition of sat. aq. $NH_4Cl$ until $H_2$ evolution ceased. The solvents were removed in vacuo and the residue was partitioned between methylene chloride (200 mL) and water (200 mL). The layers were separated and the aqueous layer was washed with methylene chloride (3×50 mL). The combined organic layers were dried ($Na_2SO_4$), filtered, and concentrated in vacuo to provide the title compound as a yellow oil which was sufficiently pure for use in the next step.

Step I: Preparation of 2-fluoro-4-[1-hydroxy-3-(1-trityl-1H-imidazol-5-yl)propyl]benzonitrile Product from Step 1 (8.93 g, 18.4 mmol), and 10% palladium on carbon (550 mg) were suspended in THF (200 mL)/water (20 mL) and placed under a hydrogen atmosphere (1 atm) for 7 hours. The reaction solution was filtered through a Celite pad and concentrated in vacuo to provide the title compound as a white foam which was sufficiently pure for use in the next step.

Step J: Preparation of 5-(4-cyano-3-fluorophenyl)-6,7-dihydro-5H-pyrrolo[1,2-a]imidazole To a solution of alcohol from Step 1 (8.14 g, 16.7 mmol) and N,N-diisopropylethylamine (4.36 mL, 25.0 mmol) in methylene chloride (200 mL) was added methanesulfonic anhydride (3.49 g, 20.0 mmol) at 0° C. The reaction was stirred for 2 hours at 0° C. and 2 hours at reflux, then concentrated in vacuo. The residue was dissolved in methanol (100 mL) and heated for 1.5 hours at 70° C. After concentrating in vacuo, the crude product was partitioned between saturated sodium bicarbonate (100 mL) and methylene chloride (100 mL). The layers were separated and the aqueous layer was extracted with methylene chloride (2×50 mL). The combined organic layers were dried ($Na_2SO_4$), filtered, and concentrated in vacuo. The residue was dissolved in acetonitrile (200 mL) and extracted with hexanes (12×100 mL), then concentrated to provide the title compound as a brown oil which was sufficiently pure for use in the next step.

Step K: Preparation of 5-(4-cyano3-fluorophenyl)-3-hydroxymethyl-6,7-dihydro-5H-pyrrolo[12-a]imidazole A solution of product from Step J (3.79 g, 16.7 mmol), sodium acetate (2.44 g, 29.7 mmol), acetic acid (1.82 mL, 31.9 mmol), and formaldehyde (37% in water, 15.1 mL) was heated to reflux for 96 hours. The reaction was slowly neutralized by the addition of sat. aq. $NaHCO_3$. The aqueous layer was extracted with methylene chloride (5×50 mL). The combined organic layers were dried ($Na_2SO_4$), filtered, and concentrated in vacuo. The crude product was purified by column chromatography (1→10% MeOH/$CHCl_3$) to provide the title compound as a white solid.

Step L: Preparation of 5-(4-cyano-3-fluorophenyl)-6,7-dihydro-5H-pyrrolo[1,2-a]imidazole-3-carboxaldehyde To a solution of oxalyl chloride (3.24 mL, 6.472 mmol) in methylene chloride (10 mL) at −78° C. was added DMSO (0.919 mL, 12.9 mmol). The solution was stirred for 15 minutes and a solution of the alcohol from Step K (1.11 g, 4.32 mmol) in methylene chloride (5 mL)/DMSO (1 mL) was added. The solution was stirred for an additional 15 minutes and then triethylamine (3.01 mL, 21.6 mmol) was added. The resulting solution was stirred for 5 minutes at −78° C. and 4 hours at 25° C. The reaction was poured onto sat. aq. $NaHCO_3$ and extracted with methylene chloride (3×20 mL). The combined organic layers were dried ($Na_2SO_4$), filtered, and concentrated in vacuo to provide the title product as a brown oil which was sufficiently pure for use in the next step.

Step M: Preparation of 5-(4-cyano-3-fluorophenyl)-6,7-dihydro-5H-pyrrolo[1,2-a]imidazole-3-carboxylic acid To a solution of aldehyde from Step L (990 mg, 3.88 mmol) in tert-butanol (20 mL)/2-methyl-2-butene (2 mL) was added a solution of sodium chlorite (421 mg, 4.65 mmol) and sodium dihydrogenphosphate monohydrate (642 mg, 4.65 mmol) in $H_2O$ (4 mL). The reaction mixture was stirred for 16 hours and the precipitate filtered to yield the title product as a white solid.

Step N: Preparation of 5-(1-{4-[2-chloro-5-(tert-butyldiphenyl-silyloxy)-benzyl]-3-oxo-piperazin-1-yl}-methanoyl)-3-(4-cyanophenyl)-6,7-dihydro-5H-pyrrolo[1,2-a]imidazole Carboxylic acid from Step M (1.02 g, 3.76 mmol), amine from Step F (1.80 g, 3.76 mmol), EDC hydrochloride (865 mg, 4.51 mmol), HOBT (610 mg, 4.51 mmol), and N,N-diisopropylethylamine (3.28 mL, 18.8 mmol) were stirred in dry DMF (20 mL) at 25° C. for 72 hours. The reaction was poured onto aq. $NaHCO_3$ (100 mL) and extracted with methylene chloride (3×50 mL). The combined organic layers were dried ($Na_2SO_4$), filtered, and concentrated in vacuo. The crude product was purified by column chromatography (1→5% MeOH/$CH_2Cl_2$) to provide the title compound as a yellow oil.

Step O: Preparation of 15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile hydrochloride A suspension of product from Step N (1.66 g, 2.27 mmol), potassium fluoride (40 wt % on alumina, 988 mg, 6.80 mmol), and 18-crown-6 (59.9 mg) in acetonitrile (200 mL) were heated at 80° C. for 16 hours. The reaction mixture was filtered and concentrated in vacuo. The crude product was purified by column chromatography (0→10% methanol/chloroform) and converted to the HCl salt to provide the title compound. $^1$H NMR (DMSO) δ 7.93 (d, 1H, J=7.9 Hz); 7.90 (d, 1H, J=8.0 Hz); 7.57 (s, 1H); 7.48–7.52 (m, 5H), 7.26 (s, 1H); 7.20–7.23 (m, 2H); 6.74 (s,1H); 5.69–5.85 (m, 6H); 5,12 (d, 1H, J=16.4 Hz); 5.06 (d, 1H, J=17.0 Hz); 4.57 (d, 1H, J=15.9 Hz); 4.29 (d, 1H, J=16.9 Hz); 4.20 (d, 1H, J=13.4Hz); 4.07 (q, 1H, J=5.2 Hz); 3.95–4.05 (m, 1H); 3.93 (d, 1H, J=16.4 Hz); 3.81 (d, 1H, J=17.1 Hz); 3.75–3.85 (m, 1H); 3.66 (d, 1H, J=16.0 Hz); 2.82–3.42 (m, 8H); 2.31–2.50 (m, 3H). Elemental analysis for $C_{25}H_{20}Cl_1N_5O_3$. 2.05 HCl. 0.70 $Et_2O$ calc. C, 55.60; H, 4.88; N, 11.66; found C, 55.69; H, 4.54; N, 11.52.

Step P: Separation of Enantiomers (R)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile hydrochloride and (S)-15-Chloro-19,20-dihydro-19,22-dioxo-5H, 17H-3,5:18,21-diethano-6,10:12,16-dimetheno-22H-imidazo[3,4-h][1,8,11,14]oxatriazacycloeicosine-9-carbonitrile hydrochloride The racemate from Step O was resolved on a Chirose I (250×20 mm) column using a 20/40/40% hexane/ethanol/methanol mobile phase for 30 minutes to elute the first enantiomer, then a 100% methanol mobile phase to elute the second enantiomer. Each enantiomer eluted as two distinct and interconvertible peaks, which were combined. Enantiomer A: FAB MS (MH+) calcd. for $C_{25}H_{21}Cl_1N_5O_3$ 474.1327, found 474.1315. Enantiomer B: FAB MS (MH+) calcd. for $C_{25}H_{21}Cl_1N_5O_3$ 474.1327, found 474.1320.

Example 3

15-Chloro-19,20-dihydro-19-oxo-5H, 17H-3,5:18, 21-diethano-6,10:12,16-dimetheno-22H-imidazo[3,4-h][1,8,11,14]oxatriazacycloeicosine-9-carbonitrile bishydrochloride

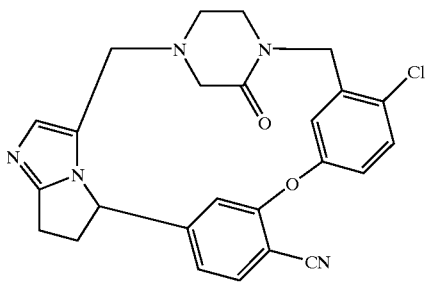

Step A: Preparation of 3-{1-[4-(2-chloro-5-(tert-butyldiphenyloxy)benzyl)piperazin-3-on-1-yl]-methanoyl}-5-(4-cyano-3-fluorophenyl)-6,7-dihydro-5H-pyrrolo[1,2-a]imidazole To a solution of aldehyde from Step L, Example 2 (110 mg, 0.432 mmol) and piperazinone from Step F, Example 2 (206 mg, 0.432 mmol) in dichloroethane (3 mL) was added a few drops of acetic acid. The reaction solution was stirred for 3 hours, and then sodium triacetoxyborohydride (100 mg, 0.474 mmol) was added. The reaction mixture was stirred for 16 hours and then poured onto aq. NaHCO₃ (20 mL) and extracted with methylene chloride (3×10 mL). The combined organic layers were dried (Na₂SO₄), filtered, and concentrated in vacuo. The crude product was purified by column chromatography (0→5% MeOH/CH₂Cl₂) to provide the title compound as a white solid.

Step B: Preparation of 15-Chloro-19,20-dihydro-19-oxo-5H,17H-3,5:18,21-diethano-6,10:12,16-dimetheno-22H-imidazo[3,4-h][1,8,11,14]oxatriazacycloeicosine-9-carbonitrile bishydrochloride A suspension of product from Step A (105 mg, 0.146 mmol), potassium fluoride (40 wt % on alumina, 63.7 mg, 0.438 mmol), and 18-crown-6 (3.86 mg) in acetonitrile (15 mL) were heated at 90° C. for 48 hours. The reaction mixture was filtered and concentrated in vacuo. The crude product was purified by column chromatography (0→10% methanol/chloroform) and converted to the HCl salt to provide the title compound. $^1$H NMR δ 8.02 (d, 1H, J=7.9 Hz); 7.96 (d, 1H, J=8.1 Hz); 7.73 (s, 1H); 7.66 (s, 1H); 7.63 (s, 1H); 7.59 (s, 1H); 7.56 (d, 1H, J=8.6 Hz); 7.50 (d, 1H, J=8.6 Hz); 7.35 (d, 1H, J=8.3 Hz); 7.29 (dd, 1H, J=8.6, 3.3 Hz); 7.23 (dd, 1H, J=8.6, 3.3 Hz); 6.62 (bs, 1H); 6.24 (s, 1H); 5.85 (s, 1H); 5.78–5.82 (m, 1H); 5.53 (t, 1H, J=7.8 Hz); 5.06 (d, 1H, J=17.2 Hz); 5.02 (d, 1H, J=17.6 Hz); 3.8 (d, 1H, J=16.8 Hz); 3.74 (d, 1H, J=17.4 Hz); 3.35 (s, 2H); 2.99–3.26 (m, 10H); 2.34–2.87 (m, 12H). FAB MS (MH+) calcd. for $C_{25}H_{23}Cl_1N_5O_2$ 460.1535, found 460.1543.

Example 4

19,20-Dihydro-19,22-dioxo-5H-3,5:18,21-diethano-12,14-etheno-6,10-metheno-benzo[d]imidazo[4,3-k][1,6,9,12]oxatriazacyclooctadecine-9-carbonitrile hydrochloride

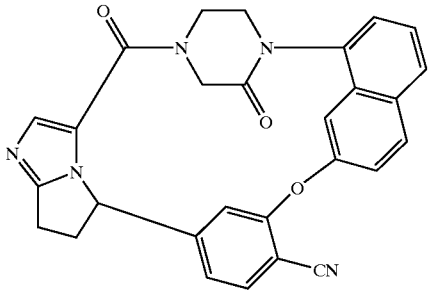

Step A: Preparation of 2-chloro-N-(7-hydroxynaphthalen-1-yl)acetamide

To a solution of 8-amino-2-naphthol (8.00 g, 50.3 mmol) in 500 mL of EtOAc and 500 mL of saturated NaHCO₃ solution at 0° C. was added chloroacetyl chloride (4.40 mL, 55.2 mmol). After 2 hours, the layers were separated, and the aqueous layer was extracted with EtOAc. The combined organics were washed with brine, dried (Na₂SO₄), filtered, and concentrated in vacuo. The titled product was obtained as a dark brown solid which was used in the next reaction without further purification.

Step B: Preparation of methanesulfonic acid 8-(2-chloroacetylamino)naphthalen-2-yl ester To a solution of the crude alcohol from Step A (50.3 mmol) in 150 mL of DMF at 0° C. was added triethylamine (15.0 mL, 108 mmol), followed by dropwise addition of methanesulfonyl chloride (6.0 mL, 77.5 mmol). After 16 hours, additional portions of triethylamine (7.0 mL, 50 mmol) and methanesulfonyl chloride (3.0 mL, 39 mmol) were added. After 4 hours, the solution was concentrated in vacuo and partitioned between EtOAc and saturated NH₄Cl solution. The organic layer was extracted with saturated NaHCO₃ solution and brine, dried (Na₂SO₄), filtered, and concentrated in vacuo to provide a dark purple solid.

Step C: Preparation of methanesulfonic acid 8-(2-hydroxyacetylamino)naphthalen-2-yl ester To a solution of ester from Step B (11.0 g, 39.5 mmol) in 150 mL of i-PrOAc at room temperature was added ethanolamine (12.0 mL, 199 mmol). After 18 hours, the reaction was partitioned between EtOAc and water, and the organic layer was extracted with saturated brine, dried (Na₂SO₄), filtered, and concentrated in vacuo to provide a dark oil.

Step D: Preparation of methanesulfonic acid 8-(2-oxopiperazin-1-yl)naphthalen-2-yl ester hydrochloride To a solution of product from Step C (9.96 g, 29.4 mmol) in 60 mL of EtOAc at 0° C. was added tri-n-butylphosphine (10.3 mL, 41.3 mmol). A solution of di-tert-butylazodicarboxylate (9.51 g, 41.3 mmol) in 45 mL of EtOAc was added dropwise. After 15 minutes, the reaction was warmed to 40° C. After complete consumption of starting material, a solution of ethanolic HCl was added (34.9 mmol of 1.63 M), and the mixture was slowly cooled to 0° C. over one hour. After stirring for one hour, the suspension was filtered through fritted glass. The mother liquor was concentrated and filtered to provide more material. The combined solids were dried in vacuo to give the title compound as a brown powder.

Step E: Preparation 3-{1-[4-(7-{methanesulfonyloxy}-naphth-1-yl)piperazin-3-on-1-yl]-methanoyl}-5-(4-cyano-3-fluorophenyl)-6,7-dihydro-5H-pyrrolo[1,2-a]imidazole Carboxylic acid from Step K, Example 2 (21.8 mg, 0.0804 mmol), amine from Step D (28.7 mg, 0.0804 mmol), EDC hydrochloride (30.8 mg, 0.161 mmol), HOBT (21.7 mg, 0.161 mmol), and N,N-diisopropylethylamine (0.070 mL, 0.402 mmol) were stirred in dry DMF (1 mL) at 25° C. for 18 hours. The reaction was poured onto aq. NaHCO$_3$ (20 mL) and extracted with methylene chloride (3×10 mL). The combined organic layers were dried (Na$_2$SO$_4$), filtered, and concentrated in vacuo. The crude product was purified by column chromatography (0→10% MeOH/CH$_2$Cl$_2$) to provide the title compound as a yellow oil.

Step F: Preparation of 19,20-Dihydro-19,22-dioxo-5H-3,5:18,21-diethano-12,14-etheno-6,10-metheno-benzo[d]imidazo[4,3-k][1,6,9,12]oxatriazacyclooctadecine-9-carbonitrile hydrochloride A suspension of product from Step E (29.0 mg, 0.0506 mmol) and cesium carbonate (82.4 mg, 0.253 mmol) in DMSO (5 mL) were heated at 70° C. for 16 hours. The reaction was poured onto brine (20 mL) and extracted with methylene chloride (3×10 mL). The combined organic layers were dried (Na$_2$SO$_4$), filtered, and concentrated in vacuto. The crude product was purified by column chromatography (0→10% MeOH/CH$_2$Cl$_2$) and converted to the HCl salt to provide the title compound as a white solid. $^1$H NMR (DMSO) δ 8.07–8.19 (m, 4H); 7.90–7.98 (m, 5H); 7.43–7.7.63 (m, 9H); 6.42 (s, 1H); 6.24 (s, 1H); 5.92 (t, 2H, J=7.8 Hz); 4.82 (bd, 1H, J=17.3 Hz); 4.61 (d, 1H, J=15.4 Hz); 4.50 (bd, 1H, J=15.4 Hz); 4.32 (bd, 1H, J=11.7 Hz); 4.00–4.10 (m, 4H); 3.92 (d, 1H, J=15.6 Hz); 3.10–3.35 (m, 11H).

Example 5

22,23-Dihydro-22-oxo-31-thia-5H-3,5:21,24-diethano-6,10:12,16-dimetheno-12H, 25H-benzo[g]imidazo[4,3-n][1,8,11,14]oxatriazacycloheneicosine-9-carbonitrile.

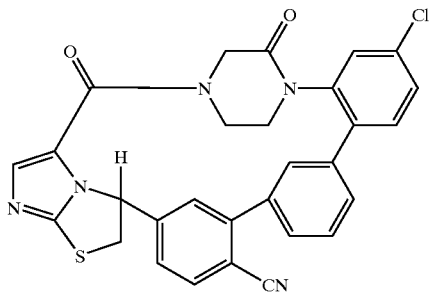

Step A: Preparation of 2-(3-Methoxyphenyl)nitrobenzene
3-Methoxyphenyl boronic acid (7.4 g, 48.71 mmol), 1-bromonitro-benzene (10.25 g, 40.59 mmol) and K$_2$CO$_3$ (28.05 g, 202.9 mmol) were dissolved in H$_2$O (85 mL) and ethylene glycol dimethyl ether (170 mL). The solution was degassed, Pd(PPh$_3$)$_4$ (1.7 g, 1.50 mmol) was added and the vessel was heated to 110° C. under argon for 5 hours. The reaction was cooled, diluted with water and extracted with EtOAc (3×). The combined organic extracts were dried over Na$_2$SO$_4$, filtered and concentrated in vacuo. The residue was crystallized from EtOAc/Hex. The mother liquor was concentrated in vacuo and chromatographed on silica gel, eluting with a gradient of 1 to 10% EtOAc in hexanes, to yield the above-titled compound.

Step B: Preparation of 2-(3-Hydroxyphenyl)nitrobenzene
2-(3-Methoxyphenyl)nitrobenzene, as described above in Step A, (8.6 g, 37.52 mmol) was dissolved in CH$_2$Cl$_2$ (500 mL) and cooled to −78° C. BBr$_3$ (1.0M sol. in CH$_2$Cl$_2$, 43 mL, 43 mmol) was slowly added and the reaction was warmed to ambient temperature and stirred for 18 hours. The reaction was partitioned between saturated aqueous NaHCO$_3$ and CH$_2$Cl$_2$ and extracted with CH$_2$Cl$_2$ (3×). The combined organic extracts were dried over Na$_2$SO$_4$, filtered and concentrated in vacuo, to yield the above-titled compound.

Step C: Preparation of 2-(3-tert-Butyldimethylsilyloxyphenyl)nitrobenzene
2-(3-Hydroxyphenyl)nitrobenzene, as described above in Step B, (8.07 g, 37.52 mmol), imidazole (7.66 g, 112.56 mmol) and tert-butyldimethylsilyl chloride (6.22 g, 41.27 mmol) were dissolved in DMF (30 mL) and stirred for 0.75 hour. The DMF was removed in vacuo and the resulting residue was taken up in water and dimethyl ether and extracted with dimethyl ether (3×). The combined organic extracts were dried over Na$_2$SO$_4$, filtered and concentrated in vacuo. The residue was chromatographed on silica gel, eluting with a gradient of 0%→4% EtOAc in hexanes, to yield the above-titled compound.

Step D: Preparation of 2-(3-tert-Butyldimethylsilyloxyphenyl)aniline
2-(3-tert-Butyldimethylsilyloxyphenyl)nitrobenzene from Step C, (11.94 g, 36.24 mmol) was dissolved in EtOH (250 mL) and EtOAc (250 mL), degassed with argon and Pd/C (1.19 g, 10 wt %) was added. The vessel was subjected to H$_2$ (1 atm) while vigorously stirring for 2.5 hour. The reaction was filtered through a celite pad and concentrated in vacuo, to yield the above-titled compound.

Step E: Preparation of N'-[(3'-tert-butyldimethylsilyloxy)-1,1'-biphenyl-2-yl)]-N''-(2-hydroxyethyl)glycinamide
To a solution of product from step D (1.2 g, 4.39 mmol) in 10 mL of 1:1 isopropyl acetate/saturated NaHCO$_3$ solution was added chloroacetyl chloride dropwise (0.52 mL, 6.59 mmol). After 30 min, the layers were separated, and the organic layer was placed back in the reaction flask. Then, ethanol amine was added slowly (1.06 mL, 17.6 mmol). Reaction was stirred at RT for 2 hr, at 60° C. for 1 hr, and 45° C. overnight. Reaction was concentrated in vacuo. The resulting material was partitioned between EtOAc and water, washed with brine, dried (MgSO$_4$), filtered, and concentrated in vacuo. The resulting product was used without further purification.

Step F: Preparation of 1-[(3'-tert-butyldimethylsilyloxy)-1,1'-biphenyl-2-yl]piperazin-2-one
To a solution of the product from Step E (1 g, 3.81 mmol) in 10 mL of tetrahydrofuran was added tributylphosphine (1.3 mL, 5.7 mmol). After cooling to 0° C., di-tert-butylazodicarboxylate (1.2 g, 5.7 mmol) was added, and the reaction was allowed to come to room temperature overnight. The solution was concentrated in vacuo, partitioned between EtOAc and water, washed with brine, dried (MgSO$_4$), filtered, and concentrated in vacuo to provide the titled product (2.5.0 g). The crude product was purified by silica gel chromatography (1→10% MeOH/CHCl$_3$) to provide the pure titled product along with impure fractions.

Step G: Preparation of 3-(4-cyano-3-fluorophenyl)-2,3-dihydro-imidazo[2,1-b]thiazole-5-carboxylic acid hydrochloride Prepared as described in Steps F,G,H,I, J, K in Example 1.

Step H: Preparation of 5-(1-{4-[(3'-tert-butyldimethylsilyloxy)-1,1'-biphenyl]3-oxo-piperazin-2-yl}-methanoyl)-3-(4-cyano-3-fluorophenyl)-2,3-dihydro-imidazo[2,1-b]thiazole The carboxylic acid from Step G (180 mg, 0.62 mmol), the piperazinone from Step F (240 mg, 0.62 mmol), EDC hydrochloride (240 mg, 1.20 mmol), HOBT (84 mg, 0.62 mmol), and Et$_3$N (0.430 mL, 3.1 mmol) were stirred together in dry, degassed DMF (6 mL) at 25° C. for 2 hours. The reaction was poured onto EtOAc and washed with H2O. The organic layers were washed with brine, dried over sodium sulfate, filtered, and concentrated in vacuo. The crude product was purified by column chromatography (1–3% methanol/methylene chloride) to provide the title compound.

Step I: Preparation of 22,23-Dihydro-22-oxo-31-thia-5H-3,5:21,24-diethano-6,10:12,16-dimetheno-12H, 25H-benzo[g]imidazo[4,3-n][1,8,11,14]oxatriazacycloheneicosine-9-carbonitrile A suspension of product from Step H (250 mg, 0.38 mmol), potassium fluoride (40 wt % on alumina, 166 mg, 1.147 mmol), and 18-crown-6 (80 mg, 0.38 mmol) in acetonitrile (5 mL) was heated at 80° C. for 6 hours. The reaction was concentrated in vacuo to provide a yellow oil. The crude product was purified by column chromatography (1→3% methanol/methylene chloride) to yield the racemic product.

Step J: Preparation of enantiomer A and enantiomer B of 22,23-Dihydro-22-oxo-31-thia-5H-3,5:21,24-diethano-6,10:12,16-dimetheno-12H, 25H-benzo[g]imidazo[4,3-n][1,8,11,14]oxatriazacycloheneicosine-9-carbonitrile The racemate from Step I was resolved on a chiralpak OD (250×4.6 mm) column using 20% hexane+0.1% DEA in methanol. Enantiomer A (unknown absolute stereochemistry) was obtained by combining the two distinct and interconvertible peaks (first and last peaks). Enantiomer B was obtained from the two middle peaks. High Res Mass calculated for: $C_{29}H_{22}N_5O_3S_1$ (M+1): 520.1438. Found: 520.1436 (M+1).

Example 6

15-Fluoro-19,20-dihydro-19,22-dioxo-28-5H,17H-3,5:18,21-diethano-6,10:12,16-dimetheno-22H-imidazo[3,4-h][1,8,11,14]oxatriazacycloeicosine-9-carbonitrile hydrochloride

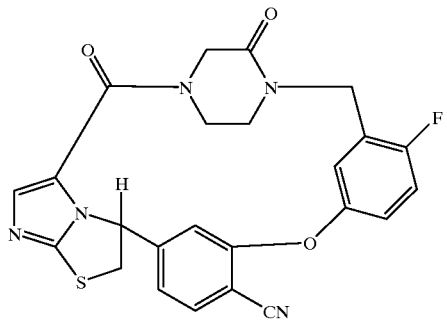

Step A: Preparation of 2-fluoro-5-[(methanesulfonyl)-oxy]toluene

To a solution of 4-fluoro-3-methylphenol (35.0 g, 277 mmol) in 100 mL of methylene chloride at 0° C. was added triethylamine (77 mL mL, 554 mmol), followed by methanesulfonyl chloride (32.2 mL, 416 mmol). The reaction was allowed it to warm to room temperature and stirred at room temperature for 1 hr. The solution was poured into EtOAc, washed with H$_2$O and brine, dried (Na$_2$SO$_4$), filtered, and concentrated in vacuo. The resulting yellow solid product was used without further purification.

Step B: Preparation of 4-fluoro-1-(methanesulfonyloxy)-3-methylbromide

To a solution of the product from Step A (61.3 g, 300.5 mmol) in 500 mL of carbon tetrachloride were added N-bromosuccinimide (80.3 g, 450.7 mmol) and 2,2-azobisisobutyronitrile (7.4 g, 45 mmol). Reaction was stirred at 80° C. for 2.5 hours. Reaction was concentrated in vacuo, and then suspended in 30% EtOAc/Hexane (300 mL). The solid was filtered off and the filtrate was concentrated to give crude product. The crude product was purified by silica gel chromatography (20% EtOAc/Hexane) provided title product as a yellow oil Step C: Preparation of 4-[2-fluoro-5-(methanesulfonyloxy)-benzyl]-3-oxo-piperazine-1-carboxylic acid tert-butyl ester To a solution of piperazin-3-one-1-carboxylic acid tert-butyl ester (7.1 g, 35.3 mmol) in dry DMF (200 mL) at 0° C. was added sodium hydride (60% dispersion in mineral oil, 2.1 g, 53 mmol). The reaction mixture was stirred for 15 min, and then a solution of the benzylbromide from Step B (10 g, 35.3 mmol) in DMF (50 mL) was added dropwise. The reaction mixture was allowing to warm to room temperature overnight. The reaction was poured into EtOAc (300 mL), and washed with H$_2$O (3×150 mL). The organic layer was dried with magnesium sulfate, filtered, and concentrated in vacuo. The crude product was purified by column chromatography (60% ethyl acetate/hexane) to provide the title compound as a yellow oil.

Step D: Preparation of 4-[2-fluoro-5-(hydroxy)-benzyl]-3-oxo-piperazine-1-carboxylic acid tert-butyl ester A solution of product from Step C (3.88 g, 9.65 mmol), potassium t-butoxide (2.16 g, 19.3 mmol) in ethanol (100 mL) and H$_2$O (5 mL) was heated at reflux for 3 hours. The reaction was concentrated in vacuo and the residue was partitioned between EtOAc and sat. NH$_4$Cl. The organic layer was washed with H$_2$O, and brine and then dried over magnesium sulfate and concentrated in vacuo to give title product which was sufficiently pure for use in the next step.

Step E: Preparation of 4-[2-fluoro-5-(tert-butyldiphenylsilyloxy)-benzyl]-3-oxo-piperazine-1-carboxylic acid tert-butyl ester A solution of product from Step D (2.75 g, 8.48 mmol), tert-butyldiphenylchlorosilane (2.2 mL, 8.48 mmol), and imidazole (860 mg, 12.7 mmol) in DMF (50 mL) was stirred at 60° C. for 15 hours. The reaction was poured into EtOAc (200 mL), and washed with H$_2$O (300×100 mL). The organic layer was dried with magnesium sulfate, filtered, and concentrated in vacuo. The crude product was purified by column chromatography (25–30% ethyl acetate/hexane) to provide the title compound.

Step F: Preparation of 1-[2-fluoro-5-(tert-butyldiphenylsilyloxy)-benzyl]-piperazin-2-one To a solution of product from Step E (2.1 g, 3.74 mmol) in methylene chloride (20 mL) was added trifluoroacetic acid (4 mL). The resulting solution was stirred for 2 hours, then poured onto saturated aqueous sodium bicarbonate, and extracted with methylene chloride (3×50 mL). The combined organic layers were dried over magnesium sulfate, filtered, and concentrated in vacuo to provide the title product without further purification.

Step G: Preparation of 3-(4-cyano-3-fluorophenyl)-2,3-dihydro-imidazo[2,1-b]thiazole-5-carboxylic acid hydrochloride Prepared as described in Steps F,G,H,I, J, K in Example 1.

Step H: Preparation of 5-(1-{4-[2-fluoro-5-(tert-butyldiphenyl-silyloxy)-benzyl]-3-oxo-piperazin-1-yl}-methanoyl)-3-(4-cyanophenyl)-2,3-dihydro-imidazo[2,1-b]thiazole The carboxylic acid from Step G (180 mg, 0.62 mmol), the piperazinone from Step F (288 mg, 0.62 mmol), EDC hydrochloride (240 mg, 1.24 mmol), HOBT (84 mg, 0.62 mmol), and Et$_3$N(0.430 mL, 3.1 mmol) were stirred together in dry, degassed DMF (6 mL) at 25° C. for 2 hours. The reaction was poured onto EtOAc and washed with H2O. The organic layers were washed with brine, dried over sodium sulfate, filtered, and concentrated in vacuo. The crude product was purified by column chromatography (1–5% methanol/methylene chloride) to provide the title compound.

Step I: Preparation of 15-Fluoro-19,20-dihydro-19,22-dioxo-28–5H,17H-3,5:18,21-diethano-6,10:12,16-dimetheno-22H-imidazo[3,4-h][1,8,11,14] oxatriazacycloeicosine-9-carbonitrile hydrochloride A suspension of product from Step H (250 mg, 0.34 mmol), potassium fluoride (40 wt % on alumina, 200 mg, 1.36 mmol), and 18-crown-6 (90 mg, 0.34 mmol) in acetonitrile (7 mL) was heated at 80° C. for 5 hours. The reaction was concentrated in vacuo to give crude product which was purified by column chromatography (1→3% methanol/methylene chloride) and converted to HCl salt to provide the title compound as a white solid. High Res. Mass calculated C$_{24}$H$_{18}$F$_1$N$_5$O$_3$S$_1$ for (M+1): 476.1187. Found: 476.1202 (M+1).

Example 7

(R)-15-Chloro-19,20-dihydro-19,22-dioxo-28-thia-5H,17H-3,5:18,21-diethano-6,10:12,16-dimetheno-22H-imidazo[3,4-h][1,8,11,14] oxatriazacycloeicosine-9-carbonitrile hydrochloride and (S)-15-Chloro-19,20-dihydro-19,22-dioxo-28-thia-5H,17H-3,5:18,21-diethano-6,10:12,16-dimetheno-22H-imidazo[3,4-h][1,8,11,14] oxatriazacycloeicosine-9-carbonitrile hydrochloride

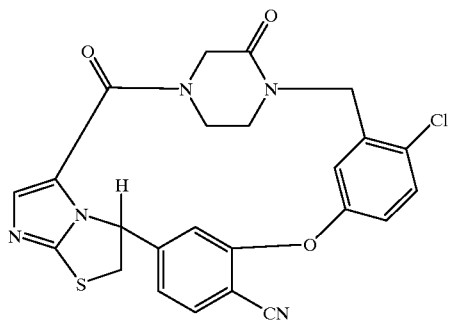

Step A: Preparation of 2-chloro-5-[(methanesulfonyl)-oxy] toluene

The title compound was prepared form 4-chloro-3-methylphenol using the procedure described in Step A of Example 6.

Step B: Preparation of 4-chloro-1-(methanesulfonyloxy)-3-methylbromide

The product from Step A was brominated using the procedure described in Step B of Example 6.

Step C: Preparation of 4-[2-chloro-5-(methanesulfonyloxy)-benzyl]-3-oxo-piperazine-1-carboxylic acid tert-butyl ester The title compound was prepared from the product of Step B (5.4 g, 27.1 mmol) using the procedure described in Step C of Example 6. The crude product was purified by column chromatography (60% ethyl acetate/hexane) to provide the title compound as a yellow oil.

Step D: Preparation of 4-[2-chloro-5-(hydroxy)-benzyl]-3-oxo-piperazine-1-carboxylic acid tert-butyl ester The title compound was prepared from the product of Step C (5.67 g, 13.56 mmol) using the procedure described in Step D of Example 6.

Step E: Preparation of 4-[2-chloro-5-(tert-butyldiphenylsilyloxy)-benzyl]-3-oxo-piperazine-1-carboxylic acid tert-butyl ester The title compound was prepared from the product of Step D (4.65 g, 13.67 mmol) using the procedure described in Step E of Example 6.

Step F: Preparation of 1-[2-chloro-5-(tert-butyldiphenylsilyloxy)-benzyl]-piperazin-2-one The title compound was prepared from the product of Step D (700 mg, 1.2 mmol) using the procedure described in Step F of Example 6.

Step G: Preparation of 3-(4-cyano-3-fluorophenyl)-2,3-dihydro-imidazo[2,1-b]thiazole-5-carboxylic acid hydrochloride Refer to Steps F,G,H,I, J, K in Example 1.

Step H: Preparation of 5-(1-{4-[2-chloro-5-(tert-butyldiphenyl-silyloxy)-benzyl]-3-oxo-piperazin-1-yl}-methanoyl)-3-(4-cyanophenyl)-2,3-dihydro-imidazo[2,1-b]thiazole The title compound was prepared from the products of Step F (534 mg, 1.15 mmol) and Step G (333 mg, 1.15 mmol) using the procedure described in Step H of Example 6. The crude product was purified by column chromatography (1–3% methanol/methylene chloride) to provide the title compound.

Step I: Preparation of 15-Chloro-19,20-dihydro-19,22-dioxo-28-thia-5H,17H-3,5:18,21 -diethano-6,10:12,16-dimetheno-22H-imidazo[3,4-h][1,8,11,14] oxatriazacycloeicosine-9-carbonitrile A suspension of product from Step H (685 mg, 0.91 mmol), potassium fluoride (40 wt % on alumina, 530 mg, 3.65 mmol), and 18-crown-6 (48 mg, 0.18 mmol) in acetonitrile (18 mL) was heated at 80° C. for 12 hours. The reaction was concentrated in vacuo to give crude product which was purified by column chromatography (0→10% methanol/methylene chloride) to give title product. High Res Mass calculated for: C$_{24}$H$_{18}$N$_5$O$_3$S$_1$Cl$_1$ (M+1): 492.0892. Found: 492.0895 (M+1).

Step J: Preparation of enantiomer A and enantiomer B of (±)-15-Chloro-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile The racemate from Step I was resolved on a Chirose I (250×20 mm) column using 30/35/35%→0/60/40% of hexane+0.1% DEA/MeOH/EtOH in 90 minutes. Enantiomer A (unknown absolute stereochemistry) was obtained by combining the first two distinct and interconvertible peaks, which was converted to HCl salt. Enantiomer B was obtained from the last two peaks, which was converted to HCl salt.

Example 8

19,20-Dihydro-19-oxo-30-thia-5H-3,5:18,21-diethano-12,14-etheno-6,10-metheno-benzo[d] imidazo[4,3-1[]1,6,9,13]oxatriazacyclononadecine-9-carbonitrile

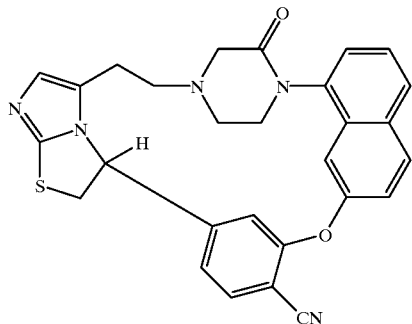

Step A: Preparation of 4-cyano-3-fluoroacetophenone

A solution of 4-bromo-3-fluorobenzonitrile (20 g, 99.79 mmol), tributyl(1-ethoxyvinyl)tin (39.64 g, 109.77 mmol), and dichloro-bis(triphenylphosphine) palladium (II) (700 mg, 0.504 mmol) in toluene (350 mL) was heated at reflux for 2 hours. The reaction mixture was cooled to room temperature and treated with 5% HCl (200 mL) for 120 hours. The reaction was poured onto water and extracted with ethyl acetate (3×200 mL). The combined organic layers were dried over magnesium sulfate, filtered, and concentrated in vacuo to provide a yellow oil. The crude product was purified by column chromatography (0→30% ethyl acetate/hexane) to provide the title compound as a white solid which was sufficiently pure for use in the next step.

Step B: Preparation of 4-cyano-3-fluorophenacyl bromide

To a solution of product from Step A (16 g, 98 mmol) in dioxane (250 mL) open to the atmosphere was added bromine (5.3 mL, 106.9 mmol) dropwise. The resulting orange solution was stirred until it turned yellow (1.5 hours). The reaction mixture was then concentrated to provide crude product which was purified by column chromatography 20% ethyl acetate/hexane) to provide the title compound.

Step C: Preparation of 4-[tert-butyloxycarbonylamino) ethyl]-2-mercapto-1H-imidazole To a solution of 1,4-diamino-2-ketobutane (9.56 g, 54.57 mmol) in 10 mL of H$_2$O was added potassium thiocyanate (5.3 g, 54.57 mmol). The reaction was heated to 100° C. in open air for 2 hours. 100 mL of ethanol was added and reaction was cooled to 0° C. Triethylamine (22.7 mL, 163.7 mmol) was added followed by di-tert-butyl-dicarbonate (11.91 g, 54.57 mmol) (in portions). The reaction was warmed to room temperature and stirred at room temperature for 30 minutes. The reaction was concentrated in vacuo then taken up in EtOAc which was washed with H$_2$O (2×),and brine (1×). The organic layers were dried over magnesium sulfate, filtered, and concentrated in vacuo to provide the title compound as a light yellow solid, which was sufficiently pure without further purification.

Step D: Preparation of 4-[tert-butyloxycarbonylamino) ethyl]-2-{([2-(4-cyano-3-fluorophenyl)-2-oxoethyl] thio}-1H-imidazole To a suspension of product from Step C (5.22 g, 21.48 mmol) in acetonitrile (50 mL) was added potassium carbonate (6 g, 43.4 mmol) followed by the product from Step B (5.2, 21.4 mmol). The reaction was stirred at room temperature for 20 minutes and concentrated in vacuo. The residual was partitioned between EtOAc and H$_2$O. The H$_2$O layer was extracted with EtOAc (2×). The combined organic layer was washed with brine (1×), dried over magnesium sulfate, filtered, and concentrated in vacuo to give the crude product. The crude product was purified by silica gel chromatography using 5% methanol/methylene chloride to provide the title product as an orange solid.

Step E: Preparation of 4-[tert-butyloxycarbonylamino) ethyl]-2-{[2-(4-cyano-3-fluorophenyl)-2-hydroxyethyl] thio}-1H-imidazole To a solution of the product from Step D (7.44 g, 18.4 mmol) in methanol (160 mL) at 0° C. was added sodium borohydride (700 mg, 18.4 mmol). The reaction was stirred at 0° C. for 20 minutes and quenched with sat. NH$_4$Cl (40 mL). The reaction was concentrated. The residual was taken up in EtOAc, washed with H$_2$O (2×), brine (1×) and dried over magnesium sulfate. The EtOAc solution was concentrated in vacuo to give the title compound that was sufficiently pure for use in the next step.

Step F: 5-[(2-tert-butoxycarbonylamino)ethyl]-3-(4-cyano-3-fluorophenyl)-2,3-dihydro-imidazo[2,1-b]thiazole To a solution of the product from Step E (9.46 g, 23.3 mmol) in methylene chloride (200 mL) was added methanesulfonic anhydride (8.1 g, 46.6 mmol), and DIEA (10 mL, 104.5 mmol). The reaction was heated at 55° C. for 120 hours. The reaction was diluted with methylene chloride, washed with sat. NaHCO$_3$ (1×), H$_2$O (1×), brine (1×), dried over magnesium sulfate, and concentrate in vacuo. The crude product was purified by silica gel chromatography (0→5% methanol/methylene chloride to provide the title product as a yellow solid.

Step G: 5-(Aminoethyl)-3-(4-cyano-3-fluorophenyl)-2,3-dihydro-imidazo[2,1-b]thiazole To a solution of product from Step F (2.5 g, 3.74 mmol) in methylene chloride (14 mL) was added trifluoroacetic acid (7 mL). The resulting solution was stirred for 2 hours, then poured onto saturated aqueous sodium bicarbonate, and extracted with methylene chloride (3×50 mL). The combined organic layers were dried over magnesium sulfate, filtered, and concentrated in vacuo to provide the title product without further purification.

Step H: Preparation of 1-(chloroacetamido)-7-hydroxynaphthalene

To a solution of 8-amino-2-naphthol (10.0 g, 62.8 mmol) in 240 mL of 1:1 EtOAc/saturated NaHCO$_3$ solution was added chloroacetyl chloride dropwise (5.5 mL, 69.1 mmol). After 20 minutes, the solution was filtered, the layers were separated, and the aqueous layer was extracted with EtOAc. The combined organic layers were washed with brine, dried (Na$_2$SO$_4$), filtered, and concentrated in vacuo to provide the titled product.

Step I: Preparation of 1-(chloroacetamido)-7-(tert-butyldiphenylsilyoxy)naphthalene A solution of product from Step H (13.6 g, 57.87 mmol), tert-butyldiphenylchlorosilane (14.86 mL, 69.45 mmol), and imidazole (5.9 g, 86.8 mmol) in DMF (250 mL) was stirred at room temperature for 72 hours. The reaction was poured into EtOAc (200 mL), and washed with H$_2$O (3×100 mL). The organic layer was dried with magnesium sulfate, filtered, and concentrated in vacuo. The crude product was purified by column chromatography (15% ethyl acetate/hexane) to provide the title compound as a brown solid.

Step J: Preparation of 1-{[3-(4-cyano-3-fluorophenyl)-2,3-dihydro-imidazo[2,1-b]thiazol-5-yl]-2-ethylamino}acetamido-7-(tert-butyldiphenylsilyloxy) naphthalene To a solution of the product from Step G (700 mg, 2.43 mmol) in 25 mL of acetonitrile at 0° C. was added diisopropylethylamine (0.422 mL, 2.43 mmol). After 10 minutes the solution of the product from Step I (864 mg, 2.21 mmol) in 10 mL of acetonitrile was added to the reaction dropwise. The reaction was stirred at room temperature for 48 hours, then concentrated in vacuo. The resulting material was partitioned between EtOAc and water, washed with brine, dried (MgSO$_4$), filtered, and concentrated in vacuo. The crude product was purified by silica gel chromatography (5% methanol/methylene chloride to give the title product.

Step K: Preparation of 1-{N-2-hydroxyethyl[3-(4-cyano-3-fluorophenyl)-2,3-dihydro-imidazo[2,1-b]thiazol-5-yl]2-ethylamino}acetamido-7-(tert-butyldiphenylsilyloxy) naphthalene To a solution of the crude product from Step J (460 mg, 0.72 mmol) in 5 mL of methanol was added glycol aldehyde (106 mg, 0.88 mmol), and sodium cyanoborohydride (68 mg, 1.07 mmol). The reaction was stirred at room temperature for 25 hours, then concentrated in vacuo. The resulting material was partitioned between EtOAc and water, washed with brine, dried (MgSO$_4$), filtered, and concentrated in vacuo to provide the titled product.

Step L: Preparation of 1-[7-(tert-butyldiphenylsilyoxy) naphthyl]-4-[3-[(4-cyano-3-fluorophenyl)-2,3-dihydro-imidazo[2,1-b]thiazole)-2-ethyl]-2-piperazinone To a solution of the product from Step K (500 mg, 0.73 mmol) in 7 mL of tetrahydrofuran was added tributylphosphine (0.27 mL, 1.09 mmol). After cooling to 0° C., di-tert-butylazodicarboxylate (251 mg g, 1.09 mmol) was added, and the reaction was allowed to come to room temperature overnight. The solution was concentrated in vacuo, partitioned between EtOAc and water, washed with brine, dried (MgSO$_4$), filtered, and concentrated in vacuo. The crude product was purified by silica gel chromatography (0%→3% MeOH/CH$_2$Cl$_2$) to provide the title product.

Step M: Preparation of 19,20-Dihydro-19-oxo-30-thia-5H-3,5:18,21-diethano-12,14-etheno-6,10-metheno-benzo[d] imidazo[4,3-1][1,6,9,13]oxatriazacyclononadecine-9-carbonitrile A suspension of product from Step L (300 mg, 0.45 mmol), potassium fluoride (40 wt % on alumina, 200 mg, 1.34 mmol), and 18-crown-6 (24 mg, 0.089 mmol) in acetonitrile (10 mL) was heated at 85° C. for 48 hours. The reaction was filtered and concentrated in vacuo to give crude product which was purified by column chromatography (0→10% methanol/methylene chloride). The product was purified again by the automated reverse-phase HPLC, and the product was triturated with methanol. The white solid was dried under vacuum to provide the title compound. High Res Mass calculated for: C$_{28}$H$_{24}$N$_5$O$_2$S$_1$ (M+1): 494.1645 Found: 494.1658 (M+1).

Example 9

In vitro Inhibition of Ras Farnesyl Transferase

Transferase Assays. Isoprenyl-protein transferase activity assays are carried out at 30° C. unless noted otherwise. A typical reaction contains (in a final volume of 50 μL): [$^3$H]farnesyl diphosphate, Ras protein, 50 mM HEPES, pH 7.5, 5 MM MgCl$_2$, 5 mM dithiothreitol, 10 μM ZnCl$_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) Biochemistry 32:5167–5176. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor IC$_{50}$ determinations are as follows: FTase, 650 nM Ras-CVLS (SEQ.ID.NO.: 1), 100 nM farnesyl diphosphate.

The compounds of the instant invention are tested for inhibitory activity against human FPTase by the assay described above. The compounds of the instant invention described in the above Examples 1–8 were tested for inhibitory activity against human FPTase by the assay described above and were found to have IC$_{50}$ of ≦5 μM.

Example 10

Modified In vitro GGTase Inhibition Assay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5 mM ATP), 5 mM MgCl$_2$, 10 μM ZnCl$_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 2). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25 fold into the enzyme assay mixture. IC$_{50}$ values are determined with Ras peptide near K$_M$ concentrations. Enzyme and substrate concentrations for inhibitor IC$_{50}$ determinations are as follows: 75 pM GGTase-I, 1.6 μM Ras peptide, 100 nM geranylgeranyl diphosphate.

The compounds of the instant invention are tested for inhibitory activity against human GGTase-type I by the assay described above.

Example 11

Cell-based in vitro Ras Farnesylation Assay

The cell line used in this assay is a v-ras line derived from either Rat1 or NIH3T3 cells, which expressed viral Ha-ras p21. The assay is performed essentially as described in DeClue, J. E. et al., Cancer Research 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 μCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 μl of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/ 0.1%/ SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 12

Cell-based in vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 13

Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid, pDSE101

The SEAP reporter plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) *J. Virol.*, 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) *Oncogene*, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.

Sense strand N-terminal SEAP: 5' GAGAGGGAATTCGG GCCCTTCCTGCATGCTGCTGCTGCTGCT GCTGGGC 3' (SEQ.ID.NO.:4)

Antisense strand N-terminal SEAP: 5' GAGAGAGCTCGA GGTTAACCCGGGTGCGCGGCGTCGGTGGT 3' (SEQ.ID.NO.:5)

Sense strand C-terminal SEAP: 5' GAGAGAGTCTAG AGTTAACCCGTGGTCCCCGCGTTGCTTCCT 3' (SEQ.ID.NO.:6)

Antisense strand C-terminal SEAP: 5' GAAGAGGAAGCT TGGTACCGCCACTGGGCTGTAGGTGGTGGCT 3' (SEQ.ID.NO.:7)

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 5) introduces an internal translation STOP codon within the SEAP gene along with the HpaI site. The C-terminal oligos (SEQ.ID.NO.: 6 and SEQ.ID.NO.: 7) were used to amplify a 412 bp C-terminal PCR product containing HpaI and HindIII restriction sites. The sense strand C-terminal oligo (SEQ.ID.NO.: 6) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electro-phoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP-A

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand: 5' GGCAGAGCTCGTTTAGTGAACCGT-CAG 3' (SEQ.ID.NO.: 8)

Antisense strand: 5' GAGAGATCTCAAGGACGGT-GACTGCAG 3' (SEQ.ID.NO.: 9)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf(−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP-A (deposited in the ATCC under Budapest Treaty on Aug. 27, 1998, and designated ATCC), contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Alternative Construction of a Constitutively Expressing SEAP Plasmid pCMV-SEAP-B An expression plasmid constitutively expressing the SEAP protein can be created by placing the sequence encoding a truncated SEAP gene downstream of the cytomegalovirus (CMV) IE-1 promoter and upstream of the 3' unstranslated region of the bovine growth hormone gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter and bovine growth hormone poly-A sequence can be cut with EcoRI generating two fragments. The vector fragment can be isolated by agarose electrophoresis and religated. The resulting plasmid is named pCMV-AKI. The DNA sequence encoding the truncated SEAP gene can be inserted into the pCMV-AKI plasmid at a unique Bgl-II in the vector. The SEAP gene is cut out of plasmid pGEMzf(−)/SEAP (described above) using EcoRI and HindIII. The fragments are filled in with Klenow DNA polymerase and the 1970 base pair fragment is isolated from the vector fragment by agarose gel electrophoresis. The pCMV-AKI vector is prepared by digesting with Bgl-II and filling in the ends with Klenow DNA polymerase. The final construct is generated by blunt end ligating the SEAP fragment into the vector and transforming the ligation reaction into E. coli DH5α cells. Transformants can then be screened for the proper insert and mapped for restriction fragment orientation. Properly oriented recombinant constructs would be sequenced across the cloning junctions to verify the correct sequence. The resulting plasmid, named pCMV-SEAP-B contains a modified SEAP sequence downstream of the cytomegalovirus immediate early promoter, IE1, and upstream of a bovine growth hormone poly-A sequence. The plasmid would express SEAP in a constitutive nammer when transfected into mammalian cells.

Cloning of a Myristylated Viral-H-ras Expression Plasmid pSMS600

A DNA fragment containing viral-H-ras can be PCRed from plasmid "HB-11 (deposited in the ATCC under Budapest Treaty on Aug. 27, 1997, and designated ATCC 209,218) using the following oligos.

Sense Strand:
5'TCTCCTCGAGGCCACCATGGGGAGTAGCAAGAG CAAGCCTAAGGACCCCAGCCAGCGCCGGATGA CAGAATACAAGCTTGTGGTGG 3'. (SEQ.ID.NO.: 10)

AntiSense:
5'CACATCTAGATCAGGACAGCACAGACTTGCAGC 3'. (SEQ.ID.NO.: 11)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The Xhol-Xbal fragment can be ligated into the mammalian expression plasmid pCI (Promega) cut with XhoI and Xbal. This results in a plasmid, pSMS600, in which the recombinant myr-viral-H-ras gene is constitutively transcribed from the CMV promoter of the pCI vector.

Cloning of a Viral-H-ras-CVLL Expression Plasmid pSMS601

A viral-H-ras clone with a C-terminal sequence encoding the amino acids CVLL can be cloned from the plasmid "HB-11" by PCR using the following oligos.
Sense Strand:
5'TCTCCTCGAGGCCACCATGACAGAATACAAGCTT GTGGTGG-3' (SEQ.ID.NO.: 12)
Antisense Strand:
5'CACTCTAGACTGGTGTCAGAGCAGCACACACTT GCAGC-3' (SEQ.ID.NO.: 13)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid, pSMS601, in which the mutated viral-H-ras-CVLL gene is constitutively transcribed from the CMV promoter of the pCI vector.

Cloning of Cellular-H-ras-Leu61 Expression Plasmid pSMS620

The human cellular-H-ras gene can be PCRed from a human cerebral cortex cDNA library (Clontech) using the following oligonucleotide primers.
Sense Strand:
5'-GAGAGAATTCGCCACCATGACGGAATATAAGCT GGTGG-3' (SEQ.ID.NO.: 14)
Antisense Strand:
5'-GAGAGTCGACGCGTCAGGAGAGCACACACTT GC-3' (SEQ.ID.NO.: 15)

The primers will amplify a c-H-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-H-ras fragment can be ligated ligated into an EcoRI -Sal I cut mutagenesis vector pAlter-1 (Promega). Mutation of glutamine-61 to a leucine can be accomplished using the manufacturer's protocols and the following oligonucleotide:
5'-CCGCCGGCCTGGAGGAGTACAG-3' (SEQ.ID.NO.: 16)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid, pSMS620, will constitutively transcribe c-H-ras-Leu61 from the CMV promoter of the pCI vector.

Cloning of a c-N-ras-Val-12 Expression Plasmid pSMS630

The human c-N-ras gene can be PCRed from a human cerebral cortex cDNA library (Clontech) using the following oligonucleotide primers.
Sense Strand:
5'-GAGAGAATTCGCCACCATGACTGAGTACAAACT GGTGG-3' SEQ.ID.NO.: 17)
Antisense Strand:
5'-GAGAGTCGACTTGTTACATCACCACACATGGC-3' (SEQ.ID.NO.: 18)

The primers will amplify a c-N-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:
5'-GCTGGAGCAGTTGGTGTTGGG-3' (SEQ.ID.NO.: 19)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid, pSMS630, will constitutively transcribe c-N-ras-Val-12 from the CMV promoter of the pCI vector.

Cloning of a c-K4B-ras-Val-12 Expression Plasmid pSMS640

The human c-K4B-ras gene can be PCRed from a human cerebral cortex cDNA library (Clontech) using the following oligo-nucleotide primers.
Sense Strand:
5'-GAGAGGTACCGCCACCATGACTGAATATAAACT TGTGG-3' (SEQ.ID.NO.: 20)
Antisense Strand:
5'-CTCTGTCGACGTATTTACATAATTACACACTTTG TC-3' (SEQ.ID.NO.: 21)

The primers will amplify a c-K4B-Ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K4B-ras fragment can be ligated into a KpnI-Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 22)

After selection and sequencing for the correct nucleotide substitution, the mutated c-K4B-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K4B-ras-Val-12 from the CMV promoter of the pCI vector.

Cloning of c-K-ras4A-Val-12 Expression Plasmid pSMS650

The human c-K4A-ras gene can be PCRed from a human cerebral cortex cDNA library (Clontech) using the following oligo-nucleotide primers.
Sense Strand:
5'-GAGAGGTACCGCCACCATGACTGAATATAAACT TGTGG-3' (SEQ.ID.NO.: 23)
Antisense Strand:
5'-CTCTGTCGACAGATTACATTATAATGCATTTTTT AATTTTCACAC-3' (SEQ.ID.NO.: 24)

The primers will amplify a c-K4A-Ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras4A fragment can be ligated into a KpnI -Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 25)

After selection and sequencing for the correct nucleotide substitution, the mutated c-K4A-ras-Val-12 can be excised from the pAlter-1 vector, using KpnI and Sal I, and be directly ligated into the vector pCI (Promega) which has been digested with KpnI and Sal I. The new recombinant plasmid, pSMS650, will constitutively transcribe c-K4A-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1× Pen/Strep+1× glutamine+ 1× NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. (A ras expression plasmid is not included when the cell is transfected with the pCMV-SEAP plasmid.) For 10 cm plates 600 µl of $CaCl_2$-DNA solution is added dropwise while vortexing to 600 µl of 2× HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. No. 31053-028)+0.5% charcoal stripped calf serum+1× (Pen/ Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+ 1× (Pen/Strep, Glutamine and NEAA). Transfected cells are plated in a 96 well microtiter plate (100 µl/well) to which drug, diluted in media, has already been added in a volume of 100 µl. The final volume per well is 200 µl with each drug concentration repeated in triplicate over a range of half-log steps.

Incubation of cells and drugs is for 36 hrs at 37° under $CO_2$. At the end of the incubation period, cells are examined micro-scopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combined with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-CaPO₄ precipitate for 10 cm. plate of cells | |
|---|---|
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |
| 2M CaCl₂ | 74 µl |
| dH₂O | 506 µl |
| 2X HBS Buffer | |
| 280 mM NaCl | |
| 10 mM KCl | |
| 1.5 mM Na₂HPO₄ 2H₂O | |
| 12 mM dextrose | |
| 50 mM HEPES | |
| Final pH = 7.05 | |
| Luminesence Buffer (26 ml) | |
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |
| Assay Buffer | |
| Add 0.05M Na₂CO₃ to 0.05M NaHCO₃ to obtain pH 9.5. Make 1 mM in MgCl₂ | |

Example 14

The Processing Assays Employed are Modifications of that Described by DeClue et al [Cancer Research 51, 712–717, 1991].

K4B-Ras Processing Inhibition Assay

PSN-1 (human pancreatic carcinoma) or viral-K4B-ras-transformed Rat1 cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 µM), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 µCi/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 µg/ml AEBSF, 10 µg/ml aprotinin, 2 µg/ml leupeptin and 2 µg/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 µg of the pan Ras monoclonal antibody, Y13-259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 µl elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 µg Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmll sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to hDJ-2 (Neomarkers Cat. # MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of hDJ (the slower-migrating species) is calculated by densitometry. Dose-response curves and $EC_{50}$ values are generated using 4-parameter curve fits in SigmaPlot software.

Example 15

Rap1 Processing Inhibition Assay

Protocol A

Cells are labeled, incubated and lysed as described in Example 14.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 $\mu$g of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 $\mu$g Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B

PSN-1 cells are passaged every 3–4 days in 10 cm plates, splitting near-confluent plates 1:20 and 1:40. The day before the assay is set up, $5 \times 10^6$ cells are plated on 15 cm plates to ensure the same stage of confluency in each assay. The media for these cells is RPM1 1640 (Gibco), with 15% fetal bovine serum and 1× Pen/Strep antibiotic mix. The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37 C. overnight.

The compounds to be assayed are diluted in DMSO in 1/2-log dilutions. The range of final concentrations to be assayed is generally 0.1–100 $\mu$M. Four concentrations per compound is typical. The compounds are diluted so that each concentration is 1000× of the final concentration (i.e., for a 10 $\mu$M data point, a 10 mM stock of the compound is needed).

2 $\mu$L of each 1000× compound stock is diluted into 1 ml media to produce a 2× stock of compound. A vehicle control solution (2 $\mu$L DMSO to 1 ml media), is utilized. 0.5 ml of the 2× stocks of compound are added to the cells.

After 24 hours, the media is aspirated from the assay plates. Each well is rinsed with 1 ml PBS, and the PBS is aspirated. 180 $\mu$L SDS-PAGE sample buffer (Novex) containing 5% 2-mercapto-ethanol is added to each well. The plates are heated to 100° C. for 5 minutes using a heat block containing an adapter for assay plates. The plates are placed on ice. After 10 minutes, 20 $\mu$L of an RNAse/DNase mix is added per well. This mix is 1 mg/ml DNaseI (Worthington Enzymes), 0.25 mg/ml Rnase A (Worthington Enzymes), 0.5 M Tris-HCl pH 8.0 and 50 mM $MgCl_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 $\mu$l of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20 ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C

This protocol allows the determination of an $EC_{50}$ for inhibition of processing of Rap1a. The assay is run as described in Protocol B with the following modifications. 20 µl of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121;Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant™ software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

EXAMPLE 16

In Vivo Tumor Growth Inhibition Assay (Nude Mouse)

In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995)) and N. E. Kohl et al. (Proc. Nat. Acad. Sci. U.S.A., 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle or compound treatment group. Animals are dosed subcutaneously starting on day 1 and daily for the duration of the experiment. Alternatively, the farnesyl-protein transferase inhibitor may be administered by a continuous infusion pump. Compound or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound of the formula A:

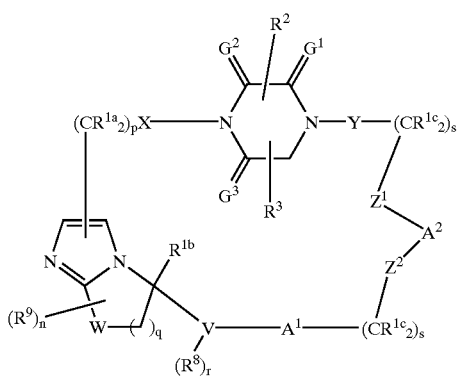

wherein:

$R^{1a}$ and $R^{1c}$ are independently selected from:
a) hydrogen,
b) aryl, heterocycle, $C_3$–$C_{10}$ cycloalkyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) unsubstituted or substituted $C_1$–$C_6$ alkyl, unsubstituted or substituted $C_2$–$C_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$–$C_6$ alkynyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, —$N(R^{10})_2$, and $R^{11}OC(O)$—$NR^{10}$—,
or two $R^{1a}$s or two $R^{1c}$s on the same carbon atom may be combined to form —$(CH_2)t$—;

$R^{1b}$ is selected from:
a) hydrogen,
b) aryl, heterocycle, $C_3$–$C_{10}$ cycloalkyl, $(R^{10})_2N$—$C(O)$—, $(R^{10})_2N$—$C(NR^{10})$—, $R^{10}C(O)$—or $R^{10}OC(O)$—, and
c) unsubstituted or substituted $C_1$–$C_6$ alkyl, unsubstituted or substituted $C_2$–$C_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$–$C_6$ alkynyl is selected from unsubstituted or substituted aryl, heterocyclic, $C_3$–$C_{10}$ cycloalkyl, $C_2$–$C_6$ alkenyl, $C_2$–$C_6$ alkynyl, one or more fluorines, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, —$N(R^{10})_2$, and $R^{11}OC(O)$—$NR^{10}$—;

$R^2$ and $R^3$ are independently selected from H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

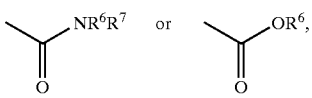

wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) CN,
2) $C_{3-6}$ cycloalkyl,
3) $OR^6$,
4) $SR^4$, $S(O)R^4$, $SO_2R^4$,

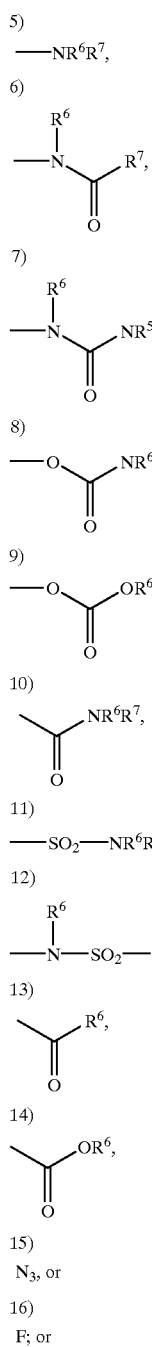

5) —NR⁶R⁷,

6)

7)

8)

9)

10)

11) —SO₂—NR⁶R⁷,

12)

13)

14)

15) N₃, or

16) F; or

R² and R³ are attached to the same carbon atom and are combined to form —(CH₂)u— wherein one of the carbon atoms is optionally replaced by a moiety selected from O, $S(O)_m$, —NC(O)—, and —N(COR¹⁰)—; and R⁴ is selected from $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO,

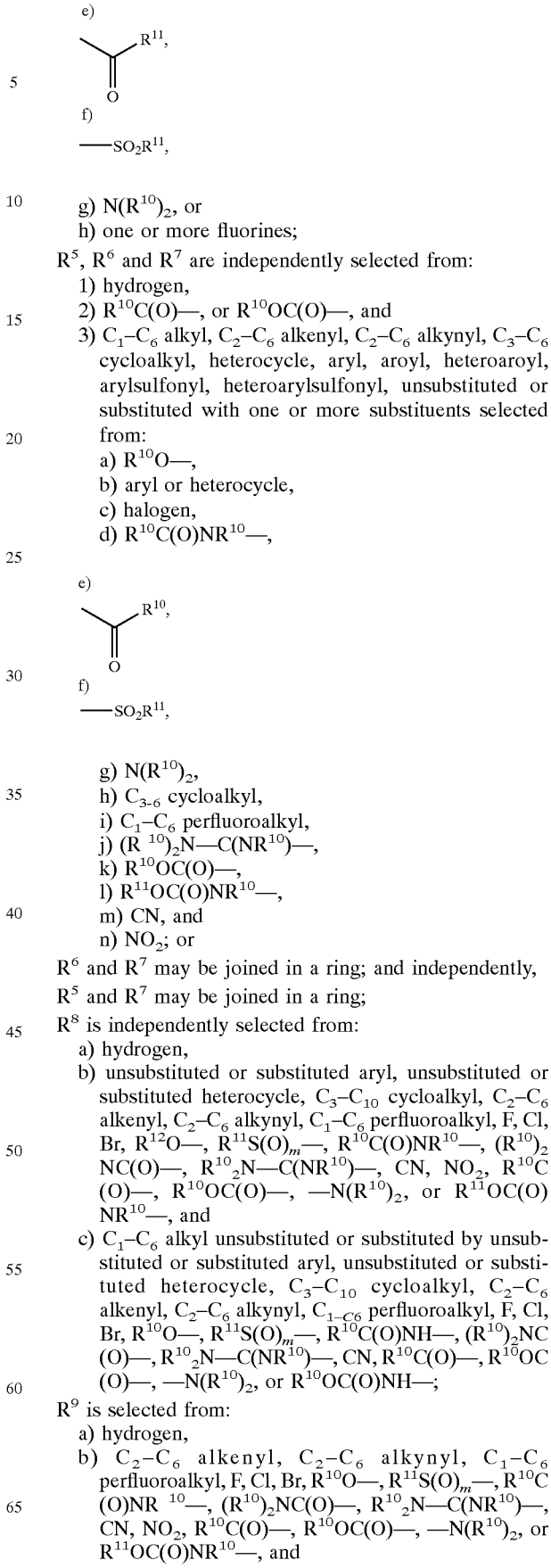

e)

f) —SO₂R¹¹, g) N(R¹⁰)₂, or
h) one or more fluorines;

R⁵, R⁶ and R⁷ are independently selected from:
  1) hydrogen,
  2) R¹⁰C(O)—, or R¹⁰OC(O)—, and
  3) $C_1$–$C_6$ alkyl, $C_2$–$C_6$ alkenyl, $C_2$–$C_6$ alkynyl, $C_3$–$C_6$ cycloalkyl, heterocycle, aryl, aroyl, heteroaroyl, arylsulfonyl, heteroarylsulfonyl, unsubstituted or substituted with one or more substituents selected from:
    a) R¹⁰O—,
    b) aryl or heterocycle,
    c) halogen,
    d) R¹⁰C(O)NR¹⁰—, e)

f) —SO₂R¹¹, g) N(R¹⁰)₂,
  h) $C_{3-6}$ cycloalkyl,
  i) $C_1$–$C_6$ perfluoroalkyl,
  j) (R¹⁰)₂N—C(NR¹⁰)—,
  k) R¹⁰OC(O)—,
  l) R¹¹OC(O)NR¹⁰—,
  m) CN, and
  n) NO₂; or R⁶ and R⁷ may be joined in a ring; and independently, R⁵ and R⁷ may be joined in a ring;

R⁸ is independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, R¹²O—, $R^{11}S(O)_m$—, R¹⁰C(O)NR¹⁰—, (R¹⁰)₂NC(O)—, R¹⁰₂N—C(NR¹⁰)—, CN, NO₂, R¹⁰C(O)—, R¹⁰OC(O)—, —N(R¹⁰)₂, or R¹¹OC(O)NR¹⁰—, and
  c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $C_{1-C6}$ perfluoroalkyl, F, Cl, Br, R¹⁰O—, $R^{11}S(O)_m$—, R¹⁰C(O)NH—, (R¹⁰)₂NC(O)—, R¹⁰₂N—C(NR¹⁰)—, CN, R¹⁰C(O)—, R¹⁰OC(O)—, —N(R¹⁰)₂, or R¹⁰OC(O)NH—;

R⁹ is selected from:
  a) hydrogen,
  b) $C_2$–$C_6$ alkenyl, $C_2$–$C_6$ alkynyl, $C_1$–$C_6$ perfluoroalkyl, F, Cl, Br, R¹⁰O—, $R^{11}S(O)_m$—, R¹⁰C(O)NR¹⁰—, (R¹⁰)₂NC(O)—, R¹⁰₂N—C(NR¹⁰)—, CN, NO₂, R¹⁰C(O)—, R¹⁰OC(O)—, —N(R¹⁰)₂, or R¹¹OC(O)NR¹⁰—, and c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, $C_1$–$C_6$ alkyl substituted with one or more fluorines, benzyl, unsubstituted or substituted aryl and unsubstituted or substituted heterocycle;

$R^{11}$ is independently selected from $C_1$–$C_6$ alkyl, $C_1$–$C_6$ alkyl substituted with one or more fluorines, unsubstituted or substituted aryl and unsubstituted or substituted heterocycle;

$R^{12}$ is independently selected from hydrogen, $C_1$–$C_6$ alkyl, $C_1$–$C_6$ alkyl substituted with one or more fluorines, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, —NR$^{10}$C(O)NR$^{10}$— and S(O)$_m$;

$A^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, —NR$^{10}$C(O)NR$^{10}$—, S(O)$_m$ and —C(R$^{1c}$)$_2$—;

$G^1$, $G^2$ and $G^3$ are independently selected from ($R^2$,$R^3$) and O;

V is selected from:
a) heterocycle, and
b) aryl;

W is $S(O)_m$, O or $CH_2$;

X is selected from: a bond, —C(O)—, —NR$^{10}$C(O)—, —N(R$^{10}$)S(O)$_2$— and S(O)$_2$;

Y is selected from a bond, —C(O)—, —C(O)NR$^{10}$—, —C(O)O— and —S(O)$_m$;

$Z^1$ is selected from unsubstituted or substituted aryl and unsubstituted or substituted heterocycle, wherein the substituted aryl or substituted heterocycle is substituted with one or more of:
1) $C_{1-8}$ alkyl, $C_{2-8}$ alkenyl or $C_{2-8}$ alkynyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) —$S(O)_mR^4$,
g) —$C(O)NR^6R^7$, or
h) one or more fluorines;
2) substituted or unsubstituted aryl or substituted or unsubstituted heterocycle,
3) halogen,
4) $OR^6$,
5) $NR^6R^7$,
6) CN,
7) $NO_2$,
8) $CF_3$;
9) —$S(O)_mR^4$,
10) —$OS(O)_2R^4$,
11) —$C(O)NR^6R^7$,
12) —$C(O)OR^6$, or
13) $C_3$–$C_6$ cycloalkyl;

$Z^2$ is selected from a bond, unsubstituted or substituted aryl and unsubstituted or substituted heterocycle, wherein the substituted aryl or substituted heterocycle is substituted with one or more of:
1) $C_{1-8}$ alkyl, $C_{2-8}$ alkenyl or $C_{2-8}$ alkynyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) —$S(O)_mR^4$,
g) —$C(O)NR^6R^7$, or
h) one or more fluorines;
2) substituted or unsubstituted aryl or substituted or unsubstituted heterocycle,
3) halogen,
4) $OR^6$,
5) $NR^6R^7$,
6) CN,
7) $NO_2$,
8) $CF_3$;
9) —$S(O)_mR^4$,
10) —$OS(O)_2R^4$,
11) —$C(O)NR^6R^7$,
12) —$C(O)OR^6$, or
13) $C_3$–$C_6$ cycloalkyl;

m is independently 0, 1 or 2;
n is 1 or 2;
p is independently 0, 1, 2, 3 or 4;
q is 1 or 2;
r is 0 to 5;
s is independently 0, 1, 2, 3 or 4;
t is 2, 3, 4, 5 or 6; and
u is 2, 3, 4 or 5;
or a pharmaceutically acceptable salt or stereoisomer thereof.

2. The compound according to claim 1 of the formula B:

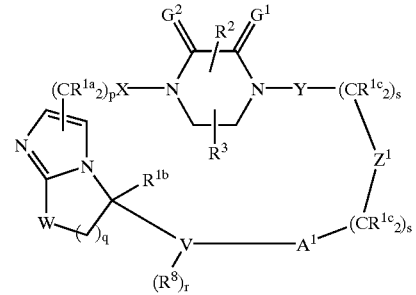

B wherein:
$R^{1a}$ and $R^{1c}$ are independently selected from:
a) hydrogen,
b) $R^{10}O$—, —$N(R^{10})_2$, $R^{10}C(O)NR^{10}$—, $R^{11}OC(O)O$— or $R^{11}OC(O)NR^{10}$—, and
c) $C_1$–$C_6$ alkyl, unsubstituted or substituted by $R^{10}O$—, —$N(R^{10})_2$, $R^{10}C(O)NR^{10}$—, $R^{11}OC(O)O$—, $R^{11}OC(O)NR^{10}$— or $R^{11}S(O)_m$—;

$R^{1b}$ is selected from:
a) hydrogen, and
b) unsubstituted or substituted $C_1$–$C_6$ alkyl, wherein the substituent on the substituted $C_1$–$C_6$ alkyl is selected from one or more fluorines, $R^{10}O$—, $R^{11}S(O)_m$—, $R^{10}C(O)NR^{10}$—, $R^{10}OC(O)O$— and $R^{11}OC(O)$—$NR^{10}$—;

$R^3$ is selected from H and CH$_3$;

$R^2$ is selected from H;

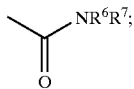

and C$_{1-5}$ alkyl, unbranched or branched, unsubstituted or substituted with one or more of:
1) aryl,
2) heterocycle,
3) OR$^6$,
4) SR$^4$, SO$_2$R$^4$, or 5)
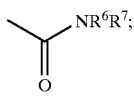

and any two of R$^2$ and R$^3$ are optionally attached to the same carbon atom;

R$^4$ is selected from:
C$_{1-4}$ alkyl and C$_{3-6}$ cycloalkyl, unsubstituted or substituted with:
  a) C$_{1-4}$ alkoxy,
  b) one or more fluorines, or
  c) aryl or heterocycle;

R$^6$ and R$^7$ are independently selected from H; C$_{1-6}$ alkyl, C$_{3-6}$ cycloalkyl, heterocycle, aryl, aroyl, heteroaroyl, arylsulfonyl, heteroarylsulfonyl, unsubstituted or substituted with one or two:
  a) C$_{1-4}$ alkoxy,
  b) aryl or heterocycle,
  c) halogen,
  d) HO,
  e)
  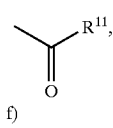
  f)
  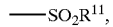
  g) N(R$^{10}$)$_2$, or
  h) C$_{3-6}$ cycloalkyl;

R$^8$ is independently selected from:
  a) hydrogen,
  b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$ C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by: unsubstituted or substituted aryl, C$_1$–C$_6$ perfluoroalkyl, R$^{10}$O—, R$^{10}$C(O) NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{10}$ is independently selected from hydrogen, C$_1$–C$_6$ alkyl, C$_1$–C$_6$ alkyl substituted with one or more fluorines, benzyl and unsubstituted or substituted aryl;

R$^{11}$ is independently selected from C$_1$–C$_6$ alkyl, C$_1$–C$_6$ alkyl substituted with one or more fluorines, and unsubstituted or substituted aryl;

R$^{12}$ is independently selected from hydrogen, C$_1$–C$_6$ alkyl, unsubstituted or substituted benzyl, unsubstituted or substituted aryl, unsubstituted or substituted heterocycle, and C$_1$–C$_6$ alkyl substituted with one or more fluorines, unsubstituted or substituted aryl or unsubstituted or substituted heterocycle;

A$^1$ is selected from a bond, O, —N(R$^{10}$)— and S(O)$_m$;

G$^1$ and G$^2$ are independently selected from (R$^2$,R$^3$) and O;

V is selected from:
  a) heterocycle selected from pyridinyl, pyridonyl, 2-oxopiperidinyl, indolyl, quinolinyl and isoquinolinyl, and
  b) aryl;

W is S or CH$_2$;

X is selected from a bond, —C(O)— or —S(O)$_m$;

Y is selected from a bond, —C(O)—, —C(O)NR$^{10}$—, —C(O)O— and —S(O)$_m$;

Z$^1$ is selected from unsubstituted or substituted aryl or unsubstituted or substituted heterocycle, wherein the substituted aryl or substituted heterocycle is independently substituted with one or two of:
  1) C$_{1-8}$ alkyl, C$_{2-8}$ alkenyl or C$_{2-8}$ alkynyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$,
    g) —C(O)NR$^6$R$^7$, or
    h) one or more fluorines;
  2) substituted or unsubstituted aryl or substituted or unsubstituted heterocycle,
  3) halogen,
  4) OR$^6$,
  5) NR$^6$R$^7$,
  6) CN,
  7) N$_2$,
  8) CF$_3$,
  9) —S(O)$_m$R$^4$,
  10) —OS(O)$_2$R$^4$,
  11) —C(O)NR$^6$R$^7$,
  12) —C(O)OR$^6$, or
  13) C$_3$–C$_6$ cycloalkyl;

m is 0, 1 or 2;

n is 0, 1 or 2;

p is 0, 1, 2, 3 or 4;

q is 1 or 2;

r is 0 to 5; and s is independently 0, 1, 2 or 3;

or a pharmaceutically acceptable salt or stereoisomer thereof.

3. The compound according to claim 2 of the formula C:

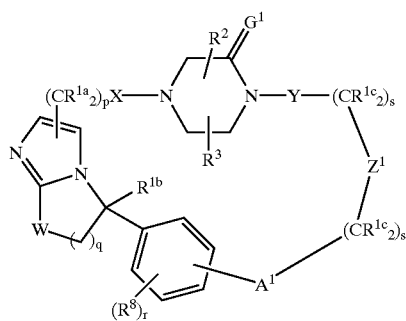

wherein:
$R^{1a}$ and $R^{1c}$ are independently selected from:
  a) hydrogen,
  b) $R^{10}O-$, $-N(R^{10})_2$, $R^{10}C(O)NR^{10}-$, $R^{11}OC(O)O-$ or $R^{11}OC(O)NR^{10}$, and
  c) $C_1-C_6$ alkyl, unsubstituted or substituted by $R^{10}O-$, $-N(R^{10})_2$, $R^{10}C(O)NR^{10}-$, $R^{11}OC(O)O-$, $R^{11}OC(O)NR^{10}$ or $R^{11}S(O)_m-$;

$R^{1b}$ is selected from:
  a) hydrogen, and
  b) unsubstituted or substituted $C_1-C_6$ alkyl, wherein the substituent on the substituted $C_1-C_6$ alkyl is selected from one or more fluorines, $R^{10}O-$, $R^{11}S(O)_m-$, $R^{10}C(O)NR^{10}-$, $R^{10}OC(O)O-$ and $R^{11}OC(O)-NR^{10}-$;

$R^3$ is selected from H and $CH_3$;
$R^2$ is selected from H;

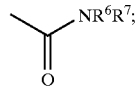

and $C_{1-5}$ alkyl, unbranched or branched, unsubstituted or substituted with one or more of:
  1) aryl,
  2) heterocycle,
  3) $OR^6$,
  4) $SR^4$, $SO_2R^4$, or
  5)

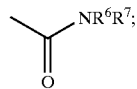

and any two of $R^2$ and $R^3$ are optionally attached to the same carbon atom;

$R^4$ is selected from:
  $C_{1-4}$ alkyl and $C_{3-6}$ cycloalkyl, unsubstituted or substituted with:
    a) $C_{1-4}$ alkoxy,
    b) one or more fluorines, or
    c) aryl or heterocycle;

$R^6$ and $R^7$ are independently selected from H; $C_{1-6}$ alkyl, $C_{3-6}$ cycloalkyl, heterocycle, aryl, aroyl, heteroaroyl, arylsulfonyl, heteroarylsulfonyl, unsubstituted or substituted with one or two:
  a) $C_{1-4}$ alkoxy,
  b) aryl or heterocycle,
  c) halogen,
  d) HO,
  e)

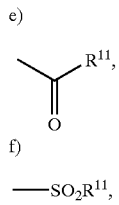

f) $-SO_2R^{11}$,
  g) $N(R^{10})_2$, or
  h) $C_{3-6}$ cycloalkyl;

$R^8$ is independently selected from:
  a) hydrogen,
  b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{12}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
  c) $C_1-C_6$ alkyl substituted by: unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{10}$ is independently selected from hydrogen, $C_1-C_6$ alkyl, $C_1-C_6$ alkyl substituted with one or more fluorines, benzyl and unsubstituted or substituted aryl;

$R^{11}$ is independently selected from $C_1-C_6$ alkyl, $C_1-C_6$ alkyl substituted with one or more fluorines and unsubstituted or substituted aryl;

$R^{12}$ is independently selected from hydrogen, $C_1-C_6$ alkyl, unsubstituted or substituted benzyl, unsubstituted or substituted aryl, unsubstituted or substituted heterocycle, and $C_1-C_6$ alkyl substituted with one or more fluorines, unsubstituted or substituted aryl or unsubstituted or substituted heterocycle;

$A^1$ is selected from a bond, O, $-N(R^{10})-$ and $S(O)_m$;
$G^1$ is selected from $(R^2,R^3)$ and O;
W is S or $CH_2$;
X is selected from a bond, $-C(O)-$ or $-S(O)_m$;
Y is selected from a bond, $-C(O)-$, $-C(O)NR^{10}-$, $-C(O)O-$, or $-S(O)_m$;
$Z^1$ is selected from unsubstituted or substituted aryl or unsubstituted or substituted heterocycle, wherein the substituted aryl or substituted heterocycle is independently substituted with one or two of:
  1) $C_{1-8}$ alkyl, $C_{2-8}$ alkenyl or $C_{2-8}$ alkynyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) $-S(O)_mR^4$,
    g) $-C(O)NR^6R^7$, or
    h) one or more fluorines;
  2) substituted or unsubstituted aryl or substituted or unsubstituted heterocycle,
  3) halogen,
  4) $OR^6$,
  5) $NR^6R^7$,
  6) CN,
  7) $NO_2$,
  8) $CF_3$,
  9) $-S(O)_mR^4$,
  10) $-OS(O)_2R^4$,
  11) $-C(O)NR^6R^7$,
  12) $-C(O)OR^6$, or
  13) $C_3-C_6$ cycloalkyl;

m is 0, 1 or 2;
n is 0, 1 or 2;
p is 0 1, 2, 3 or 4;
q is 1 or 2;
r is 0 to 5; and
s is independently 0, 1, 2 or 3;
or a pharmaceutically acceptable salt or stereoisomer thereof.

4. A compound which is selected from:
(R)-15-Bromo-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile
(S)-15-Bromo-19,20-dihydro-9,22-dioxo-28-thia-5H,17H-3,5:18,21-diethano-6,10:12,16-dimetheno-22H-imidazo[3,4-h][1,8,11,14]oxatriazacycloeicosine-9-carbonitrile
(R)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile
(S)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile
15-Chloro-9,20-dihydro-19-oxo-5H,17H-3,5:18,21-diethano-6,10:12,16-dimetheno-22H-imidazo[3,4-h][1,8,11,14]oxatriazacycloeicosine-9-carbonitrile
19,20-Dihydro-19,22-dioxo-5H-3,5:18,21-diethano-12,14-etheno-6,10-metheno-benzo[d]imidazo[4,3-k][1,6,9,12]oxatriazacyclooctadecine-9-carbonitrile
22,23-Dihydro-22-oxo-31-thia-5H-3,5:21,24-diethano-6,10:12,16-dimetheno-12H,25H-benzo[g]imidazo[4,3-n][1,8,11,14]oxatriazacycloheneicosine-9-carbonitrile.
15-Fluoro-19,20-dihydro-19,22-dioxo-28-5H,17H-3,5:18,21-diethano-6,10:12,16-dimetheno-22H-imidazo[3,4-h][1,8,11,14]oxatriazacycloeicosine-9-carbonitrile
(R)-15-Chloro-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile
(S)-15-Chloro-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile
19,20-Dihydro-19-oxo-30-thia-5H-3,5:18,21-diethano-12,14-etheno-6,10-metheno-benzo[d]imidazo[4,3-1][1,6,9,13]oxatriazacyclononadecine-9-carbonitrile
(R)-19,20-Dihydro-19-oxo-30-thia-5H-3,5:18,21-diethano-12,14-etheno-6,10-metheno-benzo [d]imidazo[4,3-1][1,6,9,13]oxatriazacyclononadecine-9-carbonitrile
(S)-19,20-Dihydro-19-oxo-30-thia-5H-3,5:18,21-diethano-12,14-etheno-6,10-metheno-benzo [d]imidazo[4,3-1][1,6,9,13]oxatriazacyclononadecine-9-carbonitrile
or a pharmaceutically acceptable salt or stereoisomer thereof.

5. The compound according to claim 4 which is
(R)-15-Bromo-9,20-dihydro-9,22-dioxo-28-thia-5H,17H-3,5:18,21-diethano-6,10:12,16-dimetheno-22H-imidazo[3,4-h][1,8,11,14]oxatriazacycloeicosine-9-carbonitrile hydrochloride

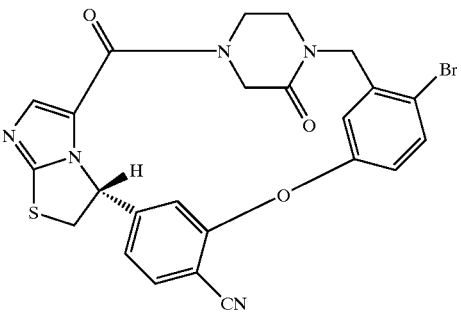

(S)-15-Bromo-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile hydrochloride

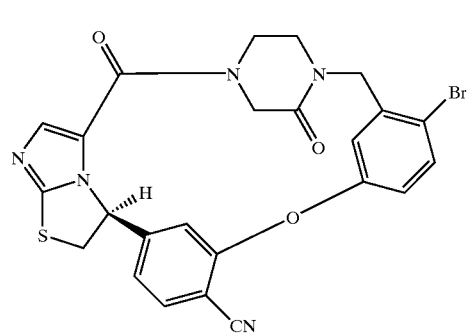

(R)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile hydrochloride

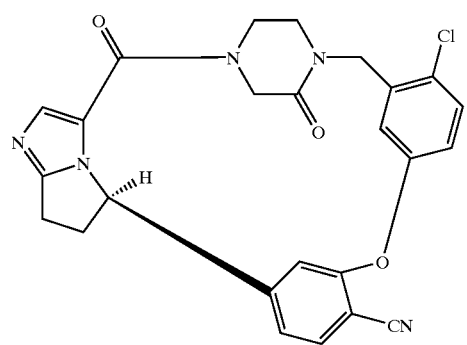

(S)-15-Chloro-19,20-dihydro-19,22-dioxo-5H,17H-3,5:18,21-diethano-6,10:12,16-dimetheno-22H-imidazo[3,4-h][1,8,11,14]oxatriazacycloeicosine-9-carbonitrile hydrochloride

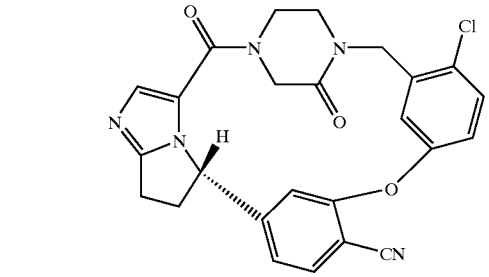

(R)-15-Chloro-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile

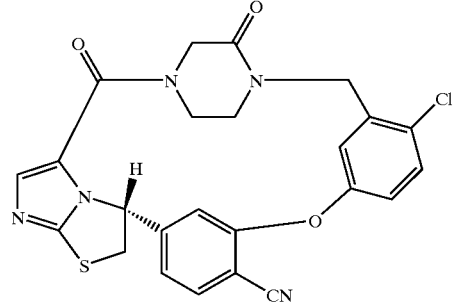

(S)-15-Chloro-19,20-dihydro-19,22-dioxo-28-thia-5H,17H-3,5:18,21-diethano-6,10:12,16-dimetheno-22H-imidazo[3,4-h][1,8,11,14]oxatriazacycloeicosine-9-carbonitrile

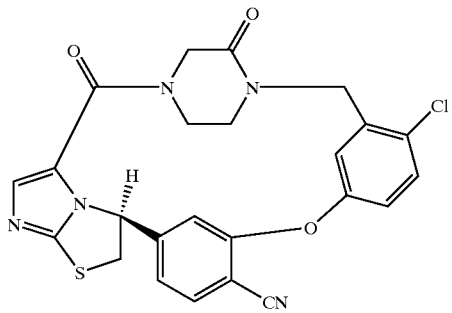

(R)-19,20-Dihydro-19-oxo-30-thia-5H-3,5:18,21-diethano-12,14-etheno-6,10-metheno-benzo[d]imidazo[4,3-1][1,6,9,13]oxatriazacyclononadecine-9-carbonitrile

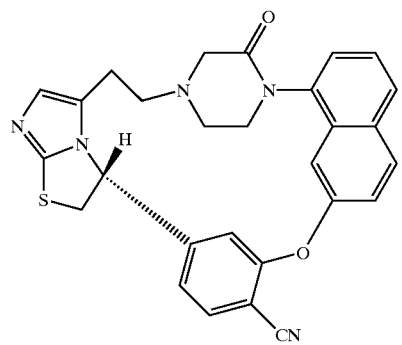

(S)-19,20-Dihydro-19-oxo-30-thia-5H-3,5:18,21-diethano-12,14-etheno-6,10-metheno-benzo[d]imidazo[4,3-1][1,6,9,13]oxatriazacyclononadecine-9-carbonitrile

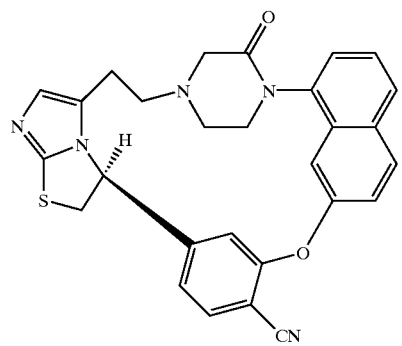

or a pharmaceutically acceptable salt or stereoisomer thereof.

6. A pharmaceutical composition comprising a pharmaceutical carrier, and dispersed therein, a therapeutically effective amount of a compound of claim 1.

7. A pharmaceutical composition comprising a pharmaceutical carrier, and dispersed therein, a therapeutically effective amount of a compound of claim 3.

8. A pharmaceutical composition comprising a pharmaceutical carrier, and dispersed therein, a therapeutically effective amount of a compound of claim 4.

9. A method for inhibiting prenyl-protein transferase which comprises administering to a mammal in need thereof a therapeutically effective amount of a composition of claim 6.

10. A method for inhibiting prenyl-protein transferase which comprises administering to a mammal in need thereof a therapeutically effective amount of a composition of claim 7.

11. A method for inhibiting prenyl-protein transferase which comprises administering to a mammal in need thereof a therapeutically effective amount of a composition of claim 8.

12. A process for making a pharmaceutical composition comprising combining a compound of claim 1 and a pharmaceutically acceptable carrier.

13. A method for preventing restenosis which comprises administering to a mammal in need thereof a therapeutically effective amount of a composition of claim 6.

14. A method for treating polycystic kidney disease which comprises administering to a mammal in need thereof a therapeutically effective amount of a composition of claim 6.

15. A method for treating neurofibromin benign proliferative disorder which comprises administering to a mammal in need thereof a therapeutically effective amount of a composition of claim 6.

16. A method for treating blindness related to retinal vascularization which comprises administering to a mammal in need thereof a therapeutically effective amount of a composition of claim 6.

17. A method for treating infections from hepatitis delta which comprises administering to a mammal in need thereof a therapeutically effective amount of a composition of claim 6.

* * * * *